US007676329B2

(12) United States Patent
Garczarek et al.

(10) Patent No.: US 7,676,329 B2
(45) Date of Patent: Mar. 9, 2010

(54) METHOD AND SYSTEM FOR PROCESSING MULTI-DIMENSIONAL MEASUREMENT DATA

(75) Inventors: Ursula Garczarek, Benediktbeuern (DE); Pavel Kubalec, Feldafing (DE); Wolfgang Hösel, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1081 days.

(21) Appl. No.: 11/112,919

(22) Filed: Apr. 22, 2005

(65) Prior Publication Data

US 2006/0080040 A1    Apr. 13, 2006

(30) Foreign Application Priority Data

Apr. 23, 2004    (EP)    ................... 04009709

(51) Int. Cl.
G01N 33/48    (2006.01)
(52) U.S. Cl. ....................................................... 702/19
(58) Field of Classification Search .................... 702/19
See application file for complete search history.

(56) References Cited

U.S. PATENT DOCUMENTS

| 5,672,869 | A | 9/1997 | Windig et al. ............... 250/282 |
| 5,995,989 | A | 11/1999 | Gedcke et al. .............. 708/300 |
| 2002/0095259 | A1 | 7/2002 | Hood et al. .................... 702/19 |
| 2002/0193950 | A1 | 12/2002 | Gavin et al. ................... 702/28 |
| 2003/0040123 | A1 | 2/2003 | Hastings ..................... 436/173 |

FOREIGN PATENT DOCUMENTS

| JP | 2001028252 | 1/2001 |
| WO | WO 92/07326 | 4/1992 |
| WO | WO 98/44536 | 10/1998 |
| WO | WO 00/22649 | 4/2000 |
| WO | WO 02/03056 A1 | 1/2002 |
| WO | WO 02/013228 A2 | 12/2002 |
| WO | WO 03/017177 | 2/2003 |

OTHER PUBLICATIONS

Taylor et al. "Validation of a High-Throughput Liquid Chromatograph-Tandem Mass Spectrometry Method for Urinary Cortisol and Cortisone," Clinical Chemistry (2002) vol. 48, No. 9, pp. 1511-1519.*

European Search Report for EP 04 009 709.9 dated Oct. 6, 2004.
Fleming, Cliona M. et al., "Windowed mass selection method: a new data processing algorithm for liquid chromatography-mass spectrometry data," Journal of Chromatography A, 849 (1999) 71-85.
Jain, Anil K. et al., "Statistical Pattern Recognition: A Review," IEEE Transactions on Pattern Analysis and Machine Intelligence, Vol. 22, No. 1. Jan. 2000.
Muddiman, David C. et al. "Application of sequential paired covariance to liquid chromatography-mass spectrometry data Enhancements in both the signal-to-noise ratio and the resolution of analyte peaks in the chromatogram," Journal of Chromatography A, 771 (1997) 1-7.
Norton, Scott M. et al., "Data mining of spectroscopic data for biomarker discovery," Current Opinion in Drug Discovery & Development 2001 4(3):325-331.
Windig, Willem, et al., "Fast Interpretation of complex LC/MS data using chemometrics," Analytica Chimica Acta 446 (2001) 467-476.
"Bayesian Data Analysis," by Gelman, Carlin, Stem and Rubin (2003, Chapman & Hall/CRC).
"Data Analysis: A Bayesian Tutorial," by D.S. Sivia (1996, Oxford University Press).
Gabler and Borg: Unimodalitat und Unimodalitatstests, ZUMA-Nachrichten (1996) 38, 33-44.
Dip-Test of Hartigan and Hartigan (1985), cf. P. M. Hartigan: "Computation of the Dip Statitic to Test for Unimodality"; Applied Statistics (1985) 34, 320-325.
J. A. Hartigan and P. M. Hartigan: "The Dip Test of Unimodality"; Annals of Statistics (1985) 13, 70-84.
Jacob et al, *Comparative analysis of different plant oils by high-performance liquid chromatography-atmospheric pressure chemical ionization mass spectrometry*, Journal of Chromatography A, 976, pp. 255-263 (2002).
Valcarce et al., *Chemical Characterization of Honey Bees by Curie-point Pyrolysis-Gas Chromatography-Pattern Recognition*, Chemometrics and Intelligent Laboratory Systems, 6, pp. 157-166 (1989).

* cited by examiner

*Primary Examiner*—Jerry Lin
(74) *Attorney, Agent, or Firm*—McDonnell Boehnen Hulbert & Berghoff LLP

(57) ABSTRACT

The invention provides a method for grouping measurement data obtained by effecting two or more techniques to provide characterization data characterizing at least one sample with respect to characterizing substances. According to one aspect of the invention, the grouping is effected on the basis of at least one statistical distribution of deviations ($\Delta m/z_i$) of a respective characterizing measurement value. According to another aspect of the invention, the grouping is effected on the basis of at least one collective characteristic of a plurality of respective quantitative measurement values ($I_i$).

31 Claims, 76 Drawing Sheets

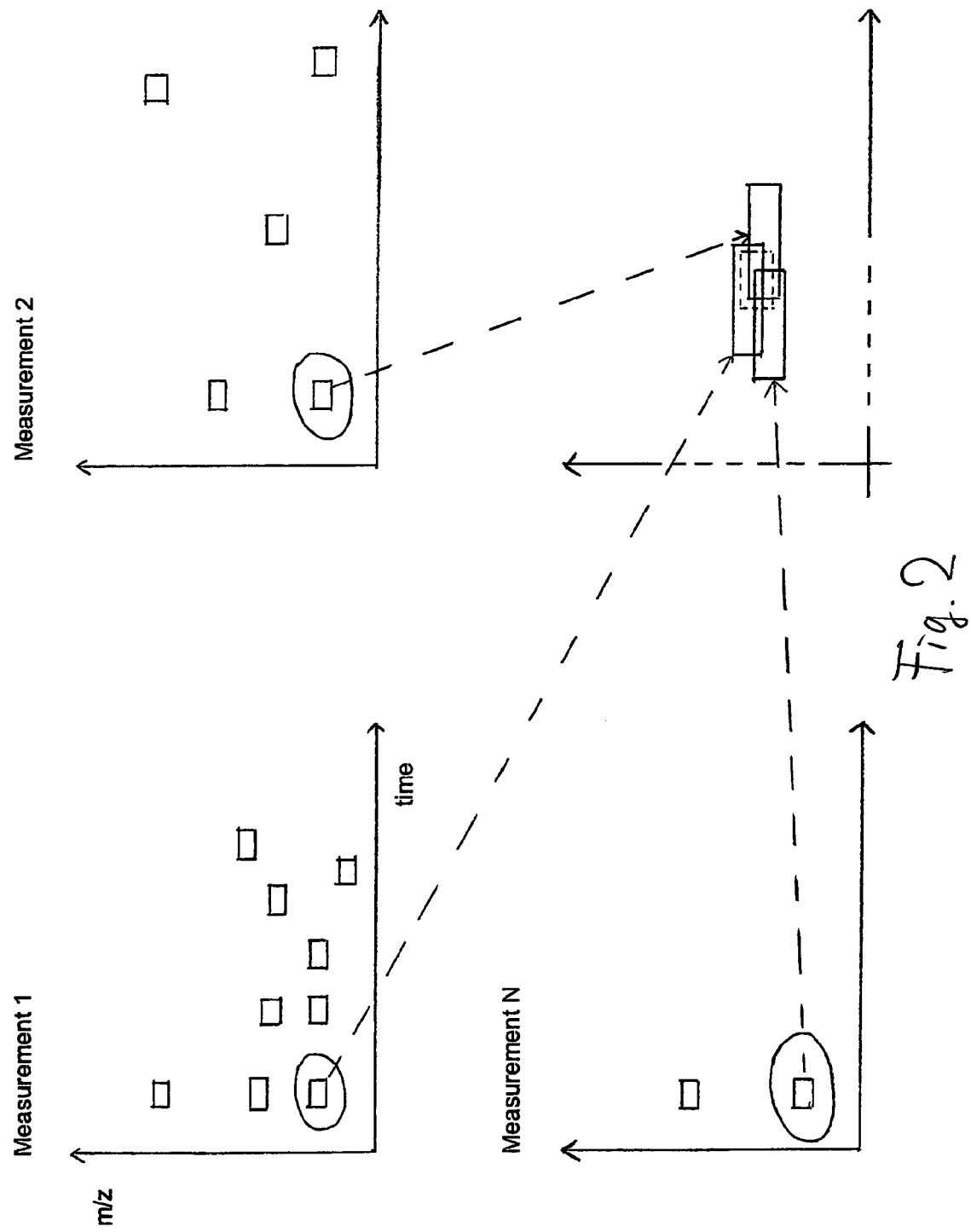

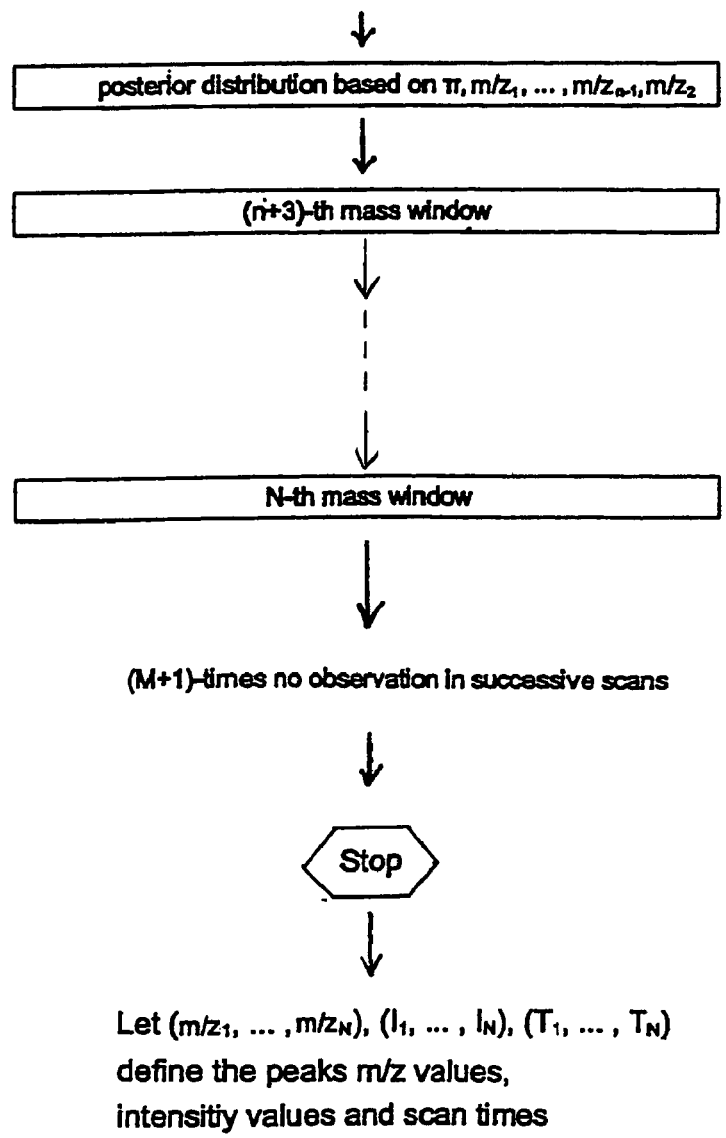
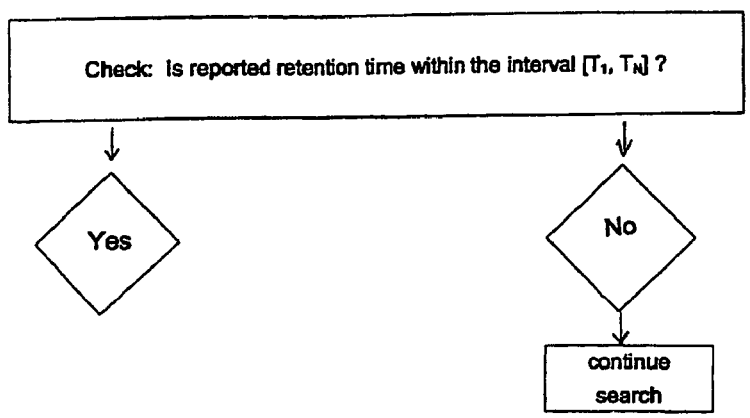
Fig. 4 c)

| Output | | |
|---|---|---|
| Peak | mass window : = | predictive (1-α)-interval based on π and (m/z$_1$, ... , m/z$_N$) |
| | time window : = | [T$_1$, T$_N$] |
| | intensity : = | sum of I$_1$, ... ; I$_N$ |
| | posterior distribution = predictive distribution for the grouping of unknown ions | |

Picture taken from Gabler and Borg, 1996

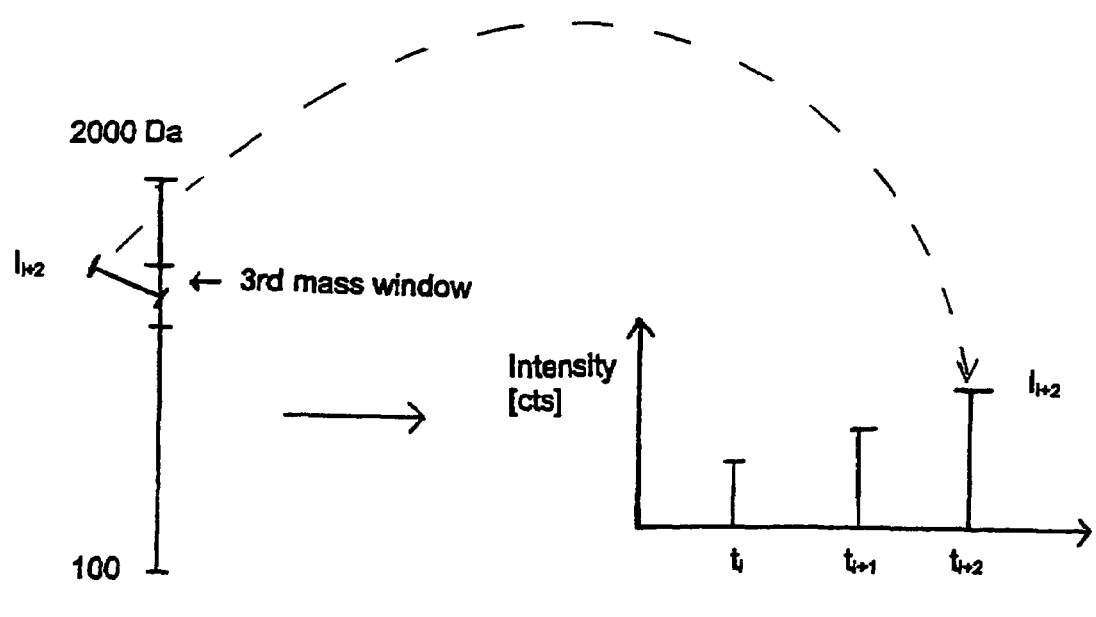
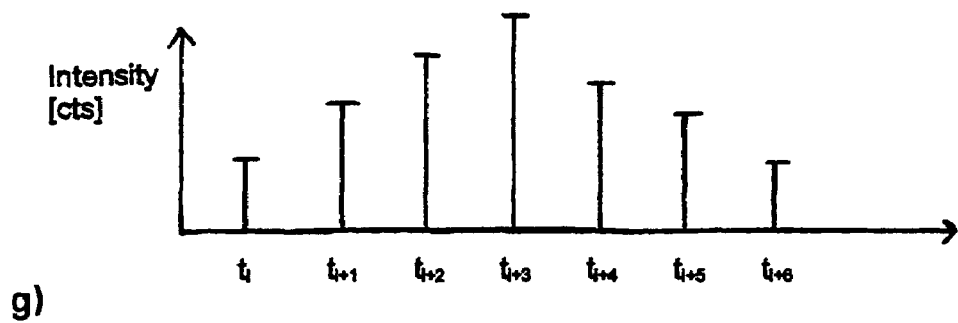
Fig. 7

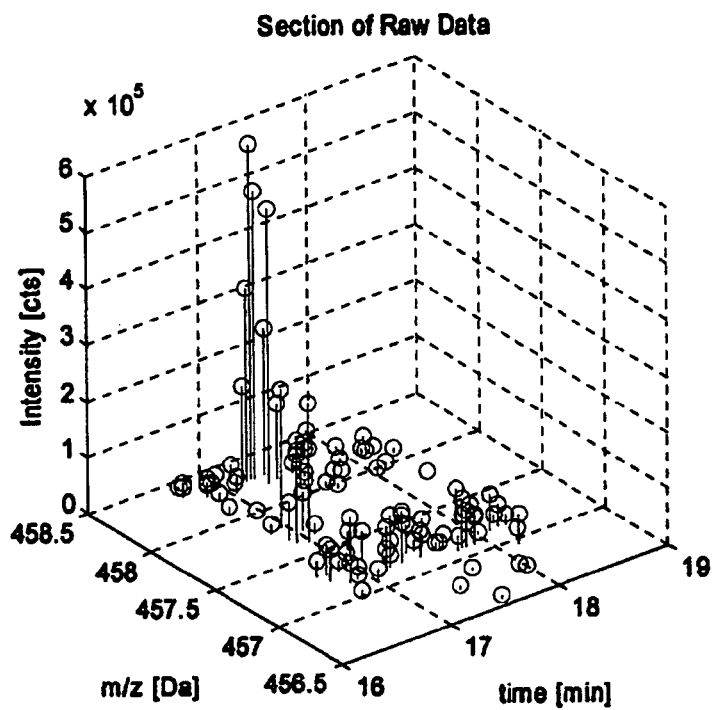
FIG. 15  Data before any processing
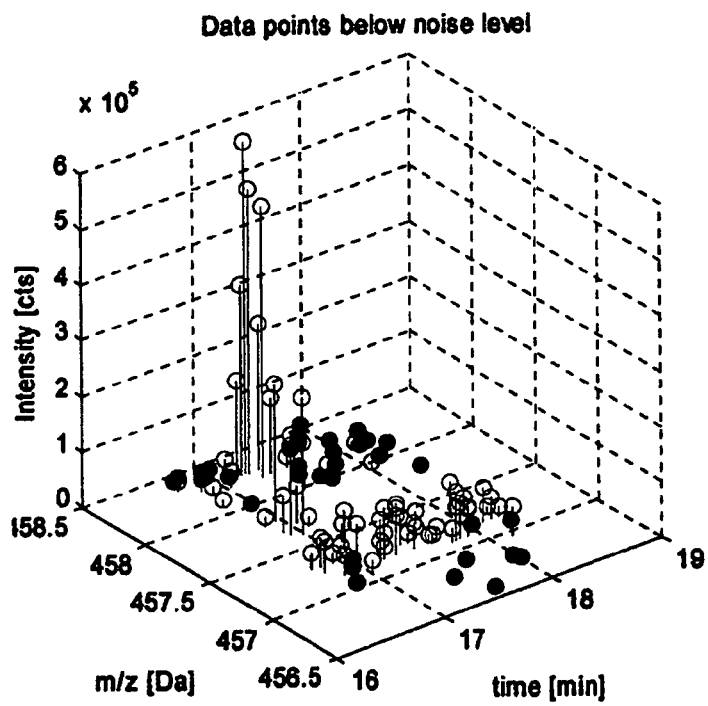
Fig. 16  Data identified as noise

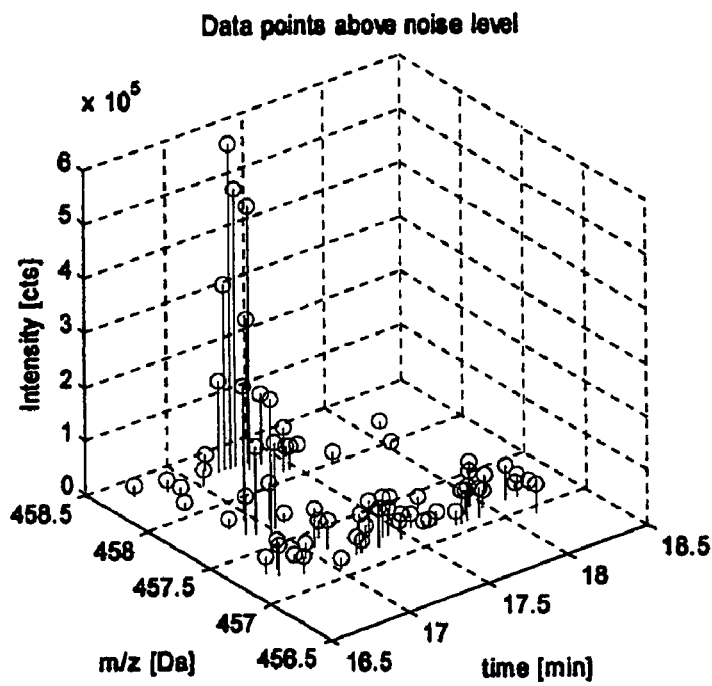
Fig. 17  Data after noise elimination
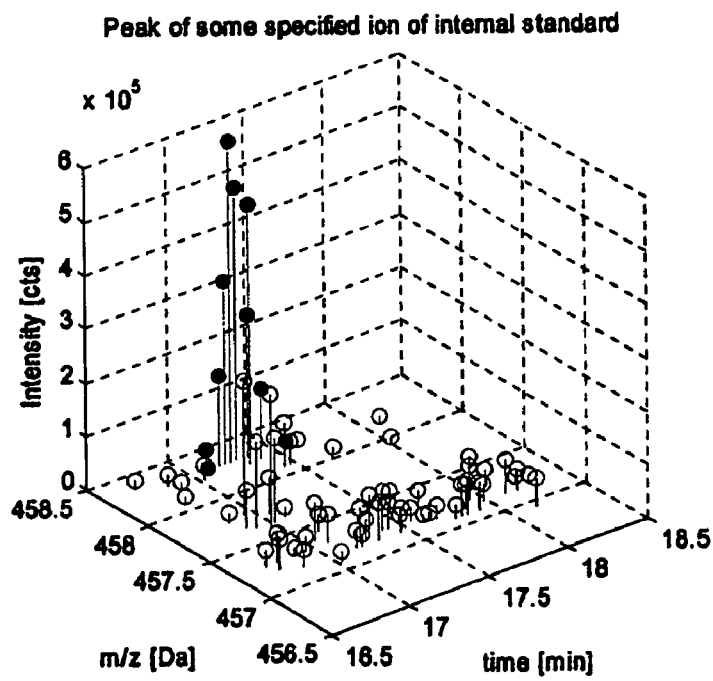
FIG. 18  These data points were identified as being caused by one of the specified ions of the internal standards. Mass error distribution is checked and leant with these points among others

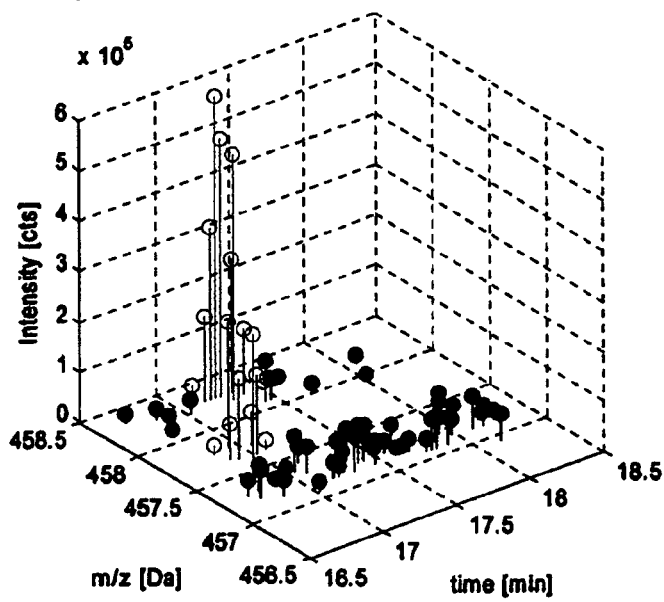

Fig. 19 The algorithm finding peaks from other ions decides for all these data points that they are not caused by some substance that went through the LC-MS process properly

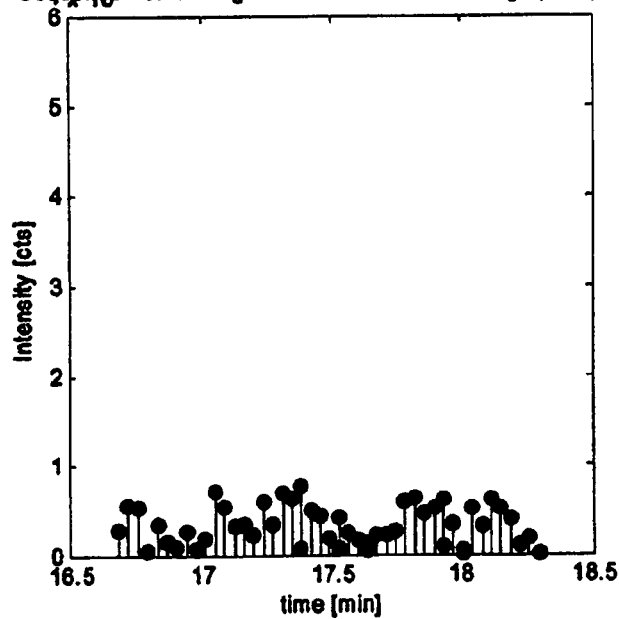

Fig. 20 This is the sequence of intensity values of the data points between 457 and 457.5 Da. Because there is no sub-sequence with a clear peak shape and of some (cumulative) considerable intensity, all these data points get thrown away.

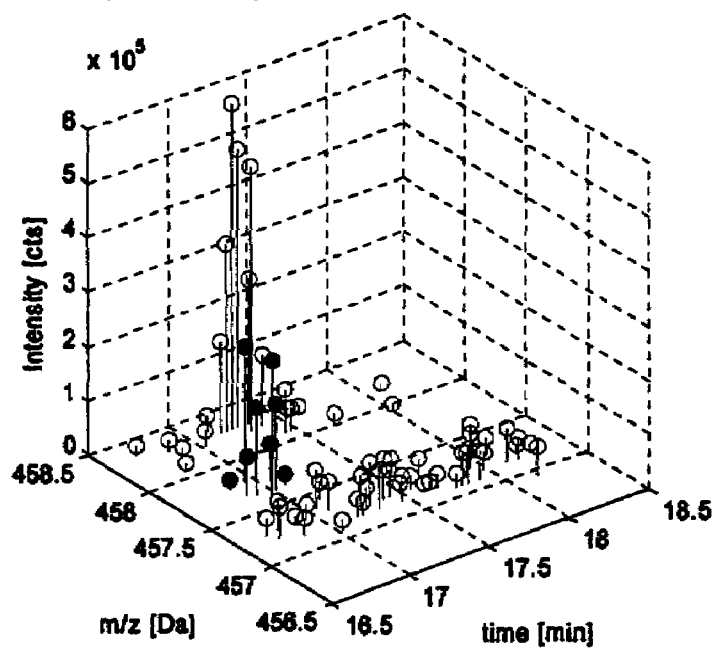
Fig. 21  These data points are identified to be caused by ions of the same type
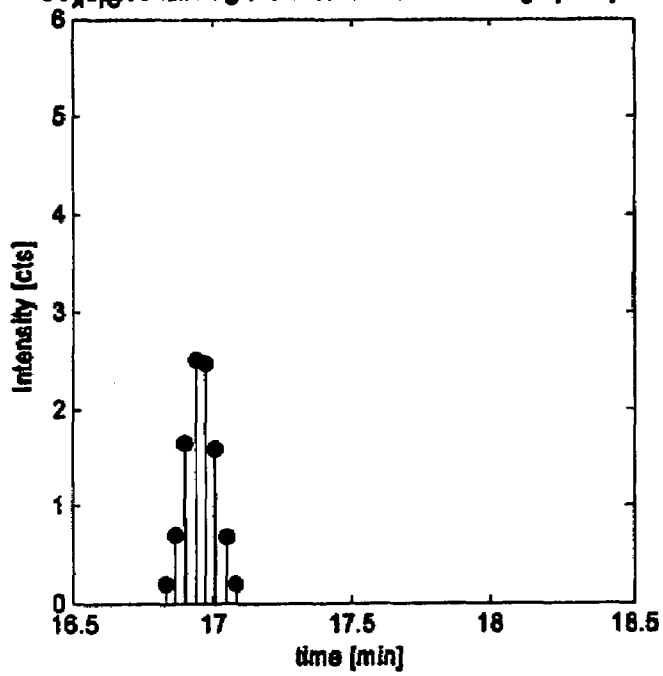
Fig. 22  The sequence of intensity values of these data points follow a clear unimodal shape

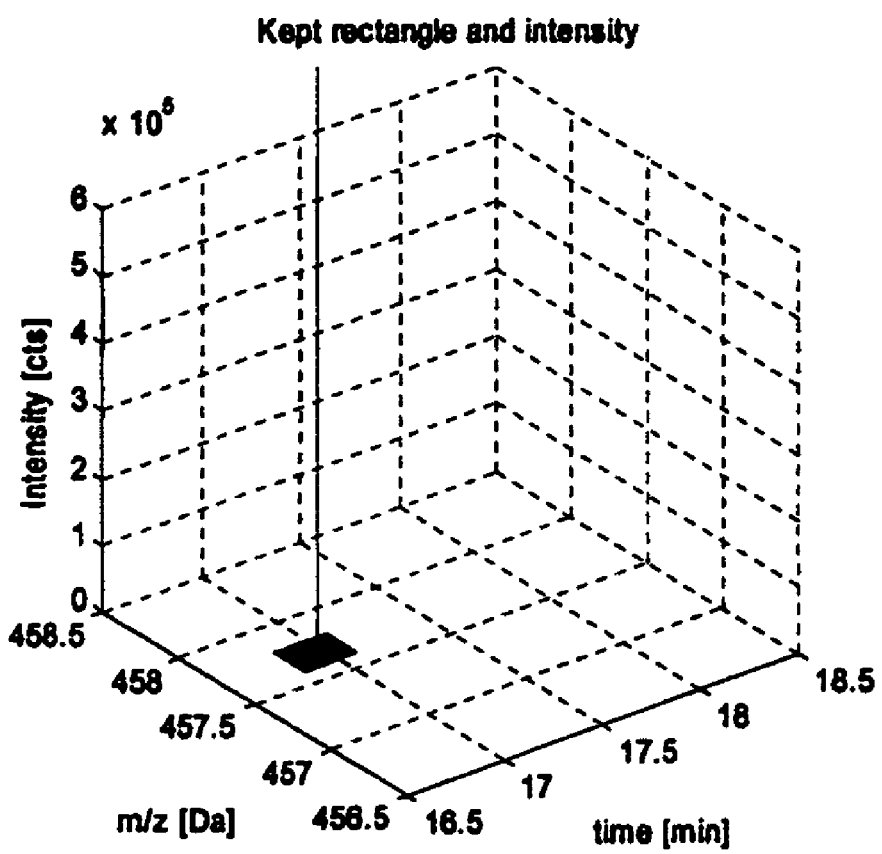
Fig. 23 The cumulative intensity and the rectangle of mass- and time window is kept as the main information about the detected ion.

b)

Grouping protocol – page 4
----------------------------------------

2. scan *(SCAN NUMBER)*

Table of observations at scan time 903.43 Seconds *(DETECTION TIME)*
in mass-to-charge window 200.00-205.00 Da Mass-to-charge: m/z [Da] *(MASS-TO-CHARGE RATIO)*
Intensity: I [cts] *(INTENSITY)*

| m/z | I | m/z | I | m/z | I | m/z | I |
|---|---|---|---|---|---|---|---|
| 200.24 | 47617 | 200.75 | 13554 | 201.27 | 18193 | 202.93 | 3867132 |

Total number of observations: 4

*Fig. 28*

Grouping protocol – page 3
----------------------------------------

Resulting potential peaks after the 1. Scan

Total number: 2

Potential peaks with 1 observation(s)
----------------------------------------
Number: 2
----------------------------------------
Position of peak: ScanIMZ2201
Course of mass-to-charge values:        201.01   ← 22
Course of intensity values:              78682
Indices of imputed values:
Predictive t-distribution:vau= 93.1, mu= 201.01, sigma2= 0.0207
Predictive 95%-mass-window: [200.72 201.30]

Position of peak: ScanIMZ2203   ← 24
Course of mass-to-charge values:        202.93
Course of intensity values:            5342784
Indices of imputed values:
Predictive t-distribution:vau= 93.1, mu= 202.93, sigma2= 0.0207
Predictive 95%-mass-window: [202.65 203.22]

23 ↙   25 ↙

Grouping protocol - page 5

```
-----------------------------------------------------------
Potential peaks that get updated because some observation
fell in their predictive mass-window for 2 scans
-----------------------------------------------------------
Listed by their identifiers and results
-----------------------------------------------------------
Scan1MZ201: Decreasing start -> no update but initialization
Scan1MZ203: Decreasing start -> no update but initialization
-----------------------------------------------------------

Resulting potential peaks after the 2. Scan
-----------------------------------------------------------
Total number: 4

-----------------------------------------------------------
Potential peaks with 1 observation(s)
-----------------------------------------------------------
Number: 4
-----------------------------------------------------------
Position of peak: Scan2MZ201
Course of mass-to-charge values:   200.75
Course of intensity values:     13554
Indices of imputed values:
Predictive t-distribution:vau= 93.1, mu= 200.75, sigma2= 0.0207
Predictive 95%-mass-window: [200.47 201.04]

Position of peak: Scan2MZ203
Course of mass-to-charge values:   202.93
Course of intensity values:   3867132
Indices of imputed values:
Predictive t-distribution:vau= 93.1, mu= 202.93, sigma2= 0.0207
Predictive 95%-mass-window: [202.65 203.22]

Position of peak: Scan2MZ200
Course of mass-to-charge values:   200.24
Course of intensity values:     47617
Indices of imputed values:
Predictive t-distribution:vau= 93.1, mu= 200.24, sigma2= 0.0207
Predictive 95%-mass-window: [199.95 200.53]

Position of peak: Scan2MZ201
Course of mass-to-charge values:   201.27
Course of intensity values:     18193
Indices of imputed values:
Predictive t-distribution:vau= 93.1, mu= 201.27, sigma2= 0.0207
Predictive 95%-mass-window: [200.98 201.55]
```

Grouping protocol - page 6

```
-----------------------------------------------------------
3. scan
-----------------------------------------------------------
Table of observations at scan time 905.53 Seconds
in mass-to-charge window 200.00-205.00 Da
-----------------------------------------------------------
Mass-to-charge: m/z [Da]
Intensity: I [cts]

m/z     I  |  m/z      I   |  m/z     I  |  m/z     I  |

201.01  31529 | 203.06  2587450 |

Total number of observations: 2
```

Fig. 29

Grouping protocol – page 7

```
---------------------------------------------------------------
Potential peaks that get updated because some observation
fell in their predictive mass-window for 2 scans
---------------------------------------------------------------
Listed by their identifiers and results Scan2MZ201: all data points were used to update (less than four)
Scan2MZ203: Decreasing start -> no update but initialization
---------------------------------------------------------------

Resulting potential peaks after the 3. Scan
---------------------------------------------------------------

Total number: 4

---------------------------------------------------------------
Potential peaks with 1 observation(s)
---------------------------------------------------------------
Number: 3

Position of peak: Scan3MZ203
Course of mass-to-charge values:      203.06
Course of intensity values:         2587450
Indices of imputed values:
Predictive t-distribution:vau= 93.1, mu= 203.06, sigma2= 0.0207
Predictive 95%-mass-window: [202.78 203.35]

Position of peak: Scan3MZ200
Course of mass-to-charge values:      200.24
Course of intensity values:            47617
Indices of imputed values:
Predictive t-distribution:vau= 93.1, mu= 200.24, sigma2= 0.0207
Predictive 95%-mass-window: [199.95 200.53]

Position of peak: Scan3MZ201
Course of mass-to-charge values:      201.27
Course of intensity values:            18193
Indices of imputed values:
Predictive t-distribution:vau= 93.1, mu= 201.27, sigma2= 0.0207
Predictive 95%-mass-window: [200.98 201.55]

---------------------------------------------------------------
Potential peaks with 2 observation(s)
---------------------------------------------------------------
Number: 1

Position of peak: Scan3MZ201
Course of mass-to-charge values:      200.75        201.01
Course of intensity values:            13554         31529
Indices of imputed values:
Predictive t-distribution:vau= 94.1, mu= 200.88, sigma2= 0.0159
Predictive 95%-mass-window: [200.63 201.13]
```

Grouping protocol – page 8

```
---------------------------------------------------------------
4. scan
---------------------------------------------------------------
Table of observations at scan time 907.63 Seconds
in mass-to-charge window 200.00-205.00 Da
---------------------------------------------------------------
Mass-to-charge: m/z [Da]
Intensity: I [cts]

m/z     I |  m/z     I |  m/z     I |  m/z     I | m/z
200.50 39862 | 200.88 83613 | 203.06 1905502 |

Total number of observations: 3
```

Fig. 30

Grouping protocol – page 9

```
-------------------------------------------------------------
Potential peaks that get updated because some observation
fell in their predictive mass-window for 2 scans
-------------------------------------------------------------
Listed by their identifiers and results Scan3MZ200: Decreasing start -> no update but initialization
Scan3MZ201: all data points were used to update (less than four)
Scan3MZ203: Decreasing start -> no update but initialization
-------------------------------------------------------------
Potential peaks that get closed because no observation
fell in their predictive mass-window for 2. scans
-------------------------------------------------------------
Listed by their identifiers and results Scan3MZ201: intensity of 18193 is smaller than required 488328
-------------------------------------------------------------
Resulting potential peaks after the 4. Scan
-------------------------------------------------------------

Total number: 3

-------------------------------------------------------------
Potential peaks with 1 observation(s)
-------------------------------------------------------------
Number: 2

Position of peak: Scan4MZ203
Course of mass-to-charge values:     203.06
Course of intensity values:    1906502
Indices of imputed values:
Predictive t-distribution:vau= 93.1, mu= 203.06, sigma2= 0.0207
Predictive 95%-mass-window: [202.78 203.35]

Position of peak: Scan4MZ200
Course of mass-to-charge values:     200.50
Course of intensity values:      39862
Indices of imputed values:
Predictive t-distribution:vau= 93.1, mu= 200.50, sigma2= 0.0207
Predictive 95%-mass-window: [200.21 200.78]

-------------------------------------------------------------
Potential peaks with 3 observation(s)
-------------------------------------------------------------
Number: 1

Position of peak: Scan4MZ201
Course of mass-to-charge values:      200.75     201.01    200.88
Course of intensity values:           13554      31529     83613
Indices of imputed values:
Predictive t-distribution:vau= 95.1, mu= 200.88, sigma2= 0.0140
Predictive 95%-mass-window: [200.65 201.12]
```

Grouping protocol – page 10

```
-------------------------------------------------------------
5. scan
-------------------------------------------------------------
Table of observations at scan time 909.73 Seconds
in mass-to-charge window 200.00-205.00 Da
-------------------------------------------------------------
Mass-to-charge: m/z [Da]
Intensity: I [cts]
-------------------------------------------------------------
m/z   I | m/z   I | m/z   I | m/z   I | m/z   I |

201.27 32903 | 202.93 1399736 |

Total number of observations: 2
```

Fig. 32

Grouping protocol – page 11

Potential peaks that get updated because some observation
fell in their predictive mass-window for 2 scans Listed by their identifiers and results Scan4MZ203: Decreasing start -> no update but initialization Resulting potential peaks after the 5. Scan Total number: 4

Potential peaks with 1 observation(s)

Number: 3

Position of peak: Scan5MZ203
Course of mass-to-charge values:      202.93
Course of intensity values:      1399736
Indices of imputed values:
Predictive t-distribution:vau= 93.1, mu= 202.93, sigma2= 0.0207
Predictive 95%-mass-window: [202.65 203.22]

Position of peak: Scan5MZ200
Course of mass-to-charge values:      200.50
Course of intensity values:       39862
Indices of imputed values:
Predictive t-distribution:vau= 93.1, mu= 200.50, sigma2= 0.0207
Predictive 95%-mass-window: [200.21 200.78]

Position of peak: Scan5MZ201
Course of mass-to-charge values:      201.27
Course of intensity values:       32903
Indices of imputed values:
Predictive t-distribution:vau= 93.1, mu= 201.27, sigma2= 0.0207
Predictive 95%-mass-window: [200.98 201.55]

Potential peaks with 3 observation(s)

Number: 1

Position of peak: Scan5MZ201
Course of mass-to-charge values:      200.75      201.01      200.88
Course of intensity values:       13554       31529       83613
Indices of imputed values:
Predictive t-distribution:vau= 95.1, mu= 200.88, sigma2= 0.0140
Predictive 95%-mass-window: [200.65 201.12]

Grouping protocol – page 12

6. scan

Table of observations at scan time 911.83 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.37 | 25053 | 201.14 | 24096 | 202.93 | 869669 | | | | |

Total number of observations: 3

Fig. 32

Grouping protocol – page 13

```
Potential peaks that get updated because some observation
fell in their predictive mass-window for 2 scans
-------------------------------------------------------------
Listed by their identifiers and results Scan5MZ200: Decreasing start -> no update but initialization
Scan5MZ201: Decreasing start -> no update but initialization
Scan5MZ203: Decreasing start -> no update but initialization
-------------------------------------------------------------
Potential peaks that get closed because no observation
fell in their predictive mass-window for 2. scans
-------------------------------------------------------------
Listed by their identifiers and results Scan5MZ201: Intensity of 13554 is smaller than required 488328
-------------------------------------------------------------
Resulting potential peaks after the 6. Scan
-------------------------------------------------------------

Total number: 3

Potential peaks with 1 observation(s)
-------------------------------------------------------------
Number: 3

Position of peak: Scan6MZ203
Course of mass-to-charge values:      202.93
Course of intensity values:           869669
Indices of imputed values:
Predictive t-distribution:vau= 93.1, mu= 202.93, sigma2= 0.0207
Predictive 95%-mass-window: [202.65 203.22]

--------
Position of peak: Scan6MZ200
Course of mass-to-charge values:      200.37
Course of intensity values:            25053
Indices of imputed values:
Predictive t-distribution:vau= 93.1, mu= 200.37, sigma2= 0.0207
Predictive 95%-mass-window: [200.08 200.65]

--------
Position of peak: Scan6MZ201
Course of mass-to-charge values:      201.14
Course of intensity values:            24096
Indices of imputed values:
Predictive t-distribution:vau= 93.1, mu= 201.14, sigma2= 0.0207
Predictive 95%-mass-window: [200.85 201.42]
```

Grouping protocol – page 14

```
7. scan
-------------------------------------------------------------
Table of observations at scan time 913.94 Seconds
in mass-to-charge window 200.00-205.00 Da
-------------------------------------------------------------
Mass-to-charge: m/z [Da]
Intensity: I [cts]
-------------------------------------------------------------
  m/z     I  |  m/z     I  |  m/z     I  |  m/z     I  |

201.27  63982 | 201.78  33749 | 203.06  415544 |

Total number of observations: 3
```

Fig. 33

Grouping protocol – page 15

Potential peaks that get updated because some observation
fell in their predictive mass-window for 2 scans listed by their identifiers and results Scan6MZ201: all data points were used to update (less than four)
Scan6MZ203: Decreasing start -> no update but initialization Resulting potential peaks after the 7. Scan Total number: 4

Potential peaks with 1 observation(s)

Number: 3

Position of peak: Scan7MZ203
Course of mass-to-charge values:      203.06
Course of intensity values:           415544
Indices of imputed values:
Predictive t-distribution: vau= 93.1, mu= 203.06, sigma2= 0.0207
Predictive 95%-mass-window: [202.78 203.35]

Position of peak: Scan7MZ200
Course of mass-to-charge values:      200.37
Course of intensity values:           25053
Indices of imputed values:
Predictive t-distribution: vau= 93.1, mu= 200.37, sigma2= 0.0207
Predictive 95%-mass-window: [200.08 200.65]

Position of peak: Scan7MZ202
Course of mass-to-charge values:      201.78
Course of intensity values:           33749
Indices of imputed values:
Predictive t-distribution: vau= 93.1, mu= 201.78, sigma2= 0.0207
Predictive 95%-mass-window: [201.49 202.07]

Potential peaks with 2 observation(s)

Number: 1

Position of peak: Scan7MZ201
Course of mass-to-charge values:      201.14      201.27
Course of intensity values:           24096       63982
Indices of imputed values:
Predictive t-distribution: vau= 94.1, mu= 201.20, sigma2= 0.0155
Predictive 95%-mass-window: [200.96 201.45]

Grouping protocol – page 16

8. scan

Table of observations at scan time 916.04 Seconds
in mass-to-charge window 200.00-205.00 Da Mass-to-charge: m/z [Da]
Intensity: I [cts]

| m/z | I | m/z | I | m/z | I | m/z | I |
|---|---|---|---|---|---|---|---|
| 200.37 | 34490 | 200.63 | 15758 | | 201.27 | 16656 | 201.78 | 55293 |
| 202.81 | 296766 | | | | | | | |

Total number of observations: 5

Fig. 34

Grouping protocol – page 17

----------------------------------------------
Potential peaks that get updated because some observation
fell in their predictive mass-window for 2 scans
----------------------------------------------
Listed by their identifiers and results Scan7M2200: all data points were used to update (less than four)
Scan7M2201: all data points were used to update (less than four)
Scan7M2202: all data points were used to update (less than four)
Scan7M2203: Decreasing start -> no update but initialization Resulting potential peaks after the 8. Scan Total number: 5

----------------------------------------------
Potential peaks with 1 observation(s)
----------------------------------------------
Number: 2
---------
Position of peak: Scan8M2203
Course of mass-to-charge values:       202.81
Course of intensity values:            296766
Indices of imputed values:
Predictive t-distribution:vau= 93.1, mu= 202.81, sigma2= 0.0207
Predictive 95%-mass-window: [202.52 203.09]

---------
Position of peak: Scan8M2201
Course of mass-to-charge values:       200.63
Course of intensity values:            15758
Indices of imputed values:
Predictive t-distribution:vau= 93.1, mu= 200.63, sigma2= 0.0207
Predictive 95%-mass-window: [200.34 200.91]

----------------------------------------------
Potential peaks with 2 observation(s)
----------------------------------------------
Number: 1
---------
Position of peak: Scan8M2202
Course of mass-to-charge values:       201.78        201.78
Course of intensity values:            33749         55293
Indices of imputed values:
Predictive t-distribution:vau= 94.1, mu= 201.78, sigma2= 0.0154
Predictive 95%-mass-window: [201.53 202.03]

----------------------------------------------
Potential peaks with 3 observation(s)
----------------------------------------------
Number: 2
---------
Position of peak: Scan8M2200
Course of mass-to-charge values:       200.37        200.37        200.37
Course of intensity values:            25053         29771         34490
Indices of imputed values: 2
Predictive t-distribution:vau= 95.1, mu= 200.37, sigma2= 0.0135
Predictive 95%-mass-window: [200.14 200.60]

---------
Position of peak: Scan8M2201

Grouping protocol – page 18

Course of mass-to-charge values:       201.14        201.27        201.27
Course of intensity values:            24096         63982         16656
Indices of imputed values:
Predictive t-distribution:vau= 95.1, mu= 201.22, sigma2= 0.0137
Predictive 95%-mass-window: [200.99 201.46]

FIG. 35

Grouping protocol – page 19
-------------------------------
9. scan

Table of observations at scan time 918.14 seconds
in mass-to-charge window 200.00-205.00 Da
-------------------------------
Mass-to-charge: m/z [Da]
Intensity: I [cts]
-------------------------------

| m/z | I | m/z | I | m/z | I | m/z | I | m/z | I |
|---|---|---|---|---|---|---|---|---|---|
| 201.27 | 27368 | 202.04 | 127314 | 202.68 | 285880 | 203.58 | 45339 | | |
| 204.09 | 70211 | 204.73 | 34040 | | | | | | |

Total number of observations: 6

Grouping protocol – page 20
-------------------------------
potential peaks that get updated because some observation
fell in their predictive mass-window for 2 scans
-------------------------------
Listed by their identifiers and results ScanSMZ201: all data points were used to update (intensity too small)
ScanSMZ203: Decreasing start -> no update but initialization
-------------------------------

Resulting potential peaks after the 9. Scan
-------------------------------
Total number: 9

-------------------------------
Potential peaks with 1 observation(s)
-------------------------------
Number: 6

Position of peak: Scan9MZ203
Course of mass-to-charge values:     202.68
Course of intensity values:          285880
Indices of imputed values:
Predictive t-distribution:vau= 93.1, mu= 202.68, sigma2= 0.0207
Predictive 95%-mass-window: [202.39 202.96]

Position of peak: Scan9MZ201
Course of mass-to-charge values:     200.63
Course of intensity values:          15758
Indices of imputed values:
Predictive t-distribution:vau= 93.1, mu= 200.63, sigma2= 0.0207
Predictive 95%-mass-window: [200.34 200.91]

Position of peak: Scan9MZ202
Course of mass-to-charge values:     202.04
Course of intensity values:          127314
Indices of imputed values:
Predictive t-distribution:vau= 93.1, mu= 202.04, sigma2= 0.0207
Predictive 95%-mass-window: [201.75 202.32]

Position of peak: Scan9MZ204
Course of mass-to-charge values:     203.58
Course of intensity values:          45339
Indices of imputed values:
Predictive t-distribution:vau= 93.1, mu= 203.58, sigma2= 0.0207
Predictive 95%-mass-window: [203.29 203.86]

Position of peak: Scan9MZ204
Course of mass-to-charge values:     204.09
Course of intensity values:          70211
Indices of imputed values:
Predictive t-distribution:vau= 93.1, mu= 204.09, sigma2= 0.0207
Predictive 95%-mass-window: [203.80 204.37]

Position of peak: Scan9MZ205
Course of mass-to-charge values:     204.73
Course of intensity values:          34040

Fig. 36

Grouping protocol – page 21

Indices of imputed values:
Predictive t-distribution:vau= 93.1, mu= 204.73, sigma2= 0.0207
Predictive 95%-mass-window: [204.45 205.02]

----------------------------------------
Potential peaks with 2 observation(s)
----------------------------------------
Number: 1
----------
Position of peak: Scan9MZ202
Course of mass-to-charge values:      201.78      201.78
Course of intensity values:           33749       55293
Indices of imputed values:
Predictive t-distribution:vau= 94.1, mu= 201.78, sigma2= 0.0154
Predictive 95%-mass-window: [201.53 202.03]

----------------------------------------
Potential peaks with 3 observation(s)
----------------------------------------
Number: 1
----------
Position of peak: Scan9MZ200
Course of mass-to-charge values:      200.37      200.37      200.37
Course of intensity values:           25053       29771       34490
Indices of imputed values: 2
Predictive t-distribution:vau= 95.1, mu= 200.37, sigma2= 0.0135
Predictive 95%-mass-window: [200.14 200.60]

----------------------------------------
Potential peaks with 4 observation(s)
----------------------------------------
Number: 1
----------
Position of peak: Scan9MZ201
Course of mass-to-charge values:      201.14      201.27      201.27      201.27
Course of intensity values:           24096       63982       16656       27368
Indices of imputed values:
Predictive t-distribution:vau= 96.1, mu= 201.23, sigma2= 0.0127
Predictive 95%-mass-window: [201.01 201.46]

Grouping protocol – page 22

----------------------------------------
10. scan

Table of observations at scan time 920.24 Seconds
in mass-to-charge window 200.00-205.00 Da
----------------------------------------
Mass-to-charge: m/z [Da]
Intensity: I [cts]

| m/z | I | m/z | I | m/z | I | m/z | I | m/z | I |
|---|---|---|---|---|---|---|---|---|---|
| 201.40 | 80970 | 203.32 | 163190 | 203.83 | 49068 | 204.73 | 227453 | | |

Total number of observations: 4

Fig. 37

Grouping protocol – page 23

------------------------------------------------------
Potential peaks that get updated because some observation
fell in their predictive mass-window for 2 scans
------------------------------------------------------
Listed by their identifiers and results Scan9MZ201: all data points were used to update (intensity too small)
Scan9MZ204: all data points were used to update (less than four)
Scan9MZ204: Decreasing start -> no update but initialization
Scan9MZ205: all data points were used to update (less than four)

------------------------------------------------------
Potential peaks that get closed because no observation
fell in their predictive mass-window for 2. scans
------------------------------------------------------
Listed by their identifiers and results Scan9MZ201: intensity of 15758 is smaller than required 488328

------------------------------------------------------
Resulting potential peaks after the 10. Scan
------------------------------------------------------

Total number: 6

---
Potential peaks with 1 observation(s)
---
Number: 3
---
Position of peak: Scan10MZ203
Course of mass-to-charge values:      202.68
Course of intensity values:      285880
Indices of imputed values:
Predictive t-distribution:vau= 93.1, mu= 202.68, sigma2= 0.0207
Predictive 95%-mass-window: [202.39 202.96]

Position of peak: Scan10MZ202
Course of mass-to-charge values:      202.04
Course of intensity values:      127314
Indices of imputed values:
Predictive t-distribution:vau= 93.1, mu= 202.04, sigma2= 0.0207
Predictive 95%-mass-window: [201.75 202.32]

Position of peak: Scan10MZ204
Course of mass-to-charge values:      203.83
Course of intensity values:       49068
Indices of imputed values:
Predictive t-distribution:vau= 93.1, mu= 203.83, sigma2= 0.0207
Predictive 95%-mass-window: [203.55 204.12]

---
Potential peaks with 2 observation(s)
---
Number: 2
---
Position of peak: Scan10MZ203
Course of mass-to-charge values:      203.58      203.32
Course of intensity values:       45339      163190
Indices of imputed values:
Predictive t-distribution:vau= 94.1, mu= 203.45, sigma2= 0.0159

Grouping protocol – page 24

Predictive 95%-mass-window: [203.20 203.70]

---
Position of peak: Scan10MZ205
Course of mass-to-charge values:      204.73      204.73
Course of intensity values:       34040      227453
Indices of imputed values:
Predictive t-distribution:vau= 94.1, mu= 204.73, sigma2= 0.0154
Predictive 95%-mass-window: [204.48 204.98]

---
Potential peaks with 5 observation(s)
---
Number: 1
---
Position of peak: Scan10MZ201
Course of mass-to-charge values:      201.14      201.27      201.27      201.27      201.27
Course of intensity values:       24096       63982       16656       27368
201.40
80970
Indices of imputed values:
Predictive t-distribution:vau= 97.1, mu= 201.27, sigma2= 0.0123
Predictive 95%-mass-window: [201.05 201.49]

Fig. 38

Grouping protocol - page 25

```
11. scan
------------------------------------------------------------------
Table of observations at scan time 922.34 Seconds
in mass-to-charge window 200.00-205.00 Da
------------------------------------------------------------------
Mass-to-charge: m/z [Da]
Intensity: I [cts]

m/z    I |   m/z    I |   m/z    I |   m/z    I |   m/z    I
 200.24 13209 | 202.04 299879 | 203.06  73414 | 204.86 166698 |

Total number of observations: 4
```

Grouping protocol - page 26

```
------------------------------------------------------------------
Potential peaks that get updated because some observation
fell in their predictive mass-window for 2 scans
------------------------------------------------------------------
Listed by their identifiers and results Scan10MZ202: all data points were used to update (less than four)
Scan10MZ205: all data points were used to update (less than four)
------------------------------------------------------------------
Potential peaks that get closed because no observation
fell in their predictive mass-window for 2. scans
------------------------------------------------------------------
Listed by their identifiers and results Scan10MZ203: intensity of 285880 is smaller than required 488328
------------------------------------------------------------------
Resulting potential peaks after the 11. Scan
------------------------------------------------------------------
Total number: 7
------------------------------------------------------------------
Potential peaks with 1 observation(s)
------------------------------------------------------------------
Number: 3
------------------------------------------------------------------
Position of peak: Scan1MZ204
Course of mass-to-charge values:              203.83
Course of intensity values:            49068
Indices of imputed values:
Predictive t-distribution:vau= 93.1, mu= 203.83, sigma2= 0.0207
Predictive 95%-mass-window: [203.55 204.12]

Position of peak: Scan1MZ200
Course of mass-to-charge values:              200.24
Course of intensity values:            13209
Indices of imputed values:
Predictive t-distribution:vau= 93.1, mu= 200.24, sigma2= 0.0207
Predictive 95%-mass-window: [199.95 200.53]

Position of peak: Scan11MZ203
Course of mass-to-charge values:              203.06
Course of intensity values:            73414
Indices of imputed values:
Predictive t-distribution:vau= 93.1, mu= 203.06, sigma2= 0.0207
Predictive 95%-mass-window: [202.78 203.35]
------------------------------------------------------------------
Potential peaks with 2 observation(s)
------------------------------------------------------------------
Number: 1
------------------------------------------------------------------
Position of peak: Scan11MZ203
Course of mass-to-charge values:              203.58    203.32
Course of intensity values:            45339    163190
Indices of imputed values:
Predictive t-distribution:vau= 94.1, mu= 203.45, sigma2= 0.0159
Predictive 95%-mass-window: [203.20 203.70]
------------------------------------------------------------------
```

Fig. 39

Grouping protocol - page 27

Potential peaks with 3 observation(s)
--------
Number: 2
--------
Position of peak: Scan1MZ202
Course of mass-to-charge values:      202.04      202.04      202.04
Course of intensity values:           127314      213596      299879
Indices of imputed values: 2
Predictive t-distribution:vau= 95.1, mu= 202.04, sigma2= 0.0135
Predictive 95%-mass-window: [201.81 202.27]

↑ Position of peak: Scan1MZ205
Course of mass-to-charge values:      204.73      204.73      204.86
Course of intensity values:           34040       227453      166698
Indices of imputed values:
Predictive t-distribution:vau= 95.1, mu= 204.77, sigma2= 0.0137
Predictive 95%-mass-window: [204.54 205.01]

--------
Potential peaks with 5 observation(s)
--------
Number: 1
--------
Position of peak: Scan1MZ201
Course of mass-to-charge values:      201.14      201.27      201.27      201.27      201.27
201.40
Course of intensity values:           24096       63982       16656       27368
80970

Indices of imputed values:
Predictive t-distribution:vau= 97.1, mu= 201.27, sigma2= 0.0123
Predictive 95%-mass-window: [201.05 201.49]

Grouping protocol - page 28
--------
12. scan
--------
Table of observations at scan time 924.44 Seconds
in mass-to-charge window 200.00-205.00 Da
--------
Mass-to-charge: m/z [Da]
Intensity: I [cts]

| m/z | I | m/z | I | m/z | I | m/z | I | m/z | I |
|---|---|---|---|---|---|---|---|---|---|
| 201.14 | 37810 | 201.52 | 78404 | 202.29 | 236389 | 204.09 | 50608 |
| 204.86 | 215617 | | | | | | | | |

Total number of observations: 5

Fig. 40

Grouping protocol – page 29

```
------------------------------------------------------------
Potential peaks that get updated because some observation
fell in their predictive mass-window for 2 scans
------------------------------------------------------------
Listed by their identifiers and results Scan1MZ201: all data points were used to update (intensity too small)
Scan1MZ204: all data points were used to update (less than four)
Scan1MZ205: all data points were used to update (intensity too small)

------------------------------------------------------------
Potential peaks that get closed because no observation
fell in their predictive mass-window for 2. scans
------------------------------------------------------------
Listed by their identifiers and results Scan1MZ203: intensity of 45339 is smaller than required 488328

------------------------------------------------------------
Resulting potential peaks after the 12. Scan
------------------------------------------------------------

Total number: 8

------------------------------------------------------------
Potential peaks with 1 observation(s)
------------------------------------------------------------
Number: 4

Position of peak: Scan12MZ200
Course of mass-to-charge values:     200.24
Course of intensity values:          13209
Indices of imputed values:
Predictive t-distribution:vau= 93.1, mu= 200.24, sigma2= 0.0207
Predictive 95%-mass-window: (199.95 200.53]

Position of peak: Scan12MZ203
Course of mass-to-charge values:     203.06
Course of intensity values:          73414
Indices of imputed values:
Predictive t-distribution:vau= 93.1, mu= 203.06, sigma2= 0.0207
Predictive 95%-mass-window: [202.78 203.35]

Position of peak: Scan12MZ202
Course of mass-to-charge values:     201.52
Course of intensity values:          78404
Indices of imputed values:
Predictive t-distribution:vau= 93.1, mu= 201.52, sigma2= 0.0207
Predictive 95%-mass-window: [201.24 201.81]

Position of peak: Scan12MZ202
Course of mass-to-charge values:     202.29
Course of intensity values:          236389
Indices of imputed values:
Predictive t-distribution:vau= 93.1, mu= 202.29, sigma2= 0.0207
Predictive 95%-mass-window: [202.01 202.58]

------------------------------------------------------------
Potential peaks with 3 observation(s)
------------------------------------------------------------
Number: 2
```

Grouping protocol – page 30

```
Position of peak: Scan12MZ202
Course of mass-to-charge values:       202.04      202.04      202.04
Course of intensity values:            127314      213596      299879
Indices of imputed values: 2
Predictive t-distribution:vau= 95.1, mu= 202.04, sigma2= 0.0135
Predictive 95%-mass-window: [201.81 202.27]

Position of peak: Scan12MZ204
Course of mass-to-charge values:       203.83      203.83      204.09
Course of intensity values:            49068       49838       50608
Indices of imputed values: 2
Predictive t-distribution:vau= 95.1, mu= 203.92, sigma2= 0.0141
Predictive 95%-mass-window: [203.68 204.15]

------------------------------------------------------------
Potential peaks with 4 observation(s)
------------------------------------------------------------
Number: 1

Position of peak: Scan12MZ205
Course of mass-to-charge values:       204.73     204.73     204.86     204.86
Course of intensity values:            34040      227453     166698     215617
Indices of imputed values:
Predictive t-distribution:vau= 96.1, mu= 204.79, sigma2= 0.0127
Predictive 95%-mass-window: [204.57 205.02]

------------------------------------------------------------
Potential peaks with 7 observation(s)
------------------------------------------------------------
Number: 1

Position of peak: Scan12MZ201
Course of mass-to-charge values:       201.14      201.27      201.27      201.27      201.27
201.40     201.27      201.14
Course of intensity values:            24096       63982       16656       27368
80970      59390       37810
Indices of imputed values: 6
Predictive t-distribution:vau= 99.1, mu= 201.25, sigma2= 0.0117
Predictive 95%-mass-window: [201.03 201.46]
```

Fig. 41

Grouping protocol – page 31

13. scan

Table of observations at scan time 926.54 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.24 | 28307 | 200.88 | 98661 | 201.65 | 23321 | 202.93 | 137722 | | |
| 204.86 | 401424 | | | | | | | | |

Total number of observations: 5

Grouping protocol – page 32

Potential peaks that got updated because some observation
fell in their predictive mass-window for 2 scans Listed by their identifiers and results Scan12MZ200: all data points were used to update (less than four)
Scan12MZ202: Decreasing start -> no update but initialization
Scan12MZ203: all data points were used to update (less than four)
Scan12MZ205: all data points were used to update (intensity too small)

Potential peaks that got closed because no observation
fell in their predictive mass-window for 2. scans Listed by their identifiers and results Scan12MZ202: intensity of 127314 is smaller than required 485489

Resulting potential peaks after the 13. Scan

Total number: 8

Potential peaks with 1 observation(s)

Number: 3

Position of peak: Scan13MZ202
Course of mass-to-charge values:       201.65
Course of intensity values:             23321
Indices of imputed values:
Predictive t-distribution:vau= 93.1, mu= 201.65, sigma2= 0.0207
Predictive 95%-mass-window: [201.37 201.94]

Position of peak: Scan13MZ202
Course of mass-to-charge values:       202.29
Course of intensity values:            236389
Indices of imputed values:
Predictive t-distribution:vau= 93.1, mu= 202.29, sigma2= 0.0207
Predictive 95%-mass-window: [202.01 202.58]

Position of peak: Scan13MZ201
Course of mass-to-charge values:       200.88
Course of intensity values:             98661
Indices of imputed values:
Predictive t-distribution:vau= 93.1, mu= 200.88, sigma2= 0.0207
Predictive 95%-mass-window: [200.60 201.17]

Potential peaks with 3 observation(s)

Number: 3

Position of peak: Scan13MZ204
Course of mass-to-charge values:    203.83    203.83    204.09
Course of intensity values:          49068     49838     50608
Indices of imputed values: 2
Predictive t-distribution:vau= 95.1, mu= 203.92, sigma2= 0.0141

Fig. 42

Grouping protocol – page 33

Predictive 95%-mass-window: [203.68 204.15]

------------------------------------------
Position of peak: Scan13MZ200
Course of mass-to-charge values:    200.24    200.24    200.24
Course of intensity values:         13209     20758     28307
Indices of imputed values: 2
Predictive t-distribution:vau= 95.1, mu= 200.24, sigma2= 0.0135
Predictive 95%-mass-window: [200.01 200.47]

Position of peak: Scan13MZ203
Course of mass-to-charge values:    203.06    203.06    202.93
Course of intensity values:         73414     105568    137722
Indices of imputed values: 2
Predictive t-distribution:vau= 95.1, mu= 203.02, sigma2= 0.0137
Predictive 95%-mass-window: [202.79 203.25]

------------------------------------------
Potential peaks with 5 observation(s)
------------------------------------------
Number: 1
↑ Position of peak: Scan13MZ205
   Course of mass-to-charge values:    204.73    204.86    204.86
204.86
Course of intensity values:         34040     227453    166698    215617
401424
Indices of imputed values:
Predictive t-distribution:vau= 97.1, mu= 204.81, sigma2= 0.0122
Predictive 95%-mass-window: [204.59 205.03]

------------------------------------------
Potential peaks with 7 observation(s)
------------------------------------------
Number: 1
Position of peak: Scan13MZ201
Course of mass-to-charge values:    201.14    201.27    201.27    201.27
201.40    201.27    201.14
Course of intensity values:         24096     63982     16656     27358
80970     59390     37810
Indices of imputed values: 6
Predictive t-distribution:vau= 99.1, mu= 201.25, sigma2= 0.0117
Predictive 95%-mass-window: [201.03 201.46]

Grouping protocol – page 34

------------------------------------------
14. scan

Table of observations at scan time 928.64 Seconds
in mass-to-charge window 200.00-205.00 Da Mass-to-charge: m/z [Da]
Intensity: I [cts]
------------------------------------------
m/z     I | m/z     I | m/z     I | m/z     I |

201.14  66886 | 202.81  41128 | 204.99  455769 |

Total number of observations: 3

Fig. 43

```
Grouping protocol - page 35
------------------------------------------------------------
Potential peaks that get updated because some observation
fell in their predictive mass-window for 2 scans
------------------------------------------------------------
Listed by their identifiers and results Scan13MZ201: all data points were used to update (intensity too small)
Scan13MZ203: all data points were used to update (intensity too small)
Scan13MZ205: all data points were used to update (intensity too small)
------------------------------------------------------------
Potential peaks that get closed because no observation
fell in their predictive mass-window for 2. scans
------------------------------------------------------------
Listed by their identifiers and results Scan13MZ202: intensity of 236389 is smaller than required 485489
------------------------------------------------------------
Resulting potential peaks after the 14. Scan Total number: 6
------------------------------------------------------------
Potential peaks with 1 observation(s)
------------------------------------------------------------
Number: 2
------------------------------------------------------------
Position of peak: Scan14MZ202
Course of mass-to-charge values:   201.65
Course of intensity values:        23321
Indices of imputed values:
Predictive t-distribution:vau= 93.1, mu= 201.65, sigma2= 0.0207
Predictive 95%-mass-window: [201.37 201.94]
------------------------------------------------------------
Position of peak: Scan14MZ201
Course of mass-to-charge values:   200.88
Course of intensity values:        98661
Indices of imputed values:
Predictive t-distribution:vau= 93.1, mu= 200.88, sigma2= 0.0207
Predictive 95%-mass-window: [200.60 201.17]
------------------------------------------------------------
Potential peaks with 3 observation(s)
------------------------------------------------------------
Number: 1
------------------------------------------------------------
Position of peak: Scan14MZ200
Course of mass-to-charge values:   200.24    200.24    200.24
Course of intensity values:        13209     20758     28307
Indices of imputed values: 2
Predictive t-distribution:vau= 95.1, mu= 200.24, sigma2= 0.0135
Predictive 95%-mass-window: [200.01 200.47]
------------------------------------------------------------
Potential peaks with 4 observation(s)
------------------------------------------------------------
Number: 1
------------------------------------------------------------
Position of peak: Scan14MZ203
```

```
Grouping protocol - page 36

Course of mass-to-charge values:   203.06    203.06    202.93    202.81
Course of intensity values:        73414     105568    137722    41128
Indices of imputed values: 2
Predictive t-distribution:vau= 96.1, mu= 202.97, sigma2= 0.0131
Predictive 95%-mass-window: [202.74 203.19]
------------------------------------------------------------
Potential peaks with 6 observation(s)
------------------------------------------------------------
Number: 1
------------------------------------------------------------
Position of peak: Scan14MZ205
Course of mass-to-charge values:   204.73    204.73    204.86    204.86
204.86    204.99
Course of intensity values:        34040     227453    166698    215617
401424    455769
Indices of imputed values:
Predictive t-distribution:vau= 98.1, mu= 204.84, sigma2= 0.0120
Predictive 95%-mass-window: [204.62 205.06]
------------------------------------------------------------
Potential peaks with 9 observation(s)
------------------------------------------------------------
Number: 1
------------------------------------------------------------
Position of peak: Scan14MZ201
Course of mass-to-charge values:   201.14    201.27    201.27
201.40    201.27    201.14    201.25    201.14    201.27
Course of intensity values:        24096     63982     16656     27360
80970     59390     37810     52348     66886
Indices of imputed values: 6 8
Predictive t-distribution:vau= 101.1, mu= 201.24, sigma2= 0.0112
Predictive 95%-mass-window: [201.03 201.45]
```

Fig. 44

Grouping protocol – page 37

15. scan

Table of observations at scan time 930.74 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.88 | 141407 | 202.42 | 206407 | 204.99 | 456323 | | | | |

Total number of observations: 3

Grouping protocol – page 38

Potential peaks that get updated because some observation
fell in their predictive mass-window for 2 scans
------------------------------------------------------------
Listed by their identifiers and results
------------------------------------------------------------
Scan14M2201: all data points were used to update (less than four)
Scan14M2205: all data points were used to update (intensity too small)

Potential peaks that get closed because no observation
fell in their predictive mass-window for 2 scans
------------------------------------------------------------
Listed by their identifiers and results
------------------------------------------------------------
Scan14M2202: intensity of 23321 is smaller than required 485489

Resulting potential peaks after the 15. Scan

Total number: 5

Potential peaks with 1 observation(s)
------------------------------------------------------------
Number: 1
------------------------------------------------------------
Position of peak: Scan15M2202
Course of mass-to-charge values:     202.42
Course of intensity values:          206407
Indices of imputed values:
Predictive t-distribution: vau= 93.1, mu= 202.42, sigma2= 0.0207
Predictive 95%-mass-window: [202.14 202.71]

Potential peaks with 3 observation(s)
------------------------------------------------------------
Number: 1
------------------------------------------------------------
Position of peak: Scan15M2201
Course of mass-to-charge values:    200.88    200.88    200.88
Course of intensity values:          98661    120034    141407
Indices of imputed values: 2
Predictive t-distribution: vau= 95.1, mu= 200.88, sigma2= 0.0135
Predictive 95%-mass-window: [200.65 201.11]

Potential peaks with 4 observation(s)
------------------------------------------------------------
Number: 1
------------------------------------------------------------
Position of peak: Scan15M2203
Course of mass-to-charge values:    203.06    203.06    202.93    202.81
Course of intensity values:          73414    105568    137722    41128
Indices of imputed values: 2
Predictive t-distribution: vau= 96.1, mu= 202.97, sigma2= 0.0131
Predictive 95%-mass-window: [202.74 203.19]

Potential peaks with 7 observation(s)
------------------------------------------------------------
Number: 1
------------------------------------------------------------

Fig. 45

Grouping protocol - page 39

→ Position of peak: Scan15MZ205
Course of mass-to-charge values:
204.86   204.99   204.99   204.73   204.73   204.86   204.86
Course of intensity values:
401424   455769   456323   34040   227453   166698   215617
Indices of imputed values:
Predictive t-distribution:vau= 99.1, mu= 204.86, sigma2= 0.0119
Predictive 95%-mass-window: [204.64 205.08]

---

Potential peaks with 9 observation(s)

---

Number: 1

---

Position of peak: Scan15MZ201
Course of mass-to-charge values:
201.40   201.27   201.14   201.14   201.25   201.27   201.14   201.27   201.27
Course of intensity values:
80970   59390   37810   24096   63982   16656   27368
            52348   66886
Indices of imputed values: 6 8
Predictive t-distribution:vau= 101.1, mu= 201.24, sigma2= 0.0112
Predictive 95%-mass-window: [201.03 201.45]

Grouping protocol - page 40

---

16. scan

---

Table of observations at scan time 932.84 Seconds
in mass-to-charge window 200.00-205.00 Da

---

Mass-to-charge: m/z [Da]
Intensity: I [cts]

---

| m/z | I | m/z | I | m/z | I | m/z | I | m/z | I |
|---|---|---|---|---|---|---|---|---|---|
| 201.01 | 73167 | 202.04 | 248143 | 203.06 | 74652 | 204.99 | 868147 | | |

Total number of observations: 4

Fig. 46

Grouping protocol – page 41

---------------------------------------------------------------
Potential peaks that get updated because some observation
fell in their predictive mass-window for 2 scans
---------------------------------------------------------------
Listed by their identifiers and results Scan15MZ201: all data points were used to update (intensity too small)
Scan15MZ203: all data points were used to update (intensity too small)
Scan15MZ205: all data points were used to update (intensity too small)

---------------------------------------------------------------
Potential peaks that get closed because no observation
fell in their predictive mass-window for 2. scans
---------------------------------------------------------------
Listed by their identifiers and results Scan15MZ201: intensity of 109197 is smaller than required 488328

---------------------------------------------------------------
Resulting potential peaks after the 16. Scan
---------------------------------------------------------------

Total number: 5

---------------------------------------------------------------
Potential peaks with 1 observation(s)
---------------------------------------------------------------
Number: 2
---------
Position of peak: Scan16MZ202
Course of mass-to-charge values:    202.42
Course of intensity values:         205407
Indices of imputed values:
Predictive t-distribution:vau= 93.1, mu= 202.42, sigma2= 0.0207
Predictive 95%-mass-window: [202.14 202.71]
---------
Position of peak: Scan16MZ202
Course of mass-to-charge values:    202.04
Course of intensity values:         248143
Indices of imputed values:
Predictive t-distribution:vau= 93.1, mu= 202.04, sigma2= 0.0207
Predictive 95%-mass-window: [201.75 202.32]

---------------------------------------------------------------
Potential peaks with 4 observation(s)
---------------------------------------------------------------
Number: 1
---------
Position of peak: Scan16MZ201
Course of mass-to-charge values:    200.88   200.88   200.88   201.01
Course of intensity values:         98661   120034   141407    73167
Indices of imputed values: 2
Predictive t-distribution:vau= 96.1, mu= 200.91, sigma2= 0.0127
Predictive 95%-mass-window: [200.69 201.14]

---------------------------------------------------------------
Potential peaks with 6 observation(s)
---------------------------------------------------------------
Number: 1
---------
Position of peak: Scan16MZ203
Course of mass-to-charge values:    203.06   203.06   202.93   202.81
202.97   203.06

Grouping protocol – page 42

Course of intensity values:         73414   105568   137722    41128
57890    74652
Indices of imputed values: 2 5
Predictive t-distribution:vau= 98.1, mu= 202.98, sigma2= 0.0121
Predictive 95%-mass-window: [202.76 203.20]

---------------------------------------------------------------
Potential peaks with 8 observation(s)
---------------------------------------------------------------
Number: 1
---------
→ Position of peak: Scan16MZ205 ←
Course of mass-to-charge values:            204.73   204.73   204.86   204.86
204.86   204.99   204.99
Course of intensity values:                 34040   227453   166698   215617
401424   455769   456323   868147
Indices of imputed values:
Predictive t-distribution:vau= 100.1, mu= 204.88, sigma2= 0.0117
Predictive 95%-mass-window: [204.66 205.09]

Fig. 47

Grouping protocol – page 43

17. scan

Table of observations at scan time 934.94 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.88 | 71974 | 201.14 | 72472 | 201.91 | 220342 | 202.68 | 63600 | | |
| 203.06 | 54154 | 204.99 | 949309 | | | | | | |

Total number of observations: 6

Grouping protocol – page 44

Potential peaks that get updated because some observation
fell in their predictive mass-window for 2 scans Listed by their identifiers and results Scan16MZ201: all data points were used to update (intensity too small)
Scan16MZ202: Decreasing start -> no update but initialization
Scan16MZ202: Decreasing start -> no update but initialization
Scan16MZ203: all data points were used to update (intensity too small)
Scan16MZ205: all data points were used to update (intensity too small)

Resulting potential peaks after the 17. Scan

Total number: 6

Potential peaks with 1 observation(s)

Number: 3

Position of peak: Scan17MZ203
Course of mass-to-charge values:    202.68
Course of intensity values:         63600
Indices of imputed values:
Predictive t-distribution:vau= 93.1, mu= 202.68, sigma2= 0.0207
Predictive 95%-mass-window: [202.39 202.96]

Position of peak: Scan17MZ202
Course of mass-to-charge values:    201.91
Course of intensity values:         220342
Indices of imputed values:
Predictive t-distribution:vau= 93.1, mu= 201.91, sigma2= 0.0207
Predictive 95%-mass-window: [201.62 202.19]

Position of peak: Scan17MZ201
Course of mass-to-charge values:    201.14
Course of intensity values:         72472
Indices of imputed values:
Predictive t-distribution:vau= 93.1, mu= 201.14, sigma2= 0.0207
Predictive 95%-mass-window: [200.85 201.42]

Potential peaks with 5 observation(s)

Number: 1

Position of peak: Scan17MZ201
Course of mass-to-charge values:   200.88   200.88   200.88   200.88   201.01
200.88
Course of intensity values:        98661    120034   141407   73167
71974
Indices of imputed values: 2
Predictive t-distribution:vau= 97.1, mu= 200.91, sigma2= 0.0121
Predictive 95%-mass-window: [200.69 201.13]

Potential peaks with 7 observation(s)

Grouping protocol – page 45

Number: 1
--------
Position of peak: Scan17M2203
Course of mass-to-charge values:
202.97    203.06    203.06    203.06    202.93    202.81
Course of intensity values:
57890    74652    54154    73414    105568    137722    41128
Indices of imputed values: 2 5
Predictive t-distribution:vau= 99.1, mu= 202.99, sigma2= 0.0118
Predictive 95%-mass-window: [202.78 203.21]

Potential peaks with 9 observation(s)
--------
Number: 1
--------
→ Position of peak: Scan17M2205
Course of mass-to-charge values:
204.86    204.99    204.99    204.73    204.73    204.99    204.86    204.86
204.99    204.99    34040    227453    166698    215617
401424    455769    456323    868147    949309
Indices of imputed values:
Predictive t-distribution:vau= 101.1, mu= 204.89, sigma2= 0.0116
Predictive 95%-mass-window: [204.67 205.10]

Grouping protocol – page 46

18. scan
--------
Table of observations at scan time 937.05 seconds
in mass-to-charge window 200.00-205.00 Da
--------
Mass-to-charge: m/z [Da]
Intensity: I [cts]
--------

| m/z | I | m/z | I | m/z | I | m/z | I | m/z | I |
|---|---|---|---|---|---|---|---|---|---|
| 200.88 | 132145 | 202.29 | 76847 | 203.06 | 61095 | 204.86 | 1054378 |

Total number of observations: 4

Grouping protocol – page 47

```
Potential peaks that get updated because some observation
fell in their predictive mass-window for 2 scans Listed by their identifiers and results Scan17MZ201: all data points were used to update (intensity too small)
Scan17MZ203: all data points were used to update (intensity too small)
Scan17MZ205: all data points were used to update (intensity too small)

Resulting potential peaks after the 18. Scan

Total number: 7

----------------------------
Potential peaks with 1 observation(s)
----------------------------
Number: 4
----------------------------
Position of peak: Scan18MZ203
Course of mass-to-charge values:             202.68
Course of intensity values:                  63600
Indices of imputed values:
Predictive t-distribution:vau= 93.1, mu= 202.68, sigma2= 0.0207
Predictive 95%-mass-window: [202.39 202.96]
----------------------------
Position of peak: Scan18MZ202
Course of mass-to-charge values:             201.91
Course of intensity values:                  220342
Indices of imputed values:
Predictive t-distribution:vau= 93.1, mu= 201.91, sigma2= 0.0207
Predictive 95%-mass-window: [201.62 202.19]
----------------------------
Position of peak: Scan18MZ201
Course of mass-to-charge values:             201.14
Course of intensity values:                  72472
Indices of imputed values:
Predictive t-distribution:vau= 93.1, mu= 201.14, sigma2= 0.0207
Predictive 95%-mass-window: [200.85 201.42]
----------------------------
Position of peak: Scan18MZ202
Course of mass-to-charge values:             202.29
Course of intensity values:                  76847
Indices of imputed values:
Predictive t-distribution:vau= 93.1, mu= 202.29, sigma2= 0.0207
Predictive 95%-mass-window: [202.01 202.58]
----------------------------
Potential peaks with 6 observation(s)
----------------------------
Number: 1
----------------------------
Position of peak: Scan18MZ201
Course of mass-to-charge values:    200.88  200.88  200.88  200.88  200.88  201.01
200.88  200.88
Course of intensity values:         98661  120034  141407  73167
71974   132145
Indices of imputed values: 2
```

Grouping protocol – page 48

```
Predictive t-distribution:vau= 98.1, mu= 200.90, sigma2= 0.0116
Predictive 95%-mass-window: [200.69 201.12]

----------------------------
Potential peaks with 8 observation(s)
----------------------------
Number: 1
----------------------------
Position of peak: Scan18MZ203
Course of mass-to-charge values:          203.06  203.06  202.93  202.81
202.97  203.06  203.06  203.06
Course of intensity values:               73414   105568  137722  41128
57890   74652   54154   61095
Indices of imputed values: 2 5
Predictive t-distribution:vau= 100.1, mu= 203.00, sigma2= 0.0115
Predictive 95%-mass-window: [202.79 203.22]
----------------------------
Potential peaks with 10 observation(s)
----------------------------
Number: 1
----------------------------
Position of peak: Scan18MZ205 
Course of mass-to-charge values:          204.73  204.73  204.86  204.86
204.86  204.99  204.99  204.99  204.86
Course of intensity values:               34040   227453  166698  215617
401424  455769  456323  868147  949309  1054378
Indices of imputed values:
Predictive t-distribution:vau= 102.1, mu= 204.88, sigma2= 0.0114
Predictive 95%-mass-window: [204.67 205.10]
```

Fig. 50

Grouping protocol – page 49

19. scan

Table of observations at scan time 939.15 seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 202.29 | 348937 | 203.32 | 76167 | | | 204.99 | 1286662 | | |

Total number of observations: 3

Grouping protocol – page 50

Potential peaks that get updated because some observation
fell in their predictive mass-window for 2 scans Listed by their identifiers and results Scan18MZ2202: all data points were used to update (less than four)
Scan18MZ2205: all data points were used to update (intensity too small)

Potential peaks that get closed because no observation
fell in their predictive mass-window for 2. scans Listed by their identifiers and results Scan18MZ2201: intensity of 72472 is smaller than required 480328

Resulting potential peaks after the 19. Scan

Total number: 5

Potential peaks with 1 observation(s)

Number: 1

Position of peak: Scan19MZ203
Course of mass-to-charge values:     203.32
Course of intensity values:            76167
Indices of imputed values:
Predictive t-distribution:vau= 93.1, mu= 203.32, sigma2= 0.0207
Predictive 95%-mass-window: [203.03 203.61]

Potential peaks with 2 observation(s)

Number: 1

Position of peak: Scan19MZ202
Course of mass-to-charge values:     202.29    202.29
Course of intensity values:            76847   348937
Indices of imputed values:
Predictive t-distribution:vau= 94.1, mu= 202.29, sigma2= 0.0154
Predictive 95%-mass-window: [202.05 202.54]

Potential peaks with 6 observation(s)

Number: 1

Position of peak: Scan19MZ201
Course of mass-to-charge values:     200.88    200.88    200.88    200.88    201.01
200.89    200.88
Course of intensity values:            98661   120034   141407    73167
71974   132145
Indices of imputed values: 2
Predictive t-distribution:vau= 98.1, mu= 200.90, sigma2= 0.0116
Predictive 95%-mass-window: [200.69 201.12]

Potential peaks with 8 observation(s)

Fig. S7

Grouping protocol – page 51

Number: 1
----------
Position of peak: Scan19MZ203
Course of mass-to-charge values:
202.97    203.06    203.06    203.06    203.06    202.93    202.81
Course of intensity values:
57890     74652     54154     73414     61095    105568    137722     41128
Indices of imputed values: 2 5
Predictive t-distribution:vau= 100.1, mu= 203.00, sigma2= 0.0115
Predictive 95%-mass-window: [202.79 203.22]

----------
Potential peaks with 11 observation(s)
----------

Number: 1
----------
→ Position of peak: Scan19MZ205
Course of mass-to-charge values:
204.86    204.99    204.99    204.73    204.73    204.99    204.86    204.86    204.99
204.99    204.99    204.99    204.99    227453    166698    204.86    215617
401424    455769    456323    34040     868147    949309   1054378   1285662
Indices of imputed values:
Predictive t-distribution:vau= 103.1, mu= 204.89, sigma2= 0.0113
Predictive 95%-mass-window: [204.68 205.10]

Grouping protocol – page 52

----------
20. scan
----------
Table of observations at scan time 941.25 seconds
in mass-to-charge window 200.00-205.00 Da
----------
Mass-to-charge: m/z [Da]
Intensity: I [cts]
----------

| m/z | I | m/z | I | m/z | I | m/z | I | m/z | I |
|---|---|---|---|---|---|---|---|---|---|
| 200.63 | 85718 | 201.40 | 260806 | 202.16 | 87474 | 204.99 | 1320664 |

Total number of observations: 4

Fig. 52

Grouping protocol – page 53

---
Potential peaks that get updated because some observation
fell in their predictive mass-window for 2 scans
---
Listed by their identifiers and results
---
Scan19MZ202: all data points were used to update (less than four)
Scan19MZ205: all data points were used to update (intensity too small)
---
Potential peaks that get closed because no observation
fell in their predictive mass-window for 2. scans
---
Listed by their identifiers and results
---
Scan19MZ201: intensity of 84134 is smaller than required 488328
---

Resulting potential peaks after the 20. scan
---

Total number: 5

---
Potential peaks with 1 observation(s)
---
Number: 3

---
Position of peak: Scan20MZ203
Course of mass-to-charge values:    203.12
Course of intensity values:    76167
Indices of imputed values:
Predictive t-distribution:vau= 93.1, mu= 203.32, sigma2= 0.0207
Predictive 95%-mass-window: [203.03 203.61]

---
Position of peak: Scan20MZ201
Course of mass-to-charge values:    200.63
Course of intensity values:    85718
Indices of imputed values:
Predictive t-distribution:vau= 93.1, mu= 200.63, sigma2= 0.0207
Predictive 95%-mass-window: [200.34 200.91]

---
Position of peak: Scan20MZ201
Course of mass-to-charge values:    201.40
Course of intensity values:    260806
Indices of imputed values:
Predictive t-distribution:vau= 93.1, mu= 201.40, sigma2= 0.0207
Predictive 95%-mass-window: [201.11 201.68]

---
Potential peaks with 3 observation(s)
---
Number: 1

---
Position of peak: Scan20MZ202
Course of mass-to-charge values:    202.29    202.29    202.16
Course of intensity values:    76847    348937    87474
Indices of imputed values:
Predictive t-distribution:vau= 95.1, mu= 202.25, sigma2= 0.0137
Predictive 95%-mass-window: [202.02 202.48]

---

Grouping protocol – page 54

Potential peaks with 12 observation(s)
---
Number: 1

---
→ Position of peak: Scan20MZ205
Course of mass-to-charge values:             204.73    204.86    204.86
204.86    204.99    204.99    204.99    204.73    204.86    204.86    204.99
204.99
Course of intensity values:    34040    227453    166698    215617
401424    455769    456323    868147    949309    1054378    1286662
1320664
Indices of imputed values:
Predictive t-distribution:vau= 104.1, mu= 204.90, sigma2= 0.0112
Predictive 95%-mass-window: [204.69 205.11]

Grouping protocol – page 55

---
21. scan
---
Table of observations at scan time 943.35 Seconds
---
in mass-to-charge window 200.00-205.00 Da
---
Mass-to-charge: m/z [Da]
Intensity: I [cts]
---

| m/z | I | m/z | I | m/z | I | m/z | I | m/z | I |
|---|---|---|---|---|---|---|---|---|---|
| 200.88 | 58443 | 201.27 | 114555 | 201.78 | 102306 | 202.29 | 154058 |  |  |
| 204.86 | 1563009 |  |  |  |  |  |  |  |  |

Total number of observations: 5

Grouping protocol – page 56

---
Potential peaks that get updated because some observation
fell in their predictive mass-window for 2 scans
---
Listed by their identifiers and results
---
Scan20MZ201: Decreasing start -> no update but initialization
Scan20MZ201: Decreasing start -> no update but initialization
Scan20MZ202: all data points were used to update (intensity too small)
Scan20MZ205: all data points were used to update (intensity too small)
---
Potential peaks that get closed because no observation
fell in their predictive mass-window for 2. scans
---
Listed by their identifiers and results
---
Scan20MZ203: intensity of 76167 is smaller than required 488328
---
Resulting potential peaks after the 21. scan
---

Total number: 5

---
Potential peaks with 1 observation(s)
---
Number: 3
---
Position of peak: Scan21MZ201
Course of mass-to-charge values:        200.88
Course of intensity values:              58443
Indices of imputed values:
Predictive t-distribution: vau= 93.1, mu= 200.88, sigma2= 0.0207
Predictive 95%-mass-window: [200.60 201.17]
---
Position of peak: Scan21MZ201
Course of mass-to-charge values:        201.27
Course of intensity values:             114555
Indices of imputed values:
Predictive t-distribution: vau= 93.1, mu= 201.27, sigma2= 0.0207
Predictive 95%-mass-window: [200.98 201.55]
---
Position of peak: Scan21MZ202
Course of mass-to-charge values:        201.78
Course of intensity values:             102306
Indices of imputed values:
Predictive t-distribution: vau= 93.1, mu= 201.78, sigma2= 0.0207
Predictive 95%-mass-window: [201.49 202.07]
---
Potential peaks with 4 observation(s)
---
Number: 1
---
Position of peak: Scan21MZ202
Course of mass-to-charge values:     202.29      202.29      202.16      202.29
Course of intensity values:           76847      348937       87474      154058
Indices of imputed values:
Predictive t-distribution: vau= 96.1, mu= 202.26, sigma2= 0.0127
Predictive 95%-mass-window: [202.04 202.48]

Fig. 54

Grouping protocol – page 57

```
---------------------------------------------------
Potential peaks with 13 observation(s)
---------------------------------------------------
Number: 1
---------------------------------------------------
→ Position of peak: Scan21M2205
Course of mass-to-charge values:
                         204.73    204.73    204.86    204.86
204.86    204.99    204.99    204.99    204.86    204.99
204.99    204.86
Course of intensity values:
                         34040    227453    166698    215617
455769    456323    868147    949309   1054378   1286662
1320664   1563009
Indices of imputed values:
Predictive t-distribution: vau= 105.1, mu= 204.90, sigma2= 0.0110
Predictive 95%-mass-window: [204.69 205.11]
```

Grouping protocol – page 58

```
---------------------------------------------------
22. scan
---------------------------------------------------
Table of observations at scan time 945.45 Seconds
in mass-to-charge window 200.00-205.00 Da
---------------------------------------------------
Mass-to-charge: m/z [Da]
Intensity: I [cts]
---------------------------------------------------
 m/z   |  I  |  m/z   |  I   |  m/z   |  I   |  m/z   |  I
200.11 | 34358 | 200.63 | 62820 | 202.55 | 87761 | 204.99 | 1597857

Total number of observations: 4
```

Fig. 55

Grouping protocol - page 59

Potential peaks that get updated because some observation
fell in their predictive mass-window for 2 scans Listed by their identifiers and results Scan21M2201: all data points were used to update (less than four)
Scan21M2205: all data points were used to update (intensity too small)

Resulting potential peaks after the 22. Scan

Total number: 7

---
Potential peaks with 1 observation(s)
---
Number: 4
---
Position of peak: Scan22M2201
Course of mass-to-charge values:       201.27
Course of intensity values:           114555
Indices of imputed values:
Predictive t-distribution:vau= 93.1, mu= 201.27, sigma2= 0.0207
Predictive 95%-mass-window: [200.98 201.55]

Position of peak: Scan22M2202
Course of mass-to-charge values:       201.78
Course of intensity values:           102306
Indices of imputed values:
Predictive t-distribution:vau= 93.1, mu= 201.78, sigma2= 0.0207
Predictive 95%-mass-window: [201.49 202.07]

Position of peak: Scan22M2200
Course of mass-to-charge values:       200.11
Course of intensity values:            34358
Indices of imputed values:
Predictive t-distribution:vau= 93.1, mu= 200.11, sigma2= 0.0207
Predictive 95%-mass-window: [199.83 200.40]

Position of peak: Scan22M2203
Course of mass-to-charge values:       202.55
Course of intensity values:            87761
Indices of imputed values:
Predictive t-distribution:vau= 93.1, mu= 202.55, sigma2= 0.0207
Predictive 95%-mass-window: [202.26 202.84]

---
Potential peaks with 2 observation(s)
---
Number: 1
---
Position of peak: Scan22M2201
Course of mass-to-charge values:       200.88    200.63
Course of intensity values:             58443     62820
Indices of imputed values:
Predictive t-distribution:vau= 94.1, mu= 200.75, sigma2= 0.0159
Predictive 95%-mass-window: [200.50 201.00]

Grouping protocol - page 60

---
Potential peaks with 4 observation(s)
---
Number: 1
---
Position of peak: Scan22M2202
Course of mass-to-charge values:       202.29    202.29    202.16    202.29
Course of intensity values:             76847    348937     87474    154056
Indices of imputed values:
Predictive t-distribution:vau= 96.1, mu= 202.26, sigma2= 0.0127
Predictive 95%-mass-window: [202.04 202.48]

---
Potential peaks with 14 observation(s)
---
Number: 1
---
→ Position of peak: Scan22M2205
Course of mass-to-charge values:       204.73    204.73    204.86    204.86
204.86    204.99    204.99    204.99    204.86    204.86    204.99
204.99    204.86                                                   215617
Course of intensity values:             34040    227453    166698   1286662
401424    455769    456323    949309   1054378
1120664   1563009   1597857    868147
Indices of imputed values:
Predictive t-distribution:vau= 106.1, mu= 204.90, sigma2= 0.0109
Predictive 95%-mass-window: [204.70 205.11]

Fig. 96

Grouping protocol – page 61

23. scan

Table of observations at scan time 947.55 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 201.14 | 122228 | 201.78 | 38027 | 202.81 | 69712 | 204.86 | 1418667 | | |

Total number of observations: 4

Grouping protocol – page 62

Potential peaks that get updated because some observation
fell in their predictive mass-window for 2 scans Listed by their identifiers and results Scan22MZ201: all data points were used to update (less than four)
Scan22MZ202: Decreasing start -> no update but initialization
Scan22MZ203: Decreasing start -> no update but initialization
Scan22MZ205: all data points were used to update (unimodality okay)

Potential peaks that get closed because no observation
fell in their predictive mass-window for 2. scans Listed by their identifiers and results Scan2MZ202: intensity of 266776 is smaller than required 485489

Resulting potential peaks after the 23. Scan

Total number: 6

Potential peaks with 1 observation(s)

Number: 3

Position of peak: Scan23MZ202
Course of mass-to-charge values:      201.78
Course of intensity values:         38027
Indices of imputed values:
Predictive t-distribution:vau= 93.1, mu= 201.78, sigma2= 0.0207
Predictive 95%-mass-window: [201.49 202.07]

Position of peak: Scan23MZ200
Course of mass-to-charge values:      200.11
Course of intensity values:         34358
Indices of imputed values:
Predictive t-distribution:vau= 93.1, mu= 200.11, sigma2= 0.0207
Predictive 95%-mass-window: [199.83 200.40]

Position of peak: Scan23MZ203
Course of mass-to-charge values:      202.81
Course of intensity values:         69712
Indices of imputed values:
Predictive t-distribution:vau= 93.1, mu= 202.81, sigma2= 0.0207
Predictive 95%-mass-window: [202.52 203.09]

Potential peaks with 2 observation(s)

Number: 1

Position of peak: Scan23MZ201
Course of mass-to-charge values:      200.88      200.63
Course of intensity values:         58443       62820
Indices of imputed values:
Predictive t-distribution:vau= 94.1, mu= 200.75, sigma2= 0.0159
Predictive 95%-mass-window: [200.50 201.00]

Fig. 57

Grouping protocol – page 65

```
----------------------------------------------------------------
Potential peaks that get updated because some observation
fell in their predictive mass-window for 2 scans
----------------------------------------------------------------
Listed by their identifiers and results Scan23MZ201: all data points were used to update (intensity too small)
Scan23MZ202: Decreasing start -> no update but initialization
Scan23MZ203: all data points were used to update (less than four)
Scan23MZ205: all data points were used to update (less than four)
Scan23MZ205: all data points were used to update (unimodality okay)

----------------------------------------------------------------
Potential peaks that get closed because no observation
fell in their predictive mass-window for 2. scans
----------------------------------------------------------------
Listed by their identifiers and results Scan23MZ200: intensity of 34358 is smaller than required 485489
----------------------------------------------------------------
Resulting potential peaks after the 24. Scan
----------------------------------------------------------------
Total number: 5

----------------------------------------------------------------
Potential peaks with 1 observation(s)
----------------------------------------------------------------
Number: 2

Position of peak: Scan24MZ202
Course of mass-to-charge values:      201.78
Course of intensity values:            27167
Indices of imputed values:
Predictive t-distribution:vau= 93.1, mu= 201.78, sigma2= 0.0207
Predictive 95%-mass-window: [201.49 202.07]

Position of peak: Scan24MZ202
Course of mass-to-charge values:      202.29
Course of intensity values:            51862
Indices of imputed values:
Predictive t-distribution:vau= 93.1, mu= 202.29, sigma2= 0.0207
Predictive 95%-mass-window: [202.01 202.58]

----------------------------------------------------------------
Potential peaks with 2 observation(s)
----------------------------------------------------------------
Number: 1

Position of peak: Scan24MZ203
Course of mass-to-charge values:      202.81    202.93
Course of intensity values:            69712    142821
Indices of imputed values:
Predictive t-distribution:vau= 94.1, mu= 202.87, sigma2= 0.0155
Predictive 95%-mass-window: [202.62 203.12]

----------------------------------------------------------------
Potential peaks with 4 observation(s)
----------------------------------------------------------------
Number: 1

Position of peak: Scan24MZ201
```

Grouping protocol – page 66

```
Course of mass-to-charge values:       201.27    201.27    201.27    201.14    201.01
Course of intensity values:            114555    118392    122228     87958
Indices of imputed values: 2
Predictive t-distribution:vau= 96.1, mu= 201.17, sigma2= 0.0131
Predictive 95%-mass-window: [200.94 201.40]

----------------------------------------------------------------
Potential peaks with 16 observation(s)
----------------------------------------------------------------
Number: 1

Position of peak: Scan24MZ205
Course of mass-to-charge values:       204.73    204.73    204.86    204.86
204.86    204.99    204.99    204.99    204.99    204.86    204.99
204.99    204.86    204.86
Course of intensity values:             34040    227453    166698    215617
401424    455769    456323    868147    949309   1054378   1286662
1320664   1563009   1597857   1418667
Indices of imputed values:
Predictive t-distribution:vau= 108.1, mu= 204.91, sigma2= 0.0107
Predictive 95%-mass-window: [204.70 205.11]
```

Fig. 59

Grouping protocol – page 67

25. scan

Table of observations at scan time 951.75 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 201.40 | 195186 | 202.29 | 54865 | 202.81 | 148329 | 202.93 | 151021 | | |
| 204.99 | 1205349 | | | | | | | | |

Total number of observations: 5

Grouping protocol – page 68

Potential peaks that get updated because some observation
fell in their predictive mass-window for 2 scans Listed by their identifiers and results Scan24MZ201: all data points were used to update (intensity too small)
Scan24MZ202: all data points were used to update (less than four)
Scan24MZ203: all data points were used to update (less than four)
Scan24MZ204: all data points were used to update (less than four)
Scan24MZ205: all data points were used to update (unimodality okay)

Resulting potential peaks after the 25. Scan

Total number: 5

Potential peaks with 1 observation(s)

Number: 1
Position of peak: Scan25MZ202
Course of mass-to-charge values:           201.78
Course of intensity values:                27167
Indices of imputed values:
Predictive t-distribution:vau= 93.1, mu= 201.78, sigma2= 0.0207
Predictive 95%-mass-window: [201.49 202.07]

Potential peaks with 2 observation(s)

Number: 1
Position of peak: Scan25MZ202
Course of mass-to-charge values:           202.29     202.29
Course of intensity values:                51862      54865
Indices of imputed values:
Predictive t-distribution:vau= 94.1, mu= 202.29, sigma2= 0.0154
Predictive 95%-mass-window: [202.05 202.54]

Potential peaks with 3 observation(s)

Number: 1
Position of peak: Scan25MZ203
Course of mass-to-charge values:           202.81     202.93     202.93
Course of intensity values:                69712      142821     151021
Indices of imputed values:
Predictive t-distribution:vau= 95.1, mu= 202.89, sigma2= 0.0137
Predictive 95%-mass-window: [202.66 203.12]

Potential peaks with 5 observation(s)

Number: 1
Position of peak: Scan25MZ201
Course of mass-to-charge values:           201.27     201.27     201.14     201.01
201.40

Fig. 60

Grouping protocol - page 69

```
Course of intensity values:     114555     118392     122228     87958
195186
Indices of imputed values: 2
Predictive t-distribution:vau= 97.1, mu= 201.22, sigma2= 0.0130
Predictive 95%-mass-window: [200.99 201.44]

---------------------------------------------------------------
Potential peaks with 17 observation(s)
---------------------------------------------------------------
Number: 1
---------------------------------------------------------------
→ Position of peak: Scan25MZ205 ←
Course of mass-to-charge values:
                              204.73     204.73     204.99     204.06     204.86
204.86    204.99    204.99   204.99     204.86    204.86    204.99
204.99    204.86    204.99
Course of intensity values:
                              34040     227453    166698    215617
401424    455759    456323    868147    949309    1054378   1205349
1320664   1563009   15977657  1418667   1567542   1286662
Indices of imputed values:
Predictive t-distribution:vau= 109.1, mu= 204.91, sigma2= 0.0106
Predictive 95%-mass-window: [204.71 205.12]
```

Grouping protocol - page 70

```
26. scan

Table of observations at scan time 953.85 Seconds
in mass-to-charge window 200.00-205.00 Da Mass-to-charge: m/z [Da]
Intensity: I [cts]

m/z    I |  m/z    I |  m/z    I |  m/z    I |

200.24  64502 | 201.78  103304 | 204.86  1549879 |

Total number of observations: 3
```

Fig. 67

Grouping protocol - page 71

```
Potential peaks that get updated because some observation
fell in their predictive mass-window for 2 scans Listed by their identifiers and results Scan25MZ202: all data points were used to update (less than four)
Scan25MZ205: all data points were used to update (unimodality okay)

Resulting potential peaks after the 26. Scan

Total number: 6

Potential peaks with 1 observation(s)
----------------------
Number: 1
----------------------
Position of peak: Scan26MZ200
Course of mass-to-charge values:    200.24
Course of intensity values:          64502
Indices of imputed values:
Predictive t-distribution:vau= 93.1, mu= 200.24, sigma2= 0.0207
Predictive 95%-mass-window: (199.95 200.53]

Potential peaks with 2 observation(s)
----------------------
Number: 1
----------------------
Position of peak: Scan26MZ202
Course of mass-to-charge values:    202.29      202.29
Course of intensity values:          51862       54865
Indices of imputed values:
Predictive t-distribution:vau= 94.1, mu= 202.29, sigma2= 0.0154
Predictive 95%-mass-window: [202.05 202.54]

Potential peaks with 3 observation(s)
----------------------
Number: 1
----------------------
Position of peak: Scan26MZ202
Course of mass-to-charge values:    201.78      201.78      201.78
Course of intensity values:          27167       65235      103304
Indices of imputed values: 2
Predictive t-distribution:vau= 95.1, mu= 201.78, sigma2= 0.0135
Predictive 95%-mass-window: [201.55 202.01]

Position of peak: Scan26MZ203
Course of mass-to-charge values:    202.81      202.93      202.93
Course of intensity values:          69712      142821      151021
Indices of imputed values:
Predictive t-distribution:vau= 95.1, mu= 202.89, sigma2= 0.0137
Predictive 95%-mass-window: [202.66 203.12]

Potential peaks with 5 observation(s)
----------------------
Number: 1
```

Grouping protocol - page 72

```
Position of peak: Scan26MZ201
Course of mass-to-charge values:    201.27      201.27      201.14      201.01
201.40
Course of intensity values:         114555      118392      122228       87958
195186
Indices of imputed values: 2
Predictive t-distribution:vau= 97.1, mu= 201.22, sigma2= 0.0130
Predictive 95%-mass-window: [200.99 201.44]

Potential peaks with 18 observation(s)
----------------------
Number: 1
----------------------
→ Position of peak: Scan26MZ205
Course of mass-to-charge values:             204.73      204.73      204.86      204.86
204.86      204.99      204.99      204.99      204.99      204.86
204.99      204.86      204.99      204.86      204.99      204.86
Course of intensity values:         34040      227453      949309      166698      215617
401424      455769      456323      868147     1054378     1286662
1320664     1563009     1597857     1418667     1205349     1549879
Indices of imputed values:
Predictive t-distribution:vau= 110.1, mu= 204.91, sigma2= 0.0105
Predictive 95%-mass-window: [204.71 205.11]
```

Fig. 62

Grouping protocol - page 73

27. scan

Table of observations at scan time 955.96 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.75 | 116933 | 201.91 | 115734 | 203.19 | 121031 | 204.99 | 1322807 | | |

Total number of observations: 4

Grouping protocol - page 74

Potential peaks that get updated because some observation
fell in their predictive mass-window for 2 scans
----------------------------------------------------------
Listed by their identifiers and results
----------------------------------------------------------
Scan26MZ202: all data points were used to update (intensity too small)
Scan26MZ205: all data points were used to update (unimodality okay)
----------------------------------------------------------

Potential peaks that get closed because no observation
fell in their predictive mass-window for 2. scans
----------------------------------------------------------
Listed by their identifiers and results
----------------------------------------------------------
Scan26MZ202: intensity of 51862 is smaller than required 485469
----------------------------------------------------------

Resulting potential peaks after the 27. Scan
----------------------------------------------------------

Total number: 5

Potential peaks with 1 observation(s)
----------------------------------------------------------
Number: 3
----------------------------------------------------------
Position of peak: Scan27MZ200
Course of mass-to-charge values:    200.24
Course of intensity values:        64502
Indices of imputed values:
Predictive t-distribution: vau= 93.1, mu= 200.24, sigma2= 0.0207
Predictive 95%-mass-window: [199.95 200.53]

Position of peak: Scan27MZ201
Course of mass-to-charge values:    200.75
Course of intensity values:       116933
Indices of imputed values:
Predictive t-distribution: vau= 93.1, mu= 200.75, sigma2= 0.0207
Predictive 95%-mass-window: [200.47 201.04]

Position of peak: Scan27MZ203
Course of mass-to-charge values:    203.19
Course of intensity values:       121031
Indices of imputed values:
Predictive t-distribution: vau= 93.1, mu= 203.19, sigma2= 0.0207
Predictive 95%-mass-window: [202.91 203.48]

Potential peaks with 4 observation(s)
----------------------------------------------------------
Number: 1
----------------------------------------------------------
Position of peak: Scan27MZ202
Course of mass-to-charge values:    201.78    201.78    201.78    201.91
Course of intensity values:        27167     65235    103304    115734
Indices of imputed values: 2
Predictive t-distribution: vau= 96.1, mu= 201.81, sigma2= 0.0127
Predictive 95%-mass-window: [201.59 202.04]

Fig. 63

Grouping protocol – page 75

```
------------------------------------------------
Potential peaks with 19 observation(s)
------------------------------------------------
Number: 1
------------------------------------------------
Position of peak: Scan27MZ205
Course of mass-to-charge values:
204.86    204.99   204.99   204.73   204.73   204.86   204.86
204.99    204.86   204.99   204.99   204.99   204.86   204.99
204.99                                                  204.86
Course of intensity values:
401424    455769   34040    227453   166698   1054378  215617
1320664   1563009  868147   949309   1054378  1205349  1286662
1322807            1418667  1567542           1205349  1549879
Indices of imputed values:
Predictive t-distribution:vau= 111.1, mu= 204.91, sigma2= 0.0105
Predictive 95%-mass-window: [204.71 205.12]
```

Grouping protocol – page 76

```
------------------------------------------------
28. scan
------------------------------------------------
Table of observations at scan time 958.06 Seconds
in mass-to-charge window 200.00-205.00 Da
------------------------------------------------

Mass-to-charge: m/z [Da]
Intensity: I [cts]

m/z   I | m/z   I | m/z   I | m/z   I |
201.27 93284 | 202.42 53967 | 204.86 1234574 |

Total number of observations: 3
```

Fig. 64

Grouping protocol - page 77

Potential peaks that get updated because some observation
fell in their predictive mass-window for 2 scans
------------------------------------------------------------
Listed by their identifiers and results
------------------------------------------------------------
Scan27MZ205: all data points were used to update (unimodality okay)

Potential peaks that get closed because no observation
fell in their predictive mass-window for 2. scans
------------------------------------------------------------
Listed by their identifiers and results
------------------------------------------------------------
Scan27MZ200: intensity of 64502 is smaller than required 485489

Resulting potential peaks after the 28. Scan
------------------------------------------------------------
Total number: 6

Potential peaks with 1 observation(s)
------------------------------------------------------------
Number: 4
Position of peak: Scan28MZ201
Course of mass-to-charge values:   200.75
Course of intensity values:        116933
Indices of imputed values:
Predictive t-distribution: vau= 93.1, mu= 200.75, sigma2= 0.0207
Predictive 95%-mass-window: [200.47 201.04]

Position of peak: Scan28MZ203
Course of mass-to-charge values:   203.19
Course of intensity values:        121031
Indices of imputed values:
Predictive t-distribution: vau= 93.1, mu= 203.19, sigma2= 0.0207
Predictive 95%-mass-window: [202.91 203.48]

Position of peak: Scan28MZ201
Course of mass-to-charge values:   201.27
Course of intensity values:        93284
Indices of imputed values:
Predictive t-distribution: vau= 93.1, mu= 201.27, sigma2= 0.0207
Predictive 95%-mass-window: [200.98 201.55]

Position of peak: Scan28MZ202
Course of mass-to-charge values:   202.42
Course of intensity values:        53957
Indices of imputed values:
Predictive t-distribution: vau= 93.1, mu= 202.42, sigma2= 0.0207
Predictive 95%-mass-window: [202.14 202.71]

Potential peaks with 4 observation(s)
------------------------------------------------------------
Number: 1
Position of peak: Scan28MZ202

Grouping protocol - page 78

Course of mass-to-charge values:   201.78   201.78   201.78   201.91
Course of intensity values:        27167    65225    103304   115734
Indices of imputed values: 2
Predictive t-distribution: vau= 96.1, mu= 201.81, sigma2= 0.0127
Predictive 95%-mass-window: [201.59 202.04]

Potential peaks with 20 observation(s)
------------------------------------------------------------
Number: 1
→ Position of peak: Scan28MZ205
Course of mass-to-charge values:   204.73   204.86   204.86
204.86   204.99   204.99   204.99   204.86   204.99
204.99   204.86   204.99   204.99   204.99   204.86
204.99   204.86
Course of intensity values:   34040    227453   166598   215617
401424   455769   456323   868147   943309   1054378  1286662
1320664  1563009  1597857  1418667  1567542  1205349  1549879
1322807  1234574
Indices of imputed values:
Predictive t-distribution: vau= 112.1, mu= 204.91, sigma2= 0.0104
Predictive 95%-mass-window: [204.71 205.11]

Fig. 65

Grouping protocol – page 79

29. scan

Table of observations at scan time 960.16 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.11 | 26655 | 200.75 | 74970 | 200.88 | 116615 | 202.29 | 128869 | | |
| 202.68 | 58579 | 204.99 | 873526 | | | | | | |

Total number of observations: 6

Grouping protocol – page 80

Potential peaks that get updated because some observation
fell in their predictive mass-window for 2 scans
--------------------------------------------------------
Listed by their identifiers and results Scan28MZ201: Decreasing start -> no update but initialization
Scan28MZ201: all data points were used to update (less than four)
Scan28MZ202: all data points were used to update (less than four)
Scan28MZ205: all data points were used to update (unimodality okay)

Potential peaks that get closed because no observation
fell in their predictive mass-window for 2. scans
--------------------------------------------------------
Listed by their identifiers and results Scan28MZ203: intensity of 121031 is smaller than required 488328
--------------------------------------------------------

Resulting potential peaks after the 29. Scan

Total number: 6

--------------------------------------------------------
Potential peaks with 1 observation(s)
--------------------------------------------------------
Number: 3

Position of peak: Scan29MZ201
Course of mass-to-charge values:   201.27
Course of intensity values:   93284
Indices of imputed values:
Predictive t-distribution:vau= 93.1, mu= 201.27, sigma2= 0.0207
Predictive 95%-mass-window: [200.98 201.55]

Position of peak: Scan29MZ200
Course of mass-to-charge values:   200.11
Course of intensity values:   26655
Indices of imputed values:
Predictive t-distribution:vau= 93.1, mu= 200.11, sigma2= 0.0207
Predictive 95%-mass-window: [199.83 200.40]

Position of peak: Scan29MZ203
Course of mass-to-charge values:   202.68
Course of intensity values:   58579
Indices of imputed values:
Predictive t-distribution:vau= 93.1, mu= 202.68, sigma2= 0.0207
Predictive 95%-mass-window: [202.39 202.96]

--------------------------------------------------------
Potential peaks with 2 observation(s)
--------------------------------------------------------
Number: 2

Position of peak: Scan29MZ201
Course of mass-to-charge values:   200.75    200.88
Course of intensity values:   95792   116615
Indices of imputed values: 2
Predictive t-distribution:vau= 94.1, mu= 200.82, sigma2= 0.0155
Predictive 95%-mass-window: [200.57 201.06]

Fig. 66

Grouping protocol – page 81

```
Position of peak: Scan29MZ2202
Course of mass-to-charge values:        202.42      202.29
Course of intensity values:          53967      128869
Indices of imputed values:
Predictive t-distribution:vau= 94.1, mu= 202.36, sigma2= 0.0155
Predictive 95%-mass-window: [202.11 202.60]

Potential peaks with 21 observation(s)
Number: 1
Position of peak: Scan29MZ2205
Course of mass-to-charge values:
204.86   204.99   204.73    204.99   204.73   204.86   204.86   204.86
204.99   204.86   204.99   204.99   204.86   204.99   204.86   204.99
204.99   204.86   204.99
Course of intensity values:
401424    455769   34040     227453   166698  215617
1320664  1563009  456323    868147   949309  1054378  1286662
1322807  1234574  1597857  1418667  1567542  1205349  1549879
                     873526
Indices of imputed values:
Predictive t-distribution:vau= 113.1, mu= 204.91, sigma2= 0.0103
Predictive 95%-mass-window: [204.71 205.12]
```

Grouping protocol – page 82

```
30. scan

Table of observations at scan time 962.26 Seconds
in mass-to-charge window 200.00-205.00 Da Mass-to-charge: m/z [Da]
Intensity: I [cts]

m/z   |   I   |  m/z   |   I   |  m/z   |   I   |  m/z   |   I
200.88 | 117134 | 202.42 | 98365 | 203.19 | 52454 | 204.99 | 733510

Total number of observations: 4
```

Fig. 67

Grouping protocol – page B3

```
Potential peaks that get updated because some observation
fell in their predictive mass-window for 2 scans
-------------------------------------------------------------
Listed by their identifiers and results
-------------------------------------------------------------
Scan29MZ201: all data points were used to update (less than four)
Scan29MZ202: all data points were used to update (less than four)
Scan29MZ205: all data points were used to update (unimodality okay)
-------------------------------------------------------------
Potential peaks that get closed because no observation
fell in their predictive mass-window for 2. scans
-------------------------------------------------------------
Listed by their identifiers and results
-------------------------------------------------------------
Scan29MZ201: intensity of 93284 is smaller than required 488328
-------------------------------------------------------------
Resulting potential peaks after the 30. Scan
-------------------------------------------------------------
Total number: 6
-------------------------------------------------------------
Potential peaks with 1 observation(s)
-------------------------------------------------------------
Number: 3
-------------------------------------------------------------
Position of peak: Scan30MZ200
Course of mass-to-charge values:    200.11
Course of intensity values:         26655
Indices of imputed values:
Predictive t-distribution:vau= 93.1, mu= 200.11, sigma2= 0.0207
Predictive 95%-mass-window: [199.83 200.40]
-------------------------------------------------------------
Position of peak: Scan30MZ203
Course of mass-to-charge values:    202.68
Course of intensity values:         58579
Indices of imputed values:
Predictive t-distribution:vau= 93.1, mu= 202.68, sigma2= 0.0207
Predictive 95%-mass-window: [202.39 202.96]
-------------------------------------------------------------
Position of peak: Scan30MZ203
Course of mass-to-charge values:    203.19
Course of intensity values:         52454
Indices of imputed values:
Predictive t-distribution:vau= 93.1, mu= 203.19, sigma2= 0.0207
Predictive 95%-mass-window: [202.91 203.48]
-------------------------------------------------------------
Potential peaks with 3 observation(s)
-------------------------------------------------------------
Number: 2
-------------------------------------------------------------
Position of peak: Scan30MZ201
Course of mass-to-charge values:    200.75    200.88    200.88
Course of intensity values:         95792     116615    117134
Indices of imputed values: 2
Predictive t-distribution:vau= 95.1, mu= 200.84, sigma2= 0.0137
Predictive 95%-mass-window: [200.61 201.07]
```

Grouping protocol – page 84

```
Position of peak: Scan30MZ202
Course of mass-to-charge values:    202.42    202.42    202.29    202.42
Course of intensity values:         53957     120869    98365
Indices of imputed values:
Predictive t-distribution:vau= 95.1, mu= 202.38, sigma2= 0.0137
Predictive 95%-mass-window: [202.15 202.61]
-------------------------------------------------------------
Potential peaks with 22 observation(s)
-------------------------------------------------------------
Number: 1
-------------------------------------------------------------
Position of peak: Scan30MZ205
Course of mass-to-charge values:    204.73    204.73    204.86    204.86
204.86    204.99    204.99    204.99    204.86    204.86    204.99
204.99    204.86    204.86    204.99    204.99    204.99    204.86
Course of intensity values:         34040     227453    166698    215617
401424    455769    456323    868147    949909    1054378   1286662
1320664   1563009   1597857   1418667   1567542   1205349   1549879
1322807   1234574   873526    733510
Indices of imputed values:
Predictive t-distribution:vau= 114.1, mu= 204.92, sigma2= 0.0103
Predictive 95%-mass-window: [204.72 205.12]
```

Fig. 68

Grouping protocol - page 85

31. scan

Table of observations at scan time 964.36 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 201.40 | 212820 | 202.16 | 50979 | 203.06 | 64889 | 204.99 | 787308 | | |

Total number of observations: 4

Grouping protocol - page 86

Potential peaks that get updated because some observation
fell in their predictive mass-window for 2 scans Listed by their identifiers and results Scan30MZ202: all data points were used to update (intensity too small)
Scan30MZ203: all data points were used to update (less than four)
Scan30MZ205: all data points were used to update (unimodality okay)

Potential peaks that get closed because no observation
fell in their predictive mass-window for 2. scans Listed by their identifiers and results Scan30MZ203: intensity of 58579 is smaller than required 488328

Resulting potential peaks after the 31. Scan

Total number: 5

Potential peaks with 1 observation(s)

Number: 1

Position of peak: Scan31MZ201
Course of mass-to-charge values:     201.40
Course of intensity values:     212820
Indices of imputed values:
Predictive t-distribution:vau= 93.1, mu= 201.40, sigma2= 0.0207
Predictive 95%-mass-window: [201.11 201.68]

Potential peaks with 2 observation(s)

Number: 1

Position of peak: Scan31MZ203
Course of mass-to-charge values:     203.19     203.06
Course of intensity values:     52454     64889
Indices of imputed values:
Predictive t-distribution:vau= 94.1, mu= 203.13, sigma2= 0.0155
Predictive 95%-mass-window: [202.88 203.37]

Potential peaks with 3 observation(s)

Number: 1

Position of peak: Scan31MZ201
Course of mass-to-charge values:     200.75     200.88     200.08
Course of intensity values:     95792     116615     117134
Indices of imputed values: 2
Predictive t-distribution:vau= 95.1, mu= 200.84, sigma2= 0.0137
Predictive 95%-mass-window: [200.61 201.07]

Potential peaks with 4 observation(s)

Number: 1

Fig. 69

Grouping protocol – page 87

```
-------------------------------------------------------------------
Position of peak: Scan31MZ202
Course of mass-to-charge values:   202.42   202.29   202.42   202.16
Course of intensity values:         53967   128869    98365    50979
Indices of imputed values:
Predictive t-distribution:vau= 96.1, mu= 202.33, sigma2= 0.0131
Predictive 95%-mass-window: [202.10 202.55]
-------------------------------------------------------------------
Potential peaks with 23 observation(s)
-------------------------------------------------------------------
Number: 1
Position of peak: Scan31MZ205
Course of mass-to-charge values:    204.73            204.86   204.86
204.85   204.99   204.99   204.86   204.99   204.99   204.99   204.99
204.99   204.86   204.86   204.99   204.99   204.99   204.86   204.86
Course of intensity values:          34040   227453   166698   215617
401424   455769   456323   868147   949309  1054378  1286662
1320664  1563009  1597857  1418667  1567542  1205349  1549879
1322807  1234574   873526   733510   787308
Indices of imputed values:
Predictive t-distribution:vau= 115.1, mu= 204.92, sigma2= 0.0102
Predictive 95%-mass-window: [204.72 205.12]
```

Grouping protocol – page 88

```
-------------------------------------------------------------------
32. scan
-------------------------------------------------------------------
Table of observations at scan time 966.46 seconds
in mass-to-charge window 200.00-205.00 Da
-------------------------------------------------------------------
Mass-to-charge: m/z [Da]
Intensity: I [cts]

m/z     I | m/z     I | m/z     I | m/z     I | m/z     I |

201.01 81317 | 203.32 83336 | 204.86 752379 |

Total number of observations: 3
```

Fig. 70

Grouping protocol – page 89

```
Potential peaks that get updated because some observation
fell in their predictive mass-window for 2 scans Listed by their identifiers and results Scan31MZ201: all data points were used to update (intensity too small)
Scan31MZ203: all data points were used to update (less than four)
Scan31MZ205: all data points were used to update (unimodality okay)

Resulting potential peaks after the 32. Scan

Total number: 5

-----------------------------------------------
Potential peaks with 1 observation(s)
-----------------------------------------------
Number: 1
-----------
Position of peak: Scan32MZ201
Course of mass-to-charge values:    201.40
Course of intensity values:         212820
Indices of imputed values:
Predictive t-distribution:vau= 93.1, mu= 201.40, sigma2= 0.0207
Predictive 95%-mass-window: [201.11 201.68]

-----------------------------------------------
Potential peaks with 3 observation(s)
-----------------------------------------------
Number: 1
-----------
Position of peak: Scan32MZ203
Course of mass-to-charge values:    203.19   203.06   203.32
Course of intensity values:         52454    64889    83336
Indices of imputed values:
Predictive t-distribution:vau= 95.1, mu= 203.19, sigma2= 0.0140
Predictive 95%-mass-window: [202.96 203.43]

-----------------------------------------------
Potential peaks with 4 observation(s)
-----------------------------------------------
Number: 1
-----------
Position of peak: Scan32MZ202
Course of mass-to-charge values:    202.42   202.29   202.42   202.16
Course of intensity values:         53967    128869   98365    50979
Indices of imputed values:
Predictive t-distribution:vau= 96.1, mu= 202.33, sigma2= 0.0131
Predictive 95%-mass-window: [202.10 202.55]

-----------------------------------------------
Potential peaks with 5 observation(s)
-----------------------------------------------
Number: 1
-----------
Position of peak: Scan32MZ201
Course of mass-to-charge values:    200.75   200.88   200.88   200.84
201.01
Course of intensity values:         95792    116615   117134   99225
81317
Indices of imputed values: 2 4
```

Grouping protocol – page 90

```
Predictive t-distribution:vau= 97.1, mu= 200.87, sigma2= 0.0123
Predictive 95%-mass-window: [200.65 201.09]

-----------------------------------------------
Potential peaks with 24 observation(s)
-----------------------------------------------
Number: 1
-----------
Position of peak: Scan32MZ205
Course of mass-to-charge values:
                                             204.73           204.86   204.86
204.86    204.99   204.99   204.86   204.99   204.99           204.99   204.99
204.99    204.86   204.86                     204.99   204.99  204.86   204.86
Course of intensity values:
401424    455769   456323   34040    227453   949309  166698   215617
1320664   1563009  1597857  868147   1418667  1567542 1054378  1286662
1322807   1234574  873526   733510   787308           1205349  1549879
                                                      752379
Indices of imputed values:
Predictive t-distribution:vau= 116.1, mu= 204.92, sigma2= 0.0101
Predictive 95%-mass-window: [204.72 205.12]
```

Fig. 71

Grouping protocol – page 91

33. scan

Table of observations at scan time 968.56 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.75 | 120617 | 202.16 | 24459 | 202.16 | 30349 | 202.93 | 33380 | | |
| 203.70 | 85378 | 204.99 | 399262 | | | | | | |

Total number of observations: 6

Grouping protocol – page 92

Potential peaks that get updated because some observation
fell in their predictive mass-window for 2 scans Listed by their identifiers and results Scan32MZ201: all data points were used to update (intensity too small)
Scan32MZ202: all data points were used to update (intensity too small)
Scan32MZ202: all data points were used to update (intensity too small)
Scan32MZ205: all data points were used to update (unimodality okay)

Potential peaks that get closed because no observation
fell in their predictive mass-window for 2 scans Listed by their identifiers and results Scan32MZ201: intensity of 212820 is smaller than required 488328

Resulting potential peaks after the 33. Scan

Total number: 6

Potential peaks with 1 observation(s)

Number: 2

Position of peak: Scan33MZ203
Course of mass-to-charge values:     202.93
Course of intensity values:      33380
Indices of imputed values:
Predictive t-distribution:vau= 93.1, mu= 202.93, sigma2= 0.0207
Predictive 95%-mass-window: [202.65 203.22]

Position of peak: Scan33MZ204
Course of mass-to-charge values:     203.70
Course of intensity values:      85378
Indices of imputed values:
Predictive t-distribution:vau= 93.1, mu= 203.70, sigma2= 0.0207
Predictive 95%-mass-window: [203.42 203.99]

Potential peaks with 3 observation(s)

Number: 1

Position of peak: Scan33MZ203
Course of mass-to-charge values:      203.19       203.06      203.32
Course of intensity values:      52454        64089       83336
Indices of imputed values:
Predictive t-distribution:vau= 95.1, mu= 203.19, sigma2= 0.0140
Predictive 95%-mass-window: [202.96 203.43]

Potential peaks with 6 observation(s)

Number: 2

Position of peak: Scan33MZ201

Fig. 72

Grouping protocol – page 93

```
Course of mass-to-charge values:      200.75      200.88      200.88      200.84
201.01    200.75
Course of intensity values:            95792      116615      117134       99225
81317    120617
Indices of imputed values: 2 4
Predictive t-distribution:vau= 98.1, mu= 200.85, sigma2= 0.0120
Predictive 95%-mass-window: [200.64 201.07]

Position of peak: Scan33MZ202
Course of mass-to-charge values:      202.42      202.42      202.29      202.42      202.16
202.33    202.16
Course of intensity values:            53967      128869       98365       50979
37719     30349
Indices of imputed values: 5
Predictive t-distribution:vau= 98.1, mu= 202.30, sigma2= 0.0123
Predictive 95%-mass-window: [202.08 202.52]

Potential peaks with 25 observation(s)

-----------
Number: 1
-----------
↑ Position of peak: Scan33MZ205  ←
Course of mass-to-charge values:      204.73      204.73      204.86      204.86
204.86    204.99      204.99      204.99      204.99      204.86      204.99
204.99    204.86      204.86      204.99      204.99      204.86      204.86
204.99    204.86      204.99
Course of intensity values:            34040      227453      166698      215617
401424    455769      456323      868147      949309     1054378     1286662
1320664   1563009    1597857     1418667     1567542     1205349     1549879
1322807   1234574     873526      733510      787308      752379      399262
Indices of imputed values:
Predictive t-distribution:vau= 117.1, mu= 204.92, sigma2= 0.0101
Predictive 95%-mass-window: [204.72 205.12]
```

Grouping protocol – page 94

```
----------
34. scan
----------

Table of observations at scan time 970.66 Seconds
in mass-to-charge window 200.00-205.00 Da Mass-to-charge: m/z [Da]
Intensity: I [cts]

m/z      I  | m/z      I  | m/z      I  | m/z      I  | m/z      I 200.88  124203 | 202.16   24187 | 202.93  132497 | 203.70   57569
204.86  164562 |

Total number of observations: 5
```

Fig. 73

Grouping protocol – page 95

```
-------------------------------------------------------
Potential peaks that get updated because some observation
fell in their predictive mass-window for 2 scans
-------------------------------------------------------
Listed by their identifiers and results
Scan33MZ201: all data points were used to update (intensity too small)
Scan33MZ202: all data points were used to update (intensity too small)
Scan33MZ203: all data points were used to update (less than four)
Scan33MZ204: Decreasing start -> no update but initialization
Scan33MZ205: all data points were used to update (unimodality okay)

-------------------------------------------------------
Potential peaks that get closed because no observation
fell in their predictive mass-window for 2. scans
-------------------------------------------------------
Listed by their identifiers and results
Scan33MZ203: intensity of 52454 is smaller than required 488328

-------------------------------------------------------
Resulting potential peaks after the 34. Scan
-------------------------------------------------------
Total number: 5

-------------------------------------------------------
Potential peaks with 1 observation(s)
-------------------------------------------------------
Number: 1
-------------------------------------------------------
Position of peak: Scan34MZ204
Course of mass-to-charge values:     203.70
Course of intensity values:           57569
Indices of imputed values:
Predictive t-distribution:vau= 93.1, mu= 203.70, sigma2= 0.0207
Predictive 95%-mass-window: [203.42 203.99]

-------------------------------------------------------
Potential peaks with 2 observation(s)
-------------------------------------------------------
Number: 1
-------------------------------------------------------
Position of peak: Scan34MZ203
Course of mass-to-charge values:     202.93      202.93
Course of intensity values:           33380      132497
Indices of imputed values:
Predictive t-distribution:vau= 94.1, mu= 202.93, sigma2= 0.0154
Predictive 95%-mass-window: [202.69 203.18]

-------------------------------------------------------
Potential peaks with 7 observation(s)
-------------------------------------------------------
Number: 2
-------------------------------------------------------
Position of peak: Scan34MZ201
Course of mass-to-charge values:     200.75    200.88    200.88    200.88    200.84
201.01    200.88
Course of intensity values:           95792   116615   117134    99225
81317   120617   124203
Indices of imputed values: 2  4
Predictive t-distribution:vau= 99.1, mu= 200.86, sigma2= 0.0117
Predictive 95%-mass-window: [200.64 201.07]
```

Grouping protocol – page 96

```
-------------------------------------------------------
Position of peak: Scan34MZ202
Course of mass-to-charge values:     202.42    202.29    202.42    202.16
202.33    202.16    202.16
Course of intensity values:           53967   128869     98365    50979
37719    30349    24187
Indices of imputed values: 5
Predictive t-distribution:vau= 99.1, mu= 202.28, sigma2= 0.0121
Predictive 95%-mass-window: [202.06 202.50]

-------------------------------------------------------
Potential peaks with 26 observation(s)
-------------------------------------------------------
Number: 1
-------------------------------------------------------
→ Position of peak: Scan34MZ205
Course of mass-to-charge values:     204.73    204.86    204.86    204.86
204.86   204.99   204.99   204.99   204.99   204.99
204.99   204.86   204.86   204.86   204.86   204.86
204.99   204.99   204.99   204.99
Course of intensity values:           34040   227453   166698   215617
455769   456323   949309  1054378  1286662
1563009  1597857  1567542  1205349  1549879
1322807  1234574   873526   733510   787308   752379   399262
164562
Indices of imputed values:
Predictive t-distribution:vau= 118.1, mu= 204.92, sigma2= 0.0100
Predictive 95%-mass-window: [204.72 205.12]
```

Fig. 74

Grouping protocol – page 97

35. scan

Table of observations at scan time 972.76 Seconds
in mass-to-charge window 200.00-205.00 Da Mass-to-charge: m/z [Da]
Intensity: I [cts]

| m/z | I | m/z | I | m/z | I | m/z | I | m/z | I |
|---|---|---|---|---|---|---|---|---|---|
| 200.75 | 111084 | 201.91 | 24460 | 202.16 | 58179 | 203.06 | 49406 | | |
| 203.83 | 293847 | | | | | | | | |

Total number of observations: 5

Grouping protocol – page 98

Potential peaks that get updated because some observation
fell in their predictive mass-window for 2 scans Listed by their identifiers and results Scan34MZ201: all data points were used to update (intensity too small)
Scan34MZ202: all data points were used to update (intensity too small)
Scan34MZ203: all data points were used to update (less than four)
Scan34MZ204: all data points were used to update (less than four)

Resulting potential peaks after the 35. Scan

Total number: 6

Potential peaks with 1 observation(s)

Number: 1
--------
Position of peak: Scan35MZ202
Course of mass-to-charge values:   201.91
Course of intensity values:         24460
Indices of imputed values:
Predictive t-distribution:vau= 93.1, mu= 201.91, sigma2= 0.0207
Predictive 95%-mass-window: [201.62 202.19]

Potential peaks with 2 observation(s)

Number: 1
--------
Position of peak: Scan35MZ204
Course of mass-to-charge values:   203.70   203.83
Course of intensity values:         57569   293847
Indices of imputed values:
Predictive t-distribution:vau= 94.1, mu= 203.77, sigma2= 0.0155
Predictive 95%-mass-window: [203.52 204.02]

Potential peaks with 3 observation(s)

Number: 1
--------
Position of peak: Scan35MZ203
Course of mass-to-charge values:   202.93   202.93   203.06
Course of intensity values:         33380   132497   49406
Indices of imputed values:
Predictive t-distribution:vau= 95.1, mu= 202.96, sigma2= 0.0137
Predictive 95%-mass-window: [202.75 203.21]

Potential peaks with 8 observation(s)

Number: 2
--------
Position of peak: Scan35MZ201
Course of mass-to-charge values:   200.75   200.88   200.84
   201.01      200.75      200.88      200.75

Fig. 75

```
Grouping protocol - page 99

Course of intensity values:
81317     120617    124203      95792    116615    117134     99225
Indices of imputed values: 2 4
Predictive t-distribution:vau= 100.1, mu= 200.84, sigma2= 0.0115
Predictive 95%-mass-window: (200.63 201.06]

Position of peak: Scan35MZ202
Course of mass-to-charge values:            202.42             202.16      202.16
202.33    202.16    202.16
Course of intensity values:
17719      30349     24187      53967    128869     98365     50979
Indices of imputed values: 5
Predictive t-distribution:vau= 100.1, mu= 202.27, sigma2= 0.0119
Predictive 95%-mass-window: [202.05 202.48]

Potential peaks with 26 observation(s)

Number: 1
Position of peak: Scan35MZ205
Course of mass-to-charge values:
204.86    204.99    204.99    204.73    204.73    204.86    204.86
204.99    204.99    204.86    204.99    204.99    204.99    204.86
204.99    204.99    204.86    204.99    204.99    204.86    204.99
204.86
Course of intensity values:
401424    455769    456323     34040    227453    166598    215617
1320664   1563009   1597857    868147    949309   1054378   1286662
1322807   1234574   1418667   1567542   1205349   1418667   1549879
164562              873526    733510    787308    752379    399262
Indices of imputed values:
Predictive t-distribution:vau= 118.1, mu= 204.92, sigma2= 0.0100
Predictive 95%-mass-window: (204.72 205.12]
```

```
Grouping protocol - page 100

36. scan

Table of observations at scan time 974.86 Seconds
in mass-to-charge window 200.00-205.00 Da Mass-to-charge: m/z [Da]
Intensity: I [cts]

m/z    I    |  m/z     I    |  m/z     I    |  m/z     I    |  m/z     I
200.88  113648| 202.68  38262 | 203.32  30760 | 203.83  104339
204.60  305594|

Total number of observations: 5
```

Fig. 76

$$= \left[m/z_{ion} - \Delta m/z_{dev},\ m/z_{ion} + \Delta m/z_{dev}\right]$$

$$\left[t_{ion} - \Delta t_{dev},\ t_{ion} + \Delta t_{dev}\right] = \left[918.74,\ 970.96\right]$$

$$\left[N_{ion} - \Delta N_{dev},\ N_{ion} + \Delta N_{dev}\right] = \left[9,\ 34\right]$$

Grouping protocol - page 101

```
Potential peaks that get updated because some observation
fell in their predictive mass-window for 2 scans
------------------------------------------------------------
Listed by their identifiers and results
------------------------------------------------------------
Scan35MZ201: all data points were used to update (intensity too small)
Scan35MZ204: all data points were used to update (less than four)

Potential peaks that get closed because no observation
fell in their predictive mass-window for 2. scans
------------------------------------------------------------
Listed by their identifiers and results
------------------------------------------------------------
Scan35MZ205 fulfilled the requirements of some peak Resulting potential peaks after the 36. Scan
------------------------------------------------------------

Total number: 8

Potential peaks with 1 observation(s)
------------------------------------------------------------
Number: 4
------------------------------------------------------------
Position of peak: Scan36MZ202                201.91
Course of mass-to-charge values:     201.91
Course of intensity values:          24460
Indices of imputed values:
Predictive t-distribution:vau= 93.1, mu= 201.91, sigma2= 0.0207
Predictive 95%-mass-window: [201.62 202.19]
------------------------------------------------------------
Position of peak: Scan36MZ203                202.60
Course of mass-to-charge values:     202.60
Course of intensity values:          38262
Indices of imputed values:
Predictive t-distribution:vau= 93.1, mu= 202.68, sigma2= 0.0207
Predictive 95%-mass-window: [202.39 202.96]
------------------------------------------------------------
Position of peak: Scan36MZ203                203.32
Course of mass-to-charge values:     203.32
Course of intensity values:          30760
Indices of imputed values:
Predictive t-distribution:vau= 93.1, mu= 203.32, sigma2= 0.0207
Predictive 95%-mass-window: [203.03 203.61]
------------------------------------------------------------
Position of peak: Scan36MZ205                204.60
Course of mass-to-charge values:     305594
Course of intensity values:
Indices of imputed values:
Predictive t-distribution:vau= 93.1, mu= 204.60, sigma2= 0.0207
Predictive 95%-mass-window: [204.32 204.89]
------------------------------------------------------------

Potential peaks with 3 observation(s)
------------------------------------------------------------
Number: 2
------------------------------------------------------------
```

Grouping protocol - page 102

```
Position of peak: Scan35MZ203
Course of mass-to-charge values:    202.93    202.93    203.06
Course of intensity values:         33380    132497    49406
Indices of imputed values:
Predictive t-distribution:vau= 95.1, mu= 202.98, sigma2= 0.0137
Predictive 95%-mass-window: [202.75 203.21]
------------------------------------------------------------
Position of peak: Scan35MZ204
Course of mass-to-charge values:    203.70    203.83    203.83
Course of intensity values:         57569    293847   104339
Indices of imputed values:
Predictive t-distribution:vau= 95.1, mu= 203.79, sigma2= 0.0137
Predictive 95%-mass-window: [203.56 204.02]
------------------------------------------------------------

Potential peaks with 8 observation(s)
------------------------------------------------------------
Number: 1
------------------------------------------------------------
Position of peak: Scan35MZ202
Course of mass-to-charge values:    202.42    202.16    203.29    202.42    202.16
                                    202.33    202.16
Course of intensity values:         53967    128869    98365    50979
                                    37719    30349     24187    58179
Indices of imputed values: 5
Predictive t-distribution:vau= 100.1, mu= 202.27, sigma2= 0.0119
Predictive 95%-mass-window: [202.05 202.48]
------------------------------------------------------------

Potential peaks with 9 observation(s)
------------------------------------------------------------
Number: 1
------------------------------------------------------------
Position of peak: Scan36MZ201
Course of mass-to-charge values:    200.75    200.88    200.88    200.84
                                    201.01    200.75    200.88    117134    99225
Course of intensity values:         95792    116615    113648
                                    81317    120617    124203
Indices of imputed values: 2 4
Predictive t-distribution:vau= 101.1, mu= 200.85, sigma2= 0.0112
Predictive 95%-mass-window: [200.64 201.06]
```

Fig. 77

Grouping protocol – page 103

---
37. scan
---
Table of observations at scan time 976.96 Seconds
in mass-to-charge window 200.00-205.00 Da
---
Mass-to-charge: m/z [Da]
Intensity: I [cts]

| m/z | I | m/z | I | m/z | I | m/z | I |
|---|---|---|---|---|---|---|---|
| 200.63 | 128739 | 202.93 | 114817 | | | | |

Total number of observations: 2

Grouping protocol – page 104

---
Potential peaks that get updated because some observation
fell in their predictive mass-window for 2 scans
---
Listed by their identifiers and results
---
Scan36MZ203: all data points were used to update (intensity too small)
---
Potential peaks that get closed because no observation
fell in their predictive mass-window for 2. scans
---
Listed by their identifiers and results
---
Scan36MZ202: intensity of 24460 is smaller than required 485489
---
Resulting potential peaks after the 37. Scan
---
Total number: 7
---
Potential peaks with 1 observation(s)
---
Number: 4
---
Position of peak: Scan37MZ203
Course of mass-to-charge values:       202.68
Course of intensity values:       38262
Indices of imputed values:
Predictive t-distribution:vau= 93.1, mu= 202.68, sigma2= 0.0207
Predictive 95%-mass-window: [202.39 202.96]
---
Position of peak: Scan37MZ203
Course of mass-to-charge values:       203.32
Course of intensity values:       30760
Indices of imputed values:
Predictive t-distribution:vau= 93.1, mu= 203.32, sigma2= 0.0207
Predictive 95%-mass-window: [203.03 203.61]
---
Position of peak: Scan37MZ205
Course of mass-to-charge values:       204.60
Course of intensity values:       305594
Indices of imputed values:
Predictive t-distribution:vau= 93.1, mu= 204.60, sigma2= 0.0207
Predictive 95%-mass-window: [204.32 204.89]
---
Position of peak: Scan37MZ201
Course of mass-to-charge values:       200.63
Course of intensity values:       128739
Indices of imputed values:
Predictive t-distribution:vau= 93.1, mu= 200.63, sigma2= 0.0207
Predictive 95%-mass-window: [200.34 200.91]
---
Potential peaks with 3 observation(s)
---
Number: 1
---
Position of peak: Scan37MZ204

Fig. 78

METHOD AND SYSTEM FOR PROCESSING MULTI-DIMENSIONAL MEASUREMENT DATA

CROSS-REFERENCE TO RELATED APPLICATIONS

This application claims priority under 35 U.S.C. §119, via the Paris Convention for the Protection of Industrial Property, to European patent application number 04009709.9, filed Apr. 23, 2004, which is hereby incorporated by reference.

FIELD OF THE INVENTION

This invention relates to sample analysis and preprocessing of data using a plurality of analyzing techniques to generate and group data tuples into intervals.

BACKGROUND OF THE INVENTION

Data preprocessing aimed at reducing the amount of data and extracting relevant information from multi- or high-dimensional data is a step of many data analysis techniques. For example, a Liquid Chromatography/Mass Spectrometry (LC-MS) data set may consist of several hundred scans with a broad mass range, e.g., from app. 50-100 Da to several thousand Da (typically 2000-10000 Da) expressed in mass/charge (m/z) values. A data set of a single measurement consists of millions of data points that include a significant amount of information with little or no value. (e.g., Both electrical and chemical noise, non-relevant 'real' signals coming from mobile phase components, ion source contamination, signals of bleeding of chromatographic material). Due to the number of data points, a manual selection of relevant information is not imaginable, at least in practical applications; therefore a technological approach using a suitable algorithm is necessary.

For many 2-dimensional, 3-dimensional or even higher dimensional data sets, like LC-MS data, run-to-run variation on within the dimensions is observed as having a detrimental effect on pattern recognition analysis. A correct allocation of signals of the same substance in a collective of data sets (like measurements of more than one sample) is an important premise of a proper pattern recognition application. A false assignment of peaks to a chemical individual within the pattern reduces the possibility to find the 'true' pattern.

In an LC-MS data set, the variability of retention times can have various causes, such as inhomogeneity of gradient formation, fluctuation of flow-rate, overloading of the chromatographic column, chemical and mechanical changes due to the ageing of the chromatographic materials. The variability of mass/charge measurement depends on factors such as the accuracy of the mass detection, mass-to-charge value, intensity values or the signal/noise ratio, the generating of centroided spectra from continuous ones.

Many chemometric methods deal with data preprocessing of LC-MS data. The majority of these methods extract an informative part of data sets using an algorithm analyzing the data in one-dimension only. Some of the methods analyze the data in both dimensions simultaneously resulting in substantially higher quality of preprocessed data.

Other Approaches

1) J. Chromatogr A 771, 1997, 1-7: "Application of sequential paired covariance to liquid chromatography-mass spectrometry data; Enhancements in both the signal-to-noise ratio and resolution of analyte peaks in the chromatogram", David C. Muddiman et al. The article provides that a sequential paired covariance (SPC) method generates a series of virtual amplified mass spectra. Each data point in a mass spectrum is multiplied with the corresponding data point from the following mass spectrum—resulting in a geometrically amplified spectrum; the number of spectra used in each multiplication operation defines the order of the covariance algorithm. Thus, dramatic enhancement of the S/N ratio and the resolution in the chromatogram is achieved; however the algorithm can be used for qualitative analysis only because the absolute quantitative information (both peak area and height) is getting lost by multiplying the consecutive data point.

2) Analytica Chemica Acta 446, 2001, 467-476: "Fast interpretation of complex LC-MS data using chemometrics", W. Windig at al.

3) U.S. Pat. No. 5,672,869 entitled "Noise and background reduction method for component detection in chromatography/spectrometry" provides a component detection algorithm (CODA) that extracts from LC-MS data a compound's information by random noise, spikes and mobile phase peaks elimination. It uses the assessment of differences between original chromatogram and its smoothed form for spiked elimination using a similarity index having a value between 0 and 1 that is user specified. In order to detect a chromatogram representing solvent background, a comparison of an average value of all data points within the selected mass chromatogram was used.

4) J Chromatogr A 849, 1999, 71-85: "Windowed mass selection method: A new data processing algorithm for liquid chromatography-mass spectrometry data", C. M. Fleming et al. In the reference, a method termed 'windowed mass selection method' (WMSM) is shown to eliminate random noise that occurs in the data. The preprocessing method consists of two steps to remove random background noise, and is based on the main assumption that analytes can be distinguished from noise by means of differences in peak width. The disclosed system makes a number of assumptions including:

1. Any peak has a non-zero signal over the length of the window.
2. A characteristic of random noise is that it does not have a constant signal over a number of scans defined by a window, but intermittently displays zero-amplitude intensities. Multiplication of intensities over a window range will result in zero signal.
3. A low consistent background is removed by subtraction of a mean value of each chromatogram from this chromatogram.
4. Mobile phase peaks are removed by selection criteria which set the maximum length of a theoretical peak. If the peak is longer than the maximum allowed value it will be removed from data set.

The assumptions of this method do not include many eventualities occurring in the LC-MS data set (e.g. overlapping peaks, long noisy regions with fluctuating intensity values). A benefit over SPC method could be, in principle, preservation of absolute intensity values. However, those intensities would require correction of the intensity values after background subtraction.

5) Singular value decomposition method: The singular value decomposition method (SVD) is a method for data compression and noise reduction by eigenvalue-like decomposition for rectangular matrices. Characteristics of this method are provided in Fleming et al.; J Chromatogr A 849, 1999, 71-85 and in references cited therein.

6) WO 02/13228 A2 (Method and system for identifying and quantifying chemical components of a mixture, Vogels et al.) discloses a method of data processing and evaluation consisting of the steps of smoothing the data point of chromatogram and determining an entropy value for a smoothed chromatogram (chromatogram may be either a selected mass or total ion chromatogram). After evaluation of a quality factor (based on an entropy value) for each smoothed mass chromatogram in the data set, the algorithm generates a reconstructed total ion chromatogram from selected mass chromatograms with the IQ values above a defined threshold value.

7) U.S. Pat. No. 5,995,989 A1 (Method and apparatus for compression and filtering of data associated with spectrometry, Gedcke et al.) discloses a method and apparatus for compression and filtering of data associated with spectrometry. The method monitors a value of each data point and compares it to the previously data point to determine whether it is on or very near a peak. The intensity values for a designated number of data are summed and averaged to determine the average of a noisy background. A threshold is determined by multiplying the deviation by a empirically defined constant k, each data point is compared to this threshold value.

8) US 2002/0193950 A1 (Method for analyzing mass spectra, Gavin et al.) discloses a method that analyzes mass spectra. The analysis consists of detecting signals above S/N cutoff, clustering of signals, pre-selection of features, identification mass values for selected clusters, creating of a classification model and assignment of unknown sample. This method is predestined for 1-dimensional signals, like MALDI, SELDI or ESI-MS spectra without a time-dependent separation prior the chromatographic detection.

The document focuses on a classification model having classes characterized by different biological status. In this context a feature pre-selection using a cluster analysis is described. Signal clusters having a predetermined number of signals (here: biological samples in which the signal is present) are selected for the classification model, clusters having less signals are discarded.

The possibility of preprocessing raw data is considered only briefly in the document. To this end it is mentioned that the data analysis could include the steps of determining the signal strength (e.g. height of signals) of a detected marker and to remove "outliers" (data deviating from predetermined statistical distribution).

9) US 2003/0040123 A1 (Peak selection in multidimensional data, Hastings) discloses a method of computing local noise thresholds for each one-dimensional component of the data. Each point has a local noise threshold applied to it for each dimension of the data set, and a point is selected as a peak candidate only in the case its value exceeds all of the applied local noise thresholds. Contiguous candidate peaks are clustered into actual peaks (i.e., detected real chromatographic peaks).

A noise threshold can be computed from a window of points surrounding the particular point. After peak picking, additional criteria can be applied to the peaks before they are accepted into a peak database. With respect to the selection of actual peaks it is considered that additional peak recognition algorithms, such as line shape analysis or Bayesian/maximum likelihood analysis for mass chromatograms or isotope distribution analysis for mass spectra may also be applied. Details are not given. With respect to the peak picking it is also considered that the noise could be reduced by using a suitable filter on the basis of a known noise distribution, so that peaks can be detected. The method disclosed in US 2003/0040123 A1 addresses the noise issue, in particular the particularities of noise in LC-MS data, by applying different noise thresholds to different dimensions of the data.

Review Articles of General Interest

A review of so-called data mining techniques which can be used for example with respect to mass spectrometry data can be found in Current Opinion in Drug Discovery & Development 2001 4(3), 325-331, "Data mining of spectroscope data for biomarker discovery" S. M. Norton et al. Of general interest is also the review article IEEE Transactions on Pattern Analysis and Machine Intelligence, 22(1), 2000, 4-37: "Statistical Pattern Recognition: A Review", A. K. Jain et al., which considers issues such as feature extraction and selection, cluster analysis and generally so-called data mining on the basis of statistical methods including Bayesian statistics.

PROBLEMS OF THE ART

Some drawbacks of algorithms in the context of LC-MS spectrometry generally are:

1. All information needed for the peak picking (noise elimination, spikes identification, mobile phase clusters erasing) is to be based upon the analysis of a particular single data set. Acquired information of the data properties will not be transferred to the next data set, thus a starting of a new peak picking process for the next data set is necessary.

2. Most of the algorithms do not preserve the knowledge about the inaccuracy of retention time and mass/charge values for a particular peak. This may be important for a correct allocation of signals of the same substances (peaks) in a collective of data sets to be analyzed by pattern recognition method. A false assignment of peaks to identical substances within the pattern may lead to false positive or negative results.

3. Most of the described methods assume very accurate mass-to-charge values which do not reflect the reality. The m/z values of a single peak eluting over a period of time show the inaccuracies originating in the mass accuracy of the MS analyzer, mass shift of the centroided mass values in comparison to the original values of noisy peaks.

Such "hard binning" of data into mass traces does not bear in mind the fact that real molecules may vary on the first decimal place in measured mass-to-charge ratio. This could lead to the splitting of a peak into the consecutive traces due to the measurement inaccuracy of the mass axis, which leads to the following errors:

wrong allocation of the bins to peaks, wrong total intensity values in peaks, gaps occurring in the retention time axis may even lead to the right peak not being recognized as a peak at all.

Even in the case of higher mass accuracy of measurement (like in TOF analyzer), there are several reasons leading to the overlapping of the detected signals and subsequently leading to the incorrect allocation of data points to the respective peaks (bins), e.g. overlapped signals of isotopes at higher charge states, incompletely chromatographic separated substances with very similar molecular weights.

In the case of the selection of "broad" mass traces there is a risk of pooling data points from various peaks into a single bin, on the other hand the selection of very "narrow" mass traces causes splitting of a single peak into two or more bins.

4. Most of the described methods perform the peak picking along the mass traces with defined Δm/z (by default 0.5-1 Da for data from quadruple analyzers, Δm/z 0.1-0.01 for data from TOF analyzers). Usually, an operator evaluates acquired data on the basis of some initial information about the mass accuracy and the position of relevant information in a data set.

However, for the pattern recognition analysis of large collectives of very complex samples, like LC extracts of serum or urine samples, tissue homogenates extracts, cell culture media, the strategy of peak picking along the mass traces leads to extensive computing time. Apart from the problem with the splitting of a peak into two consecutive mass traces, this is a very tedious strategy for data preprocessing of complex data sets because without knowing the initial information about the position of informative signals one needs to screen every mass trace regardless of its information content.

5. Most of the described methods perform the noise reduction on a single mass trace (m/z value) and they do not characterize general properties of noise over the complete data set. Together with the conventional "hard binning" there is the danger that informative data points are deleted.

OBJECT AND SOLUTION

It is an object of various embodiments of the invention to provide a method which is suitable for an effective data processing or data preprocessing of multi-dimensional measurement data to differentiate between non-informative and informative data information. In particular, the inventions aims at providing the basis for overcoming at least some of the drawbacks of existing approaches mentioned.

SUMMARY

A summary is provided with reference to a non-limiting illustrative example, namely with reference to a combination of liquid chromatography with ionization mass spectrometry (e.g. electrospray ionization mass spectrometry) and corresponding measurement data. Such data generally have three dimensions, namely a first dimension relating to the retention time of a respective substance in a chromatography column, a second dimension relating to the mass-to-charge ratio of respective ions and a third dimension relating to an ion intensity or ion count number measured for a certain retention time and a certain mass-to-charge ratio, i.e. with respect to a (retention time, mass-to-charge ratio)-coordinate. The retention time of a certain substance in a column is generally expressed in terms of a scan number identifying a respective measurement scan of the mass spectrometer or by the detection time for which a certain ion intensity was detected, having a certain mass-to-charge ratio. For analyzing a respective sample or a number of samples on the basis of such measurement data, a grouping of the data identifying those data points which can be attributed to the same substance (constituent of the sample of resulting product) is necessary. This conventionally was done by an operator or scientists looking at a visual representation of the data on the basis of experience and which the prior art attempts effect by different peak picking and pattern recognition algorithms.

The data points originating from the same substance are located in a certain scan number interval or detection time interval and a certain mass-to-charge ratio interval. Such a scan number interval may be denoted as $[N_{ION}-\Delta N_{dev}, N_{ION}+\Delta N_{dev}]$, such a detection time interval may be denoted as $[t_{ION}-\Delta t_{dev}, t_{ION}+\Delta t_{dev}]$ and such a mass-to-charge ratio may be denoted as $[m/z_{ION}-\Delta m/z_{dev}, \Delta m/z_{ION}+\Delta m/z_{dev}]$, wherein $N_{ION}$, $t_{ION}$ and $m/z_{ION}$ are generally only a central value of a respective measurement value interval having the boundaries $N_{ION}-\Delta N_{dev}$, $N_{ION}+\Delta N_{dev}$ or $t_{ION}-\Delta t_{dev}$, $t_{ION}+\Delta t_{dev}$ or $m/z_{ION}-\Delta m/z_{dev}$, $m/z_{ION}+\Delta m/z_{dev}$. However, for better understanding, one might assume that the values $N_{ION}$, $t_{ION}$ and $m/z_{ION}$ are the true or characteristic or average (mean) scan number, detection time or mass-to-charge ratio measured for a certain substance, which, however, corresponds to the central value of the respective interval only if the individual data points are symmetrically distributed around the average or true value.

In this summary and explanation of the embodiments references are included such as the references SCAN NUMBER (referring to the mentioned scan number) and, as an alternative, the reference DETECTION TIME (referring to the detection time), together with the reference MASS-TO-CHARGE RATIO (referring to the mass-to-charge ratio) and, if applicable, the reference ION INTENSITY (referring to the ion intensity or, alternatively, an ion count) measured by means of a mass spectrometer. Further are included as references respective measurement value intervals in said representations as mentioned, together with respective measurement values $N_i$ and $t_i$ for the scan number and the detection time (these are alternatives, which might be used), respective measurement values $m/z_i$ for the mass-to-charge ratio and, if applicable, respective measurement values $I_i$ for the ion intensity.

Some other references based on this non-limiting illustrative example are included further, the meaning thereof should be obvious in the respective context: E.g. $N_{ION}$; $t_{ION}$ (referring to a true or characteristic or mean scan number or detection time, respectively, of a respective ion), $m/z_{ION}$ (referring to a true or characteristic or mean mass-to-charge ratio of a respective ion), $\Delta m/z_i$ (referring to a deviation of a respective measurement value for the mass-to-charge ratio from the true or characteristic or mean mass-to-charge ratio of the respective ion). The references are included similar to the conventional practice with respect to the insertion of reference signs in claims. Accordingly, references separated by "comma" have to be seen as a list of references which generally might be applicable in common and references separated by "semicolon" have to be seen as a list of references which generally are applicable as alternatives.

It should be stressed the point, that these references are intended only to facilitate the understanding of the invention and that for other measurement situations and other analytical and detection techniques of course other terms and references would have to be introduced instead of the references and terms used.

A further remark: In the following it is tried to thoroughly distinguish between a quantity (or variable) or quantities (or variables) to be measured or determined and the value or values measured or determined for respective quantity or variable. E.g., if a certain electrical voltage would be of interest, then the quantity or variable VOLTAGE would be addressed as QUANTITY and a voltage value (e.g. having the unity "volt") obtained from a respective measurement or determination would be addressed as VALUE. In the non-limiting examples considered in the foregoing the terms SCAN NUMBER, DETECTION TIME, MASS-TO- CHARGE RATIO and ION INTENSITY refer to QUANTITIES in this sense and the terms $N_i$, $t_i$, $m/z_i$ and $I_i$ refer to VALUES in this sense. These distinctions serve basically to facilitate the understanding and should in any case not be considered to have a limiting effect on the scope of the invention.

Proposal 1: A first aspect provides a method for analyzing at least one sample by effecting two or more techniques to provide characterization data which characterizes said sample with respect to at least one of its constituents, in particular chemical, biological or biochemical constituents contained therein and products resulting from effecting at least one of said techniques, said method comprises the steps of:
  a) effecting at least one first analytical technique
    i) to separate constituents or
    ii) to separate products resulting from effecting said first analytical technique or at least one first analytical technique or
    iii) to separate constituents and products resulting from effecting said first analytical technique or at least one first analytical technique,
    said first analytical technique being effected with respect to said sample or with respect to constituents or products already separated, said separation being effected on the basis of at least one first differentiating characteristic of said constituents or products;
  b) effecting at least one further technique with respect to constituents or products already separated or in the course of being separated, said further technique being at least one of an analytical and detection technique, to characterize separated constituents or products on the basis of at least one of i) at least one separation obtained from effecting step a) at least once and ii) at least one further differentiating characteristic;
  wherein at least in step b) detection hardware is used which provides measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIME) of said characterizing measurement quantities reflecting said or at least one separation obtained from effecting step a) at least once and at least one further (MASS-TO-CHARGE RATIO) of said characterizing measurement quantities reflecting at least one of i) at least one other separation obtained from effecting step a) at least once and ii) said further differentiating characteristic or at least one further differentiating characteristic;
  wherein said method further comprises the steps of:
  c) providing data tuples $((N_i, m/z_i); (t_i, m/z_i))$ on the basis of the measurement data provided by the detection hardware by associating to each other at least one respective first characterizing measurement value representing said characterization or at least one characterization in terms of said at least one first (SCAN NUMBER; DETECTION TIME) of said characterizing measurement quantities and at least one respective further characterizing measurement value representing said characterization or at least one characterization in terms of said at least one further (MASS-TO-CHARGE RATIO) of said characterizing measurement quantities;
  d) grouping said data tuples into characterizing measurement value intervals of characterizing measurement values with respect to the characterizing measurement values for at least one of said characterizing measurement quantities, said intervals each being determined to potentially be associated to one particular of said constituents or products;
  wherein said grouping is effected on the basis of at least one statistical distribution of deviations ($\Delta m/zi$) of the respective characterizing measurement values from a true or characteristic or mean characterizing measurement value (m/zION) associated to said particular of said constituents or products;
  wherein said method further comprises at least one of the steps of:
  e) at least one of storing, displaying and printing of data or visualizations of data which reflect or include at least one of i) groups of data tuples obtained from said grouping and ii) intervals of said at least one of said characterizing measurement values obtained from said grouping;
  f) further analysis of said at least one sample or of at least one of said constituents or products on the basis of at least one of i) groups of data tuples obtained from said grouping and ii) intervals of said at least one of said characterizing measurement values obtained from said grouping or on the basis of data or visualizations stored, displayed or printed according to step e).

According to the embodiment, the grouping of the measurement data is effected on the basis of at least one statistical distribution of deviations of the respective characterizing measurement values from a true or characteristic or mean characterizing measurement value which is associated to a particular of the constituents or products. Using this approach, very effective grouping can be achieved. Referring to the example LC-Mass-Spectroscopy (LC-MS analysis), this approach can be adopted with the advantage of determining relevant intervals for the mass-to-charge data parts, i.e. to find relevant intervals along a mass-to-charge ratio axis of a corresponding coordinate system which may be defined with respect to the measurement data. In this context orthodox or conventional statistics as well as Bayesian statistics or non-frequency-based statistics may be used.

It should be pointed out that step a) may be effected several times simultaneously or sequentially. Step b) may include a separation similar to the separation according to step a), or may at least be adapted to effect such a separation. An example is mass spectroscopy which is adapted to effect a separation. If, however, the different substances are already separated then effecting mass spectroscopy with respect to said substances does not necessarily give rise to an additional separation but instead serves perhaps only to map the substances on the m/z axis for a certain detection time or scan number reflecting the separation effected in step a), possibly by using at least one chromatographic column or the like.

Also step b) could be effected several times simultaneously or sequentially. Further, depending on the measurement situation and the techniques used it may be possible to effect step b) simultaneously or overlapping with step a). An example is electrophoresis which uses online detection of the electrophoretic bands by means of induced fluorescence. In such a measurement situation the electrophoresis separates substances. On the basis of this separation measurement data representing said separation may be obtained in accordance with step b).

Another possibility is that also step a) includes the use of detection hardware to provide measurement data. Again, it may be referred to the example of electrophoresis with online detection of the electrophoresis bands which may be detected by appropriate means. On the basis of the obtained separation an additional characterization, beside the characterizations obtained from detecting the fluorescent bands, may be obtained in accordance with step b).

With respect to step c) it should be noted, that there are many possible ways to organize the data. In general, it is sufficient that the characterizing measurement values of a respective data tuple can be identified with respect to their association to each other and to the respective characterizing measurement quantity, so that these characterizing measurement values may be accessed for the grouping. Accordingly, the term "data tuple" and the association of the characterizing measurement values to each other has to be understood functionally and shall comprise any possible data organization which implements or reflects or allows such associations and possibilities of access.

Also, steps c) and d) may be effected simultaneously, and possibly interleaved. The same applies to steps d) and e). Further, step d) or/and step e) on the one hand and step f) on the other hand may be effected simultaneously, possibly interleaved.

It should be noted, that generally said intervals are determined to be indeed associated to one particular of said constituents or products. The working hypothesis of the grouping is that the grouping is effective to determine intervals which each are associated to one particular of said constituents or products. However, not always it is possible to rule out wrong determinations if there are artifacts or if not the optimum analytical and detection techniques are used. If the possibility of errors is taken into account, then the grouping determines intervals which are potentially associated to one particular of said constituents or products. Whether these intervals are indeed associated to one particular of said constituents or products may be determined in an additional verification step, possibly taking into account present knowledge about the sample or group of samples to be analyzed and reference data included in a reference database.

With respect to step e) should be added, that preferably only data or visualizations of data which reflect or include groups of data tuples obtained from said grouping or/and intervals of respective characterizing measurement values obtained from said grouping are stored or/and displayed or/and printed, and that other data not falling in the groups or intervals are discarded. This leads to a major data reduction. Additional reduction of data in the sense of some sort of data compression may be obtained if not the data tuple of a respective group or falling in a respective interval are stored but instead data describing the group or the interval, in the case of LC-MS data, e.g. an average m/z value, an average t value or N value and possibly a summarizing intensity value (e.g. the sum of all individual intensities, integral over the area under a curve defined by the data tuples, average intensity value, and the like). Additionally or alternatively to the average m/z value and t value or N value the m/z interval and t interval or N interval may be stored, possibly by storing the boundaries of the respective interval or by storing a central value and the width of the respective interval. However, it should be emphasized that such a data reduction and even data compression is not always necessary, in particular if large data storage space is available and if fast processors are available. Under such circumstances a grouping of the data as such may be of high value for facilitating the analysis of the data. E.g. data tuples belonging to the same group may be identified in a visualization of the data by attributing different colors to different groups, such as known from false color or phantom color representations, so that a qualitative analysis of the respective sample or samples is facilitated for the scientist or operator viewing the visualization on a display or on a printout.

At least said grouping according to step d) and generally also the storing, displaying and printing and the further analysis of step e) and generally also the provision of data tuples according to step c) will generally be effected automatically or automatized by a suitable data processing arrangement, e.g. data processing unit or data processing system, possibly by a general purpose computer or by the control unit of a measurement and analyzing system. Although it might be possible, that a scientist or operator inputs certain data which trigger certain actions or which are taken as basis for certain processing steps, the grouping as such will generally be effected without human interaction on the basis of measurement raw data obtained from effecting said techniques, possibly under the control of a program instructions embodiment of the invention.

Preferably, said grouping in step d) is effected on the basis of at least one statistical distribution of measurement deviations indicating a statistical distribution of deviations ($\Delta m/zi$) of the respective characterizing measurement values from a true or characteristic or mean characterizing measurement value (m/zION) associated to said particular of said constituents or products (proposal 2).

Further, it is suggested that said intervals correspond to intervals which according to said statistical distribution of deviations ($\Delta m/zi$) include a substantial amount of all respective characterizing measurement values which originate from said particular of said constituents or products (proposal 3).

To advantage said intervals may be prediction intervals which are predicted by said statistical distribution of deviations ($\Delta m/zi$) to include a substantial amount of all respective characterizing measurement values which originate from said particular of said constituents or products (proposal 4).

A highly effective grouping may be obtained if said intervals are prediction intervals, possibly confidence intervals, predicted by said statistical distribution of deviations ($\Delta m/zi$) on the basis of initialization data and, in the course of the grouping according to step d), on the basis of data tuples already grouped to include a substantial amount of all respective characterizing measurement values which originate from said particular of said constituents or products and belong to data tuples not already grouped (proposal 5). Preferably, Bayesian statistics is used in this context. To advantage so-called Bayesian learning or updating may be used to improve current characterizing measurement value intervals.

One may attribute dimensions to the data tuples provided according to step c). In this respect it is proposed that said data tuples are generated in step c) to include said at least one respective first characterizing measurement value ($N_i$; $t_i$) mapped on at least one first dimension of said data tuples and to include said at least one respective further characterizing measurement value ($m/z_i$) mapped on at least one further dimension of said data tuples (proposal 6). One may use to advantage data structures which reflect these dimensions, e.g. arrays having appropriate dimensionality.

With respect to step d) it is further proposed that in step d) said data tuples are grouped in characterizing measurement value intervals ([m/zION−$\Delta$m/zdev, m/zION+$\Delta$m/zdev], [$N_{ION}$−$\Delta N_{dev}$, $N_{ION}$+$\Delta N_{dev}$]; [m/zION−$\Delta$m/zdev, m/zION+$\Delta$m/zdev], [$t_{ION}$−$\Delta t_{dev}$, $t_{ION}$+$\Delta t_{dev}$]) with respect to the characterizing measurement values for at least two different characterizing measurement quantities, wherein said grouping is effected such that interval sets ([m/zION−$\Delta$m/zdev, m/zION+$\Delta$m/zdev], [$N_{ION}$−$\Delta N_{dev}$, $N_{ION}$+$\Delta N_{dev}$]; [m/zION−$\Delta$m/zdev, m/zION+$\Delta$m/zdev], [$t_{ION}$−$\Delta t_{dev}$, $t_{ION}$+$\Delta t_{dev}$]) including one characterizing measurement value interval for each of said at least two different characterizing measurement quantities are determined to potentially be associated to one particular of said constituents or products, wherein said grouping is effected on the basis of said at least one statistical distribution of deviations ($\Delta$m/zi) with respect to characterizing measurement value intervals ([m/zION–$\Delta$m/zdev, m/zION+$\Delta$m/zdev]) of characterizing measurement values for at least one of said characterizing measurement quantities (proposal 7). Referring to proposal 6, said characterizing measurement values associated to at least two different characterizing measurement quantities will be mapped on different dimensions of said data tuples.

Preferably, said grouping is effected on the basis of said at least one statistical distribution of deviations ($\Delta$m/zi) with respect to characterizing measurement value intervals ([m/zION–$\Delta$m/zdev, m/zION+$\Delta$m/zdev]) of further characterizing measurement values for said further characterizing measurement quantity or at least one further characterizing measurement quantity, said characterizing measurement value intervals ([m/zION–$\Delta$m/zdev, m/zION+$\Delta$m/zdev]) of further characterizing measurement values herein also being denoted as further characterizing measurement value intervals (proposal 8).

Depending on the measurement situation and the techniques used, said measurement data provided by said detection hardware sometimes, often or generally will include quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto. In this case said data tuples may include at least one respective quantitative measurement value. In this respect it is proposed that said data tuples ((Ni, m/$z_i$, Ii); (ti, m/$z_i$, Ii)) are provided by associating to each other said at least one respective first characterizing measurement value (Ni; ti), said at least one respective further characterizing measurement value (m/$z_i$) and at least one respective quantitative measurement value (Ii) representing said quantification or at least one quantification (ION INTENSITY) in terms of said at least one quantitative measurement quantity (ION INTENSITY) (proposal 9). In this case said data tuples may be generated in step c) to include said at least one respective first characterizing measurement value (Ni; ti) mapped on at least one first dimension of said data tuples, to include said at least one respective further characterizing measurement value (m/$z_i$) mapped on at least one further dimension of said data tuples and to include said at least one respective quantitative measurement value (Ii) mapped on at least one other dimension of said data tuples (proposal 10).

With reference to a second aspect of the invention it is additionally proposed that in step d) said grouping is effected further on the basis of at least one collective characteristic of a plurality of said quantitative measurement values (Ii) each belonging to a respective one of said data tuples (proposal 11).

In particular, said grouping may be effected to advantage on the basis of at least one collective characteristic comprising an overall quantitative measure value determined from said plurality of said quantitative measurement values (proposal 12). As overall quantitative measure value may serve for example an average quantitative measurement value for said plurality of quantitative measurement values or a sum or product of said quantitative measurement values of said plurality or the like. The sub-term "measure" in the term "overall quantitative measure value" means, that the overall quantitative measure value can serve as a measure which indicates an overall characteristic of said quantitative measurement values considered in combination. Accordingly, it is not ruled out that the overall quantitative measurement value decreases, if said quantitative measurement values or the average of some of said quantitative measurement values increases and vice versa. E.g., there might be a reciprocal relation between the overall quantitative measure value on one hand and the quantitative measurement values on the other hand.

Further, said grouping may be effected to advantage additionally or alternatively on the basis of at least one collective characteristic comprising a shape of at least one curve or histogram which is directly or indirectly defined by those data tuples which each include at least one respective of said plurality of said quantitative measurement values (proposal 13). In this respect it is considered that said shape of said at least one curve or histogram is defined by values sub tuples, possibly value pairs, of those data tuples, wherein said value sub tuples, possibly value pairs, each include at least said at least one respective of said plurality of said quantitative measurement values and at least one respective of said characterizing measurement values, said at least one respective characterizing measurement value representing at least one of said characterizations in terms of said at least one characterizing measurement quantity which is associated to said or at least one respective quantitative measurement quantity (proposal 14).

With reference to at least one of proposals 11 to 14 it is further proposed that in step d) said data tuples are grouped in characterizing measurement value intervals ([m/zION–$\Delta$m/zdev, m/zION+$\Delta$m/zdev], [$N_{ION}$–$\Delta N_{dev}$, $N_{ION}$+$\Delta N_{dev}$]; [m/zION–$\Delta$m/zdev, m/zION+$\Delta$m/zdev], [$t_{ION}$–$\Delta t_{dev}$, $t_{ION}$+$\Delta t_{dev}$]) with respect to the characterizing measurement values for at least two different characterizing measurement quantities, wherein said grouping is effected such that interval sets ([m/zION–$\Delta$m/zdev, m/zION+$\Delta$m/zdev], [$N_{ION}$–$\Delta N_{dev}$, $N_{ION}$+$\Delta N_{dev}$]; [m/zION–$\Delta$m/zdev, m/zION+$\Delta$m/zdev], [$t_{ION}$–$\Delta t_{dev}$, $t_{ION}$+$\Delta t_{dev}$]) including one characterizing measurement value interval for each of said at least two different characterizing measurement quantities are determined to be potentially associated to one particular of said constituents or products, wherein said grouping is effected on the basis of said collective characteristics of said plurality of said quantitative measurement values ($I_i$) with respect to characterizing measurement value intervals ([$N_{ION}$–$\Delta N_{dev}$, $N_{ION}$+$\Delta N_{dev}$]; [$t_{ION}$–$\Delta t_{dev}$, $t_{ION}$+$\Delta t_{dev}$]) of characterizing measurement values for at least one of said characterizing measurement quantities (proposal 15). Referring to proposal 10, said characterizing measurement values associated to at least two different characterizing measurement quantities will be mapped on different dimensions of said data tuples.

To advantage said grouping may be effected on the basis of said collective characteristics of said plurality of said quantitative measurement values ($I_i$) with respect to characterizing measurement value intervals ([$N_{ION}$–$\Delta N_{dev}$, $N_{ION}$+$\Delta N_{dev}$]; [$t_{ION}$–$\Delta t_{dev}$, $t_{ION}$+$\Delta t_{dev}$]) of first characterizing measurement values for said first characterizing measurement quantity or at least one first characterizing measurement quantity, said characterizing measurement value intervals ([$N_{ION}$–$\Delta N_{dev}$, $N_{ION}$+$\Delta N_{dev}$]; [$t_{ION}$$\Delta t_{dev}$, $t_{ION}$+$\Delta t_{dev}$]) of first characterizing measurement values herein also being denoted as first characterizing measurement value intervals (proposal 16).

With reference to proposals 9 to 16 it is further suggested that said data stored, printed or displayed in step e) include quantitative information representing said quantification or at least one quantification in terms of said quantitative measurement quantity or at least one quantitative measurement quantity (proposal 17). Further it is suggested that for each group of data tuples obtained from said grouping at least one respective cumulative quantitative value is derived on the basis of the quantitative measurement values included in the data tuples of the respective group to represent said quantification or at least one quantification in terms of said quantitative measurement quantity or at least one quantitative measurement quantity (proposal 18). E.g., an average quantitative value or a sum of quantitative values may be used as cumulative quantitative value. Preferably, in step e), the respective cumulative quantitative value is stored instead of the quantitative measurement values on which the cumulative quantitative value is based (proposal 19). Substantial data compression may be obtained. It is referred to the above remarks concerning step e) of proposal 1.

According to a second aspect (addressed in the context of proposal 11) an embodiment provides (proposal 20) a method for analyzing at least one sample by effecting two or more techniques to provide characterization data which characterize said sample with respect to at least one of constituents, in particular chemical, biological or biochemical constituents contained therein and products resulting from effecting at least one of said techniques, said method comprising the steps of:

a) effecting at least one first analytical technique
   i) to separate constituents or
   ii) to separate products resulting from effecting said first analytical technique or at least one first analytical technique or
   iii) to separate constituents and products resulting from effecting said first analytical technique or at least one first analytical technique,
   said first analytical technique being effected with respect to said sample or with respect to constituents or products already separated, said separation being effected on the basis of at least one first differentiating characteristic of said constituents or products;

b) effecting at least one further technique with respect to constituents or products already separated or in the course of being separated, said further technique being at least one of an analytical and detection technique, to characterize separated constituents or products on the basis of at least one of i) at least one separation obtained from effecting step a) at least once and ii) at least one further differentiating characteristic;

wherein at least in step b) detection hardware is used which provides measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIME) of said characterizing measurement quantities reflecting said or at least one separation obtained from effecting step a) at least once and at least one further (MASS-TO-CHARGE RATIO) of said characterizing measurement quantities reflecting at least one of i) at least one other separation obtained from effecting step a) at least once and ii) said differentiating characteristic or at least one further differentiating characteristic;

wherein said measurement data provided by said detection hardware include quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto;

wherein said method further comprises the steps of:

c) providing data tuples (($N_i$, $m/z_i$, $I_i$); ($t_i$, $m/z_i$, $I_i$)) on the basis of the measurement data provided by the detection hardware by associating to each other at least one respective first characterizing measurement value ($N_i$; $t_i$) representing said characterization or at least one characterization in terms of said at least one first (SCAN NUMBER; DETECTION TIME) of said characterizing measurement quantities, at least one respective further characterizing measurement value ($m/z_i$) representing said characterization or at least one characterization in terms of said at least one further (MASS-TO-CHARGE RATIO) of said characterizing measurement quantities and at least one respective quantitative measurement value ($I_i$) representing said or at least one quantification (ION INTENSITY) in terms of said at least one quantitative measurement quantity (ION INTENSITY);

d) grouping said data tuples into characterizing measurement value intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of characterizing measurement values with respect to the characterizing measurement values for at least one of said characterizing measurement quantities, said intervals each being determined to potentially be associated to one particular of said constituents or products;

wherein said grouping is effected on the basis of at least one collective characteristic of a plurality of said quantitative measurement values ($I_i$) each belonging to a respective one of said data tuples;

wherein said method further comprises at least one of the steps of:

e) at least one of storing, displaying and printing of data or visualizations of data which reflect or include at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of said at least one of said characterizing measurement values obtained from said grouping;

f) further analysis of said at least one sample or of at least one of said constituents or products on the basis of at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of said at least one of said characterizing measurement values obtained from said grouping or on the basis of data or visualizations stored, displayed or printed according to step e).

The second aspect, proposes to group said measurement data on the basis of at least one collective characteristic for a plurality of said quantitative measurement values, each of said quantitative measurement values of said plurality belonging to a respective one of said data tuples. On the basis of this approach very effective grouping can be achieved. Referring to the example LC-MS analysis this approach can be adopted with advantage to determine relevant intervals for the time or scan number data parts, i.e. to find relevant intervals along a time or scan number axis of a corresponding coordinate system which may be defined with respect to the measurement data.

It should be pointed out that step a) may be effected several times simultaneously or sequentially. Step b) may include a separation similar to the separation according to step a), or may at least be adapted to effect such a separation. An example is mass spectroscopy which is adapted to effect a separation. If, however, the different substances are already separated then effecting mass spectroscopy with respect to said substances does not necessarily give rise to an additional separation but instead serves perhaps only to map the substances on the m/z axis for a certain detection time or scan number reflecting the separation effected in step a), possibly by using at least one chromatographic column or the like.

Also step b) could be effected several times simultaneously or sequentially. Further, depending on the measurement situation and the techniques used it may be possible to effect step b) simultaneously or overlapping with step a). An example is electrophoresis, in particular capillary electrophoresis (CE), which uses online detection of the electrophoretic bands by means of induced fluorescence. In such a measurement situation the electrophoresis separates substances. On the basis of this separation measurement data representing said separation may be obtained in accordance with step b).

Another possibility is that also step a) includes the use of detection hardware to provide measurement data. Again, it may be referred to the example of electrophoresis with online detection of the electrophoretic bands which may be detected by appropriate means. On the basis of the obtained separation an additional characterization, beside the characterizations obtained from detecting the fluorescent bands, may be obtained in accordance with step b).

With respect to step c) it should be noted, that there are many possibilities to organize the data. There are no limitations with respect to the data structures used. It is sufficient that the characterizing measurement values of a respective data tuple can be identified with respect to their association to each other and to the respective characterizing measurement quantity, so that these characterizing measurement values may be accessed for the grouping. Accordingly, the term "data tuple" and the association of the characterizing measurement values to each other has to be understood functionally and shall comprise any possible data organization which implements or reflects or allows such associations and possibilities of access.

Also, steps c) and d) may be effected simultaneously, possibly interleaved. The same applies to steps d) and e). Further, step d) or/and step e) on the one hand and step f) on the other hand may be effected simultaneously, possibly interleaved.

It should be noted, that generally said intervals are determined to be indeed associated to one particular of said constituents or products. The working hypothesis of the grouping is that the grouping is effective to determine intervals which each are associated to one particular of said constituents or products. However, not always it is possible to rule out wrong determinations if there are artifacts or if not the optimum analytical and detection techniques are used. If the possibility of errors is taken into account, then the grouping according to the invention in any case determines intervals which are potentially associated to one particular of said constituents or products. Whether these intervals are indeed associated to one particular of said constituents or products may be determined in an additional verification step, possibly taking into account present knowledge about the sample or group of samples to be analyzed and reference data included in a reference database.

With respect to step e) should be added, that preferably only data or visualizations of data which reflect or include groups of data tuples obtained from said grouping or/and intervals of respective characterizing measurement values obtained from said grouping are stored or/and displayed or/and printed, and that other data not falling in the groups or intervals are discarded. This leads to a major data reduction. Additional reduction of data in the sense of some sort of data compression may be obtained if not the data tuple of a respective group or falling in a respective interval are stored but instead data describing the group or the interval, in the case of LC-MS data, e.g. an average m/z value, an average t value or N value and possibly a summarizing intensity value (e.g. the sum of all individual intensities, integral over the area under a curve defined by the data tuples, average intensity value, and the like). Additionally or alternatively to the average m/z value and t value or N value the m/z interval and t interval or N interval may be stored, possibly by storing the boundaries of the respective interval or by storing a central value and the width of the respective interval. However, it should be emphasized that such a data reduction and even data compression is not always necessary, in particular if large data storage space is available and if fast processors are available. Under such circumstances a grouping of the data as such may be of high value for facilitating the analysis of the data. E.g. data tuples belonging to the same group may be identified in a visualization of the data by attributing different colors to different groups, such as known from false color or phantom color representations, so that a qualitative analysis of the respective sample or samples is facilitated for the scientist or operator viewing the visualization on a display or on a printout.

At least said grouping according to step d) and generally also the storing, displaying and printing and the further analysis of step e) and generally also the provision of data tuples according to step c) will generally be effected automatically or automatized by a suitable data processing arrangement, e.g. data processing unit or data processing system, possibly by a general purpose computer or by the control unit of a measurement and analyzing system. Although it might be possible, that a scientist or operator inputs certain data which trigger certain actions or which are taken as basis for certain processing steps, the grouping as such will generally be effected without human interaction on the basis of measurement raw data obtained from effecting said techniques, possibly under the control of a program instructions embodying the invention.

To advantage, said grouping may be effected on the basis of at least one collective characteristic comprising an overall quantitative measure value determined from said plurality of said quantitative measurement values (proposal 21). As overall quantitative measure value may serve for example an average quantitative measurement value for said plurality of quantitative measurement values or a sum or product of said quantitative measurement values of said plurality or the like. The sub-term "measure" in the term "overall quantitative measure value" means, that the overall quantitative measure value can serve as a measure which indicates an overall characteristic of said quantitative measurement values considered in combination. Accordingly, it is not ruled out that the overall quantitative measurement value decreases, if said quantitative measurement values or the average of some of said quantitative measurement values increases and vice versa. E.g., there might be a reciprocal relation between the overall quantitative measure value on one hand and the quantitative measurement values on the other hand.

Alternatively or additionally, said grouping may be effected to advantage on the basis of at least one collective characteristic comprising a shape of at least one curve or histogram which is directly or indirectly defined by those data tuples which each include at least one respective of said plurality of said quantitative measurement values (proposal 22).

Said shape of said at least one curve or histogram may be defined by value sub tuples, possibly value pairs, of those data tuples, wherein said value sub tuples, possibly value pairs, each include at least said at least one respective of said plurality of said quantitative measurement values and at least one respective of said characterizing measurement values, said at least one respective characterizing measurement value representing at least one of said characterizations in terms of said at least one characterizing measurement quantity which is associated to said or at least one respective quantitative measurement quantity (proposal 23).

Referring to step c), it is suggested that said data tuples are generated in step c) to include said at least one respective first characterizing measurement value (Ni; ti) mapped on at least one first dimension of said data tuples, to include said at least one respective further characterizing measurement value (m/$z_i$) mapped on at least one further dimension of said data tuples and to include said at least one respective quantitative measurement value (Ii) mapped on at least one other dimension of said data tuples (proposal 24).

Referring to step d) it is suggested, that in step d) the data tuples are grouped in characterizing measurement value intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) with respect to the characterizing measurement values for at least two different characterizing measurement quantities, wherein said grouping is effected such that interval sets ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) including one characterizing measurement value interval for each of said at least two different characterizing measurement quantities are determined to be potentially associated to one particular of said constituents or products, wherein said grouping is effected on the basis of said collective characteristics of said plurality of said quantitative measurement values ($I_i$) with respect to characterizing measurement value intervals ([$N_{ION}$−Δ$N_{dev}$, $N_{ION}$+Δ$N_{dev}$]; [$t_{ION}$−Δ$t_{dev}$, $t_{ION}$+Δ$t_{dev}$]) of characterizing measurement values for at least one of said characterizing measurement quantities (proposal 25). With reference to proposal 24, said characterizing measurement values associated to at least two different characterizing measurement quantities will be mapped on different dimensions of said data tuples.

Preferably, said grouping is effected on the basis of said collective characteristics of said plurality of said quantitative measurement values ($I_i$) with respect to characterizing measurement value intervals ([$N_{ION}$−Δ$N_{dev}$, $N_{ION}$+Δ$N_{dev}$]; [$t_{ION}$−Δ$t_{dev}$, $t_{ION}$+Δ$t_{dev}$]) of first characterizing measurement values for said first characterizing measurement quantity or at least one first characterizing measurement quantity, said characterizing measurement value intervals ([$N_{ION}$−Δ$N_{dev}$, $N_{ION}$+Δ$N_{dev}$]; [$t_{ION}$−Δ$t_{dev}$, $t_{ION}$+Δ$t_{dev}$]) of first characterizing measurement values herein also being denoted as first characterizing measurement value intervals (proposal 26).

Generally, said data stored, printed or displayed in step e), will include quantitative information representing said quantification or at least one quantification in terms of said quantitative measurement quantity or at least one quantitative measurement quantity (proposal 27).

Further, it is suggested that for each group of data obtained from said grouping at least one respective cumulative quantitative value is derived on the basis of the quantitative measurement values included in the data tuples of the respective group to represent said quantification or at least one quantification in terms of said quantitative measurement quantity or at least one quantitative measurement quantity (proposal 28). Preferably, in step e), the respective cumulative quantitative value is stored instead of the quantitative measurement values on which the cumulative quantitative value is based (proposal 29). A substantial data compression can be achieved. It is referred to the above remarks concerning step e) of proposal 20.

With reference to the first aspect of the invention it is further suggested, that in step d) said grouping is effected further on the basis of at least one statistical distribution of deviations (Δm/zi) of the respective characterizing measurement values (m/$z_i$) from a true or characteristic or mean characterizing measurement value (m/zION) associated to said particular of said constituents or products (proposal 30).

Said grouping, in step e) may to advantage be effected on the basis of at least one statistical distribution of measurement deviations indicating a statistical distribution of deviations (Δm/zi) of the respective characterizing measurement values from a true or characteristic or mean characterizing measurement value (m/zION) associated to said particular of said constituents or products (proposal 31).

Said intervals, to which said grouping refers, may correspond to intervals which according to said statistical distribution of deviations (Δm/zi) include a substantial amount of all respective characterizing measurement values which originate from said particular of said constituents or products (proposal 32).

A highly effective grouping may be achieved, if said intervals are prediction intervals predicted by said statistical distribution of deviations (Δm/zi) to include a substantial amount of all respective characterizing measurement values which originate from said particular of said constituents or products (proposal 33).

In particular, said intervals may be prediction intervals, possibly confidence intervals, predicted by said statistical distribution of deviations (Δm/zi) on the basis of initialization data and, in the course of the grouping according to step d), on the basis of data tuples already grouped to include a substantial amount of all respective characterizing measurement values which originate from said particular of said constituents or products and belong to data tuples not already grouped (proposal 34).

With reference to at least one of proposals 32 to 34 it is further suggested, that in step d) said data tuples are grouped in characterizing measurement value intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) with respect to the characterizing measurement values for at least two different characterizing measurement quantities, wherein said grouping is effected such that interval sets ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) including one characterizing measurement value interval for each of said at least two different characterizing measurement quantities are determined to potentially be associated to one particular of said constituents or products, wherein said grouping is effected on the basis of said at least one statistical distribution of deviations (Δm/zi) with respect to characterizing measurement value intervals ([m/zION−Δm/zdev, m/zION+Δm/zdev]) of characterizing measurement values for at least one of said characterizing measurement quantities (proposal 35). With reference to proposal 24, said characterizing measurement values associated to at least two different characterizing measurement quantities will be mapped on different dimensions of said data tuples.

Preferably, said grouping is effected on the basis of said at least one statistical distribution of deviations (Δm/zi) with respect to characterizing measurement value intervals ([m/zION−Δm/zdev, m/zION+Δm/zdev]) of further characterizing measurement values for said further characterizing measurement quantity or at least one further characterizing measurement quantity, said characterizing measurement value intervals ([m/zION−Δm/zdev, m/zION+Δm/zdev]) of further characterizing measurement values herein also being denoted as further characterizing measurement value intervals (proposal 36).

With reference to said proposals 1 to 19 according to said first aspect of the invention and to proposals 20 to 36 according to said second aspect of the invention, it should be noted, that preferably the approaches according to the first aspect and according to the second aspect are realized in combination, as explicitly suggested according to proposals 11 to 16 and proposals 30 to 36. However, also on the basis of only one of said approaches (approach according to the first aspect of the invention or approach according to the second aspect of the invention) major improvements compared to the prior art solutions may be achieved.

With reference to any one of said proposals it is proposed further, that said data tuples are accessed according to a predetermined access schedule in the course of said grouping (proposal 37). In particular, said data tuple or the data tuples of at least one subset of one data tuples may be accessed in a sequence governed by the characterizing measurement values for at least one of said characterizing measurement quantities, preferably by said first characterizing measurement quantities (proposal 38). To advantage, said data tuples or said data tuples of said at least one subset of said data tuples may be accessed in the order of increasing or decreasing characterizing measurement values (proposal 39).

With reference to the second aspect of the invention (compare proposals 11 and 20) and also with reference to additional proposals in this respect (compare proposals 12 to 16 and proposals 21 to 29) further proposals are mentioned in the following, which gear to further advantages.

With reference at least to proposal 14 or 23 it is further suggested, that said histogram or curve is directly or indirectly defined by said plurality of said quantitative measurement values and at least one respective characterizing measurement value associated to each quantitative measurement value of said plurality, the quantitative measurement values each being interpreted as an intensity value, yield value, amount value, count value, probability value or other quantitative value measured in terms of at least one quantitative measurement quantity such as intensity, yield, amount, count, probability or the like and measured with reference to the respective at least one characterizing measurement value (proposal 40). Additionally or alternatively, it is suggested that said curve or at least one curve, on which said grouping is based, is defined by those data tuples or by said value sub tuples, possibly value pairs, directly as a discrete curve which is discrete in terms of at least one of i) said at least one characterizing measurement quantity for which said characterizing measurement values are included in said data tuples or value sub tuples, possibly value pairs, and ii) said at least one quantitative measurement quantity for which said quantitative measurement values are included in said data tuples or value sub tuples, possibly value pairs (proposal 41). Further additionally or alternatively, it is suggested that said curve or at least one curve, on which said grouping is based, is defined by those data tuples or by said value sub tuples, possibly value pairs, directly or indirectly as a continuous curve which is continuous in terms of at least one of i) said at least one characterizing measurement quantity for which said characterizing measurement values are included in said data tuples or value sub tuples, possibly value pairs, and ii) said at least one quantitative measurement quantity for which said quantitative measurement values are included in said data tuples or value sub tuples, possibly value pairs (proposal 42).

A highly effective grouping on the basis of said at least one collective characteristics can be obtained, if said grouping involves to effect at least one peakedness check to determine whether at least one peakedness condition is fulfilled for those data tuples which each include at least one respective of said plurality of said quantitative measurement values or for said value sub tuples, possibly value pairs, or for said curve or histogram (proposal 43). Alternatively or additionally it is suggested, that said grouping involves to effect at least one unimodality check to determine whether at least one unimodality condition is fulfilled for those data tuples which each include at least one respective of said plurality of said quantitative measurement values or for said value sub tuples, possibly value pairs, or for said curve or histogram (proposal 44). A histogram or curve and correspondingly said data tuples having said plurality of quantitative measurement values are unimodal, if there is only one single maximum. Said check for unimodality is powerful to distinguish between peaks which indeed originate from one particular of said constituents or products and other peaks which are caused by artifacts of the applies techniques and the like.

In principle, there are different possibilities how this unimodality check could be implemented. According to a preferred embodiment said unimodality check involves a comparison of those data tuples or of said value sub tuples, possibly value pairs, or of said curve or histogram on the one hand with an reference function on the other hand, said reference function being determined on the basis of those data tuples or of said value sub tuples, possibly value pairs, or said curve or histogram, wherein point-wise differences between those data tuples or said value sub tuples, possibly value pairs, or said curve or histogram on the one hand and said reference function on the other hand are calculated for certain or all of a plurality of characterizing measurement values associated to said plurality of said quantitative measurement values, wherein said reference function is determined such on the basis of those data tuples or of said value sub tuples, possibly value pairs, or of said curve or histogram, that a maximum point-wise difference of the calculated point-wise differences or a point-wise differences sum of the calculated point-wise differences is a measure for fulfillment or not-fulfillment of the unimodality condition (proposal 45). Said reference function may be calculated from those data tuples or from set values sub-tuples, possibly value pairs, or from said curve or histogram by integration or summing up to obtain a first intermediate function, by finding a second intermediate function which is the nearest unimodal function to the first intermediate function and by differentiating said second intermediate function or calculating differences from said second intermediate function to obtain the reference function (proposal 46).

With reference to proposal 45 or 46 it is further suggested, that in said grouping at least one deviation measure value reflecting a deviation of said quantitative measurement values of said plurality or corresponding values of said curve or histogram from corresponding values of said reference function is calculated (proposal 47).

Generally, one can implement said unimodality check such, that said unimodality condition is determined to be fulfilled, if said deviation measure value falls short of a threshold deviation measure value and is determined to be not fulfilled, if said overall deviation measure value exceeds said threshold deviation measure value, or such, that said unimodality condition is determined to be not fulfilled, if said overall deviation measure value falls short of a threshold deviation measure value and is determined to be fulfilled, if said overall deviation measure value exceeds said threshold deviation measure value (proposal 48). It should be added, that the subterm "measure" in the term "deviation measure value"

intends to express, that any value reflecting the deviation of said quantitative measurement values from said reference function may be used as deviation measure value, in principle. Accordingly, the deviation measure value may increase with an overall deviation (e.g. some of point-wise differences) or, if a reciprocal relation is taken, may decrease with increasing deviation. However, preferably, said maximum point-wise difference or said point-wise differences sum are calculated as said deviation measure value (proposal 49). Beside, preferably additionally to said peakedness check or/and unimodality check additional checks may be applied to avoid a wrong determination of data points or intervals to be associated to one particular of said constituents or products. For example, said grouping may involve to effect at least one central moment check to determine whether at least one central moment of r-th order condition is fulfilled for those data tuples which each include at least one respective of said plurality of said quantitative measurement values or for said value sub tuples, possibly value pairs, or for said curve or histogram (proposal 50). In particular, it is suggested that said grouping involves to effect at least one combinational central moment check to determine whether at least one condition based on a relation between a plurality of central moments of different order is fulfilled for those data tuples which each include at least one respective of said plurality of said quantitative measurement values or for said value sub tuples, possibly value pairs, or for said curve or histogram (proposal 51).

According to a preferred embodiment said grouping involves to effect at least one kurtosis check to determine whether at least one kurtosis condition is fulfilled for those data tuples which each include at least one respective of said plurality of said quantitative measurement values or for said value sub tuples, possibly value pairs, or for said curve or histogram (proposal 52). A grouping on the basis of the so-called kurtosis determined for the measurement values, is highly effective to distinguish between peaks in said data which indeed originate from one particular of said constituents or products and other peaks which may be caused by artifacts of the applied techniques.

The reference to kurtosis herein shall include such a characterization of the measurement value which reflects or corresponds to the definition of kurtosis in statistics, namely the fourth central moment of a distribution divided by the second central moment of the distribution squared.

However, there are in principle a number of ways how the kurtosis check could be implemented. In this respect it is preferred that said kurtosis condition is determined to be fulfilled, if a kurtosis measure value falls short of a threshold measure value and is determined to be not fulfilled, if said kurtosis measure value exceeds said threshold kurtosis measure value or alternatively that said kurtosis condition is determined to be not fulfilled, if a kurtosis measure value falls short of a threshold kurtosis measure value and is determined to be fulfilled, if said kurtosis measure value exceeds said kurtosis measure value (proposal 53).

Generally, said grouping on the basis of said at least one collective characteristic may involve to calculate at least one of a central moment of second order and a central moment of fourth order on the basis of those data tuples or on the basis of said value sub tuples, possibly value pairs, or on the basis of said curve or histogram (proposal 54). Preferably, said grouping involves to calculate the central moment of second order and the central moment of fourth order on the basis of those data tuples or on the basis or said value sub tuples, possibly value pairs, or on the basis of said curve or histogram, and to determine a ratio between the central moment of fourth order and the central moment of second order squared (proposal 55). With reference to the kurtosis check and the kurtosis condition it is suggested, that said ratio between the central moment of fourth order and the central moment of second order squared is used as said kurtosis measure value (proposal 56).

Generally, said grouping, in particular also said grouping according to the second aspect of the invention, may involve a direct or indirect comparison of said quantitative measurement values of said plurality and associated characterizing measurement values or of those data tuples which each include at least one respective of said plurality of said quantitative measurement values or of said value sub tuples, possibly value pairs, or of said curve or histogram on the one hand with a statistical distribution of expected quantitative measurement values for characterizing measurement values around at least one true, characteristic or mean characterizing measurement value (NION; tION) on the other hand (proposal 57).

It may be appropriate, if said grouping involves to effect at least one central tendency check to determine whether at least one central tendency condition is fulfilled for those data tuples which each include at least one respective of said plurality of said quantitative measurement values or for said value sub tuples, possibly value pairs, or for said curve or histogram (proposal 58). The term "central tendency" refers to a so-called "location" of the distribution. A measure for said location may be for example some "mean value" (e.g. arithmetic mean, geometric mean, harmonic mean or generalized mean) or a simple sum of the respective measurement values.

According to a preferred embodiment, said grouping involves to effect at least one quantitative check, possibly intensity check, to determine whether at least one quantitative condition, possibly intensity condition, is fulfilled for those data tuples which each include at least one respective of said plurality of said quantitative measurement values or for said value sub tuples, possibly value pairs, or for said curve or histogram (proposal 59).

Referring to at least one of proposals 58 and 59, it is suggested, that in said grouping said quantitative measurement values of said plurality are combined to said or an overall quantitative measure value, possibly overall intensity measure value (proposal 60). To advantage, said combining of said quantitative measurement values to said overall quantitative measure value, possibly overall intensity measure value, may comprise to determine at least one background or baseline value, wherein said overall quantitative measure value corresponds to an combination of differences between said quantitative measurement values of said plurality and the background or baseline value or a respective background or baseline value (proposal 61). Preferably, said quantitative measurement values of said plurality or said differences are additively combined to said overall quantitative measure value, possibly overall intensity measure value (proposal 62).

There are in principle many possibilities, how said central tendency condition and said quantitative condition could be implemented. In this respect it is proposed that said central condition or said quantitative condition, possibly intensity condition, is determined to be fulfilled, if said overall quantitative measure value, possibly overall intensity measure value, exceeds a threshold quantitative measure value, possibly threshold intensity measure value, and is determined to be not fulfilled, if said overall quantitative measure value, possibly overall intensity measure value, falls short of said threshold quantitative measure value, possibly threshold intensity measure value, or alternatively that said central tendency condition or said quantitative condition, possibly said intensity condition, is determined to be not fulfilled, if said overall quantitative measure value, possibly overall intensity measure value, exceeds a threshold quantitative measure value, possibly threshold intensity measure value and is determined to be fulfilled, if said overall quantitative measure value, possibly overall intensity measure value falls short of said threshold quantitative measure value, possibly threshold intensity measure value (proposal 63). Again, the subterm "measure" is used to take account of the possibility, that there are no limitations, in principle, how the "measure value" is defined, so that either an increasing or a decreasing "measure value" indicates a better fulfillment of the respective condition.

Said grouping, according to the second aspect of the invention (compare proposal 11 and proposal 20) may to advantage involve the following steps (proposal 64):

d3) according to said or a predetermined access schedule accessing at least one data tuple of said data tuples or of said or a subset of said data tuples;

d5) identifying at least one accessed data tuple as first or further candidate member of a respective group of data tuples associated to one particular of said constituents or products, if desired said identification being dependent on the fulfillment of at least one identification condition;

d6) if an abort criterion or at least one of several abort criteria is fulfilled:
   i) aborting the grouping;
wherein steps d3) to d5) are repeated until step d6) is reached.

This grouping according to steps d3), d5) and d6) may involve also a grouping according to the first aspect of the invention.

One abort criterion may be based on the identification condition. E.g., according to one abort criterion, the grouping is aborted, if the accessed data tuple or a predetermined number of data tuples accessed successively or simultaneously does not fulfill the identification condition (proposal 64a). Further, depending on the organization of the measurement data, there might be an abort criterion which is based on the presence or non-presence of at least one respective data tuple to be accessed in access step d3). According to such an abort criterion the grouping is aborted, if in one access step d3) or in a predetermined number of access steps d3) no data tuple including relevant measurement data representing a detection by the detection hardware can be found (proposal 64b).

It should be added, that a plurality of groups or data tuples associated (or potentially associated) to one respective particular of said constituents or products may be considered simultaneously. The access according to step d3) may have the result that a respective accessed data tuple is added to the group of data tuples already established or to one of the groups of data tuples already established or that the first or one additional group of data tuples is established on the basis of this data tuple.

Preferably (proposal 65), step d5) further includes the substep of iii) applying at least one confirmation condition to a plurality of candidate members of said respective group of data tuples associated to one particular of said constituents or products, said plurality of candidate members being confirmed members of said group if said at least one confirmation condition is collectively fulfilled for said candidate members;

or the substep of iii') applying at least one confirmation condition to a plurality of candidate and confirmed members of said respective group of data tuples associated to one particular of said constituents or products, a respective candidate members being a confirmed member of said group if said at least one confirmation condition is collectively fulfilled for said candidate and confirmed members.

Further, it is suggested, that at least the first candidate member which was added to said group is deleted from said group or wherein said group is deleted if said at least one confirmation condition is not collectively fulfilled for said plurality of candidate members (proposal 66). Said at least one candidate member preferably is deleted from said group if said confirmation condition is not collectively fulfilled for said plurality of confirmed and candidate members (proposal 67).

With reference to step d6) it is suggested that one abort criterion comprises said at least one confirmation condition, said abort criterion being determined to be fulfilled if said confirmation condition is not collectively fulfilled for said plurality of candidate members or for a plurality of confirmed members together with at least one additional candidate member (proposal 68).

Said confirmation condition and accordingly the grouping may be based to advantage on at least one collective characteristic of a plurality of quantitative measurement values, each belonging to a respective one of said candidate or confirmed members (proposal 69). This proposal can be considered to be a special embodiment of the general approach according to proposal 11 and proposal 20 (compare step d)), i.e. of the solution according to the second aspect of the invention. In particular, said confirmation condition may be based on at least one collective characteristic comprising an overall quantitative measure value determined from said plurality of said quantitative measurement values belonging to said candidate or confirmed members (proposal 70; compare proposal 12 and proposal 21). Further, said confirmation condition may be based on at least one collective characteristic comprising a shape of at least one curve or histogram which is directly or indirectly defined by said candidate or confirmed members (proposal 71; compare proposal 13 and proposal 22). Also other proposals with respect to the approach according to the second aspect of the invention may be applied to said candidate or confirmed members or with respect to said confirmation condition. Accordingly, the determination whether said confirmation condition is fulfilled or not fulfilled may be effected in accordance with the features and method steps of at least one of proposals 12 to 16 or of at least one of proposals 21 to 26 or anyone of the other proposals, e.g. at least one of proposals 40 to 63 (proposal 72).

Further embodiments of the method may be advantageous. With respect to step d6) it is suggested (proposal 73) that this step further includes the substep of ii) if a group of candidate members or confirmed members or candidate and confirmed members was found then closing said group for further adding of candidate members.

According to a preferred embodiment the method steps d3) to d6) are repeated several times until all data tuples or all data tuples of said subset of data tuples have been accessed (proposal 74). Further, it is suggested, that several subsets are provided and that for each of said several subsets of said data tuples steps d3) to d6) are repeated at least once, generally several times until all data tuples of the respective subset of said data tuples have been accessed (proposal 75).

To advantage, said identification condition and accordingly said grouping may be based on at least one statistical distribution of deviations related to the respective characterizing measurement values (proposal 76). In particular, said identification condition may relate to the grouping according to the first aspect of the invention (compare proposal 1, step d) and proposal 30). In particular with reference to the first aspect of the invention, but also generally, said identification condition may be determined to be fulfilled, if at least one characterizing measurement value of the respective data tuple accessed falls into a predetermined characterizing measurement value interval or falls into a current characterizing measurement value interval obtained on the basis of said at least one statistical distribution of deviations (proposal 77). It should be added, that in this context predetermined characterizing measurement value intervals in the sense of conventional "hard binning" intervals may be used. However, preferably, intervals determined in course of the grouping with respect to their interval boundaries and their potential association to one particular of said constituents or products are used, which follow from the grouping according to the first aspect of the invention.

With reference to the first aspect of the invention (compare proposals 1 and 30) and also with reference to additional proposals in this respect (compare proposals 2 to 20 and 31 to 36) further proposals are mentioned in the following, which gear to further advantages.

Referring in particular to at least one of proposals 1 to 5 or 30 to 34 it is suggested, that said grouping on the basis of at least one statistical distribution of deviations ($\Delta m/zi$), in particular at least one statistical distribution of measurement deviations (compare proposals 2 and 31), involves a determination whether at least one characterizing measurement value ($\Delta m/zi$) of a respective data tuple falls or falls not into a current characterizing measurement value interval ($[m/z_{ION}-\Delta m/z_{dev}, m/z_{ION}+\Delta m/z_{dev}]$) obtained from said statistical distribution of deviations (proposal 78). Preferably, said statistical distribution of deviations ($\pm\Delta m/zi$) is updated on the basis of at least one of the determination that the respective at least one characterizing measurement value ($\Delta m/zi$) falls into the current characterizing measurement value interval ($[m/z_{ION}-\Delta m/z_{dev}, m/z_{ION}+\Delta m/z_{dev}]$) and the determination that the respective at least one characterizing measurement value falls not into the current characterizing measurement value interval, and wherein an updated characterizing measurement value interval ($[m/z_{ION}-\Delta m/z_{dev}, m/z_{ION}+\Delta m/z_{dev}]$) is obtained from the updated statistical distribution of deviations to be used as current characterizing measurement value interval in said grouping (proposal 79). Preferably, the Bayesian update or learning scheme is used in this context. With reference to the illustrative, non-limiting example LC-MS analysis, e.g. NC-ESI-MS analysis, this updating or learning can be effected to advantage with respect to determining relevant intervals along the mass-to-charge ratio axis.

With reference to proposal 5 or proposal 34 or anyone of the other proposals based on one of these proposals said grouping may (proposal 80) involve the following steps:

d1) assuming as current distribution of measurement deviations a prior distribution of measurement deviations on the basis of initialization data;
d2) obtaining (e.g. calculating or determining) at least one current prediction interval, possibly current confidence interval, on the basis of the current distribution of measurement deviations ($\Delta m/zi$);
d3) according to said or a predetermined access schedule accessing at least one data tuple, possibly the first or the next data tuple, of said data tuples or of said or a subset of said data tuples;
d4) determining whether at least one characterizing measurement value (m/zi) of said respective data tuple accessed falls or falls not into the current prediction interval;
d5) if the characterizing measurement value falls into the current prediction interval:
  i) identifying the data tuple which includes said characterizing measurement value as first or further candidate member of a respective group of data tuples associated to one particular of said constituents or products;
  ii) at least on the basis of said current distribution of measurement deviations, preferably also on the basis of the location of said characterizing measurement value within the current prediction interval, calculating as updated current distribution of measurement deviations a posterior distribution of measurement deviations which is a prior distribution of measurement deviations with respect to data tuples not already accessed;
d6) if an abort criterion or at least one of several abort criteria is fulfilled:
  i) aborting the grouping on the basis of the current distribution of measurement deviations;
wherein steps d2) to d5) are repeated until step d6) is reached.

This grouping according to steps d1) to d6) may also involve a grouping according to the second aspect of the invention.

With reference to step d6) it is suggested, that according to one abort criterion the grouping is aborted if the characterizing measurement value or a predetermined number of characterizing measurement values included in data tuples accessed successively or simultaneously falls not into the current prediction interval (proposal 81). Further, depending on the organization of the measurement data, there might be an abort criterion which is based on the presence or non-presence of at least one respective data tuple to be accessed in access step d3). According to such an abort criterion the grouping is aborted, if in one access step d3) or in a predetermined number of access steps d3) no data tuple including relevant measurement data representing a detection by the detection hardware can be found (proposal 81 a).

It should be added, that a plurality of groups or data tuples associated (or potentially associated) to one respective particular of said constituents or products may be considered simultaneously. The access according to step d3) may have the result that a respective accessed data tuple is added to the group of data tuples already established or to one of the groups of data tuples already established or that the first or one additional group of data tuples is established on the basis of this data tuple.

Step d5) may (proposal 82) to advantage further include the substeps of
  iii) applying at least one confirmation condition to a plurality of candidate members of said respective group of data tuples associated to one particular of said constituents or products, said plurality of candidate members being confirmed members of said group if said at least one confirmation condition is collectively fulfilled for said candidate members;
or the substep of
  iii') applying at least one confirmation condition to a plurality of candidate and confirmed members of said respective group of data tuples associated to one particular of said constituents or products, a respective candidate member being a confirmed member of said group if said at least one confirmation condition is collectively fulfilled for said candidate and confirmed members.

The confirmation condition may be based on collective characteristics of said candidate members or collective and candidate members.

The proposed differentiations between confirmed members and candidate members allow highly effective grouping since data points which have already been determined to be associated to a particular of said constituents or products according to certain tests conditions and accordingly identified as confirmed members can be maintained and additional data points can be tested together with the confirmed members against said conditions to determine, whether also these additional data points are associated to the same constituent or product.

With respect to the consequences which shall be drawn if said at least one confirmation condition or at least one of several confirmation conditions is not collectively fulfilled for said plurality of candidate members or said plurality of candidate and confirmed members different solutions are possible. According to one approach at least the first candidate member which was added to said group is deleted from said group or wherein said group is deleted if said at least one confirmation condition or if at least one particular confirmation condition of several confirmation conditions is not collectively fulfilled for said plurality of candidate members (proposal 83). Further, it is suggested, that at least one candidate member is deleted from said group if said at least one confirmation condition or if at least one particular confirmation condition of several confirmation conditions is not collectively fulfilled for said plurality of confirmed and candidate members (proposal 84).

According to a preferred embodiment one abort criterion comprises said at least one confirmation condition or at least one of several confirmation conditions, said abort criterion being determined to be fulfilled if said confirmation condition is not collectively fulfilled for said plurality of candidate members or for a plurality of confirmed members together with at least one additional candidate member (proposal 85).

A highly effective grouping can be obtained, if said confirmation condition and accordingly the grouping is based on at least one collective characteristic of a plurality of quantitative measurement values ($I_i$) each belonging to a respective one of said candidate or confirmed members (proposal 86). In particular, said confirmation condition may relate to the grouping according to the second aspect of the invention (compare proposal 11 and proposal 20, step d)). Relating said collective characteristic, on which said grouping is based, to the candidate members or said candidate and confirmed members is a preferred embodiment of said grouping according to the second aspect of the invention. Accordingly, said confirmation condition may be based on at least one collective characteristic comprising an overall quantitative measure value determined from said plurality of said quantitative measurement values belonging to said candidate or confirmed members (proposal 87). Further, said confirmation condition may be based on at least one collective characteristic comprising a shape of at least one curve or histogram which is directly or indirectly defined by said candidate or confirmed members (proposal 88). Also other proposals with respect to the second aspect of the invention may be applied in this context. Accordingly, the determination whether said confirmation condition is fulfilled or not fulfilled may be effected in accordance with the features and method steps of at least one of proposal 12 to 16 or at least one of proposals 21 to 26 or anyone of the other proposals, e.g. proposals 40 to 77 (proposal 89).

Referring again to the aborting of the grouping on the basis of the current distribution of measurement deviations it is further suggested (proposal 90), that step d6) further includes the substeps of ii) if a group of candidate members or confirmed members or candidate and confirmed members was found then closing said group for further adding of candidate members.

It is proposed that steps d1) to d6) are repeated several times until all data tuples or all data tuples of said subset of data tuples have been accessed (proposal 91). Further, it is suggested that for each of several subsets of said data tuples steps d1) to d6) are repeated at least once, generally several times until all data tuples of the respective subset of data tuples have been accessed (proposal 92).

It is proposed that for at least one reference subset of data tuples the prior distribution of measurement deviations is initialized in step d1) on the basis predetermined or assumed initialization data, said initialization data preferably including at least one of theoretical initialization data and initialization data obtained or provided on the basis of measurements using at least one external standard and initialization data assumed on the basis of practical experience of the past, wherein said reference subset of data tuples includes data tuples which are determined to potentially be caused by a reference constituent added to the sample for reference purposes or as internal standard or to potentially be caused by a product related to such a reference constituent (proposal 93). Further, it is suggested that for at least one characterizing subset of data tuples the prior distribution of measurement deviations is initialized in step d1) on the basis predetermined or assumed initialization data, said initialization data preferably including at least one of theoretical initialization data and initialization data obtained or provided on the basis of measurements using at least one external standard and initialization data assumed on the basis of practical experience of the past and initialization data obtained from the grouping effected with respect to the data tuples of said reference subset, wherein said characterizing subset of data tuples includes data tuples which are determined to potentially be caused by constituents of interest or unknown constituents included in the sample or to potentially be caused by products related to such a constituent (proposal 94).

Proposals 93 and 94 allow, that in a update or learning scheme, e.g. Bayesian update learning scheme, included in said grouping the updating or learning starts from appropriate start values.

Many of the above proposals relate directly or indirectly to one particular or both aspects of the invention, i.e. relate directly or indirectly to the invention according to the first aspect or/and to the invention according to the second aspect. Many additional advantages can be obtained also from features and method steps which are not related to implementations of these approaches of the invention or which are less directly directed to the implementation of these approaches. E.g., method steps effecting a denoising of the measurement data may be implemented. In particular, it is suggested that the method comprises the step of denoising said measurement data or said data tuples by eliminating data points or data tuples determined to potentially by caused by at least one kind of noise, such as electronic noise or chemical noise, associated to or caused by at least one of said techniques or said detection hardware (proposal 95). Preferably, said denoising is effected before effecting said grouping (proposal 96), so that the noise has no detrimental effect on the grouping.

With reference to proposal 9 or proposal 20 said denoising may comprise to determine a distribution of measured quantitative measurement values (Ii) and to eliminate those data points or data tuples whose respective at least one quantitative measurement value falls short of a quantitative value threshold, possibly intensity threshold, derived from said distribution of measured quantitative measurement values (proposal 97). A highly effective noise filtering at least for certain measurement situations may be obtained, if said quantitative values threshold, possibly intensity threshold, corresponds to a minimum in a histogram of quantitative measurement values or logarithms of quantitative measurement values representing said distribution, wherein said minimum is a minimum between at least one histogram peak attributed to real signals on the one side and at least one histogram peak attributed to noise on the other side (proposal 98).

The method according to a first or/and second aspect of the invention may additionally comprise the step of characterizing measurement value dependent filtering of said measurement data or said data tuples by eliminating data points or data tuples determined to potentially be caused by a reference constituent added to the sample for reference purposes or as internal standard or to potentially be caused by a product related to such a reference constituent or determined to correspond to systematic artifacts of at least one of said techniques or said detection hardware (proposal 99). As appropriate, said characterizing measurement value depending filtering may be effected before or after or during said grouping. In case of filtering with respect to data points relating to a reference constituent which are used for the initialization of a update or learning scheme within said grouping, these data points or data tuples have of course to be maintained until the initialization has been effected. Often it will be appropriate to maintain such data points or data tuples as reference data along the other data to be stored or displayed or printed and possibly used for further analysis according to steps e) and f).

The method according to the first or second or both aspects of the invention may further comprise the step of characterizing measurement value independent filtering of said measurement data or said data tuples by eliminating data points or data tuples determined to correspond to unsystematic artifacts of at least one of said techniques or said detection hardware (proposal 100). E.g., artifacts such as spikes may be removed. This filtering may be effected in course of the grouping. Preferably, said measurement data or said data tuples are eliminated on the basis of at least one distributional criterion applied to said data points or data tuples (proposal 101).

Generally, said grouping according to the first aspect or according to the second aspect or according to both aspects of the invention may involve to effect a respective grouping with respect to a plurality of ensembles of data tuples, said ensembles being obtained on the basis of different samples or by effecting said two or more techniques repeatedly with respect to the same sample (proposal 102). In this case, the grouping results achieved for each ensemble may be of interest or, alternatively, secondary grouping results achieved from combining the grouping results achieved with respect to each ensemble. With respect to the second possibility it is proposed, that said grouping involves to combine at least one respective group of data tuples obtained from the grouping effected with respect to one of said ensembles with at least one respective group of data tuples obtained from the grouping effected with respect to at least one other of said ensembles to obtain a combined group of data tuples or combined groups of data tuples as result of said grouping (proposal 103). Alternatively or additionally said grouping may involve to combine at least one respective characterizing measurement value interval obtained from the grouping effected with respect to one of said ensembles with at least one respective characterizing measurement value interval obtained from the grouping effected with respect to at least one other of said ensembles to obtain a combined characterizing measurement value interval or combined characterizing measurement value intervals as result of said grouping (proposal 104).

In the foregoing it was often referred to the measurement situation of LC-MS spectroscopy, e.g. LC-ESI-MS spectroscopy as only a non-limiting illustrative example. In principle, there are no limitations with respect to the techniques, (at least one first analytical technique, e.g. first analytical and detection techniques and at least one further technique, e.g. further analytical technique or further detection technique or further analytical and detection technique) used.

With respect to a first technique it is believed that any technique which is adapted to effect a separation of at least one of said constituents and products can be used. Somewhat more generalized it is suggested that said first technique or at least one first technique is adapted to effect a separation of at least one of said constituents and products, preferably on the basis of at least one of chemical effects, physical effects, kinetic properties and equilibrium properties (proposal 105). According to a preferred embodiment said first analytical technique or at least one first analytical technique comprises at least one of a chromatographic technique and an electrophoretic technique (proposal 106).

It should be noted that also said first analytical technique or at least one first analytical technique may comprise a mass spectrometric technique, possibly including an ionization technique, preferably electrospray ionization technique or/and MALDI technique (proposal 107).

With respect to said further technique it is proposed, that said further technique or at least one further technique comprises a spectrometric technique (proposal 108). E.g., said further technique or at least one further technique may comprise a photospectrometric technique (proposal 109). Another possibility is, that said further technique or at least one further technique comprises at least one of an electrochemical and coulometric technique (proposal 110).

Also said further technique or at least one further technique may be adapted to effect a separation of at least one of said constituents and products, preferably on the basis of at least one of chemical effects, physical effects, kinetic properties and equilibrium properties (proposal 111).

Preferably, said further technique or at least one further technique comprises a mass spectrometric technique, possibly including an ionization technique, preferably electrospray ionization technique or/and MALDI technique (proposal 112). Other techniques may be used alternatively or additionally.

Said further technique or at least one further technique may comprise a particle detection technique, possibly ion detection technique (proposal 113). Further, said further technique or at least one further technique may comprise at least one of a photon detection technique, radiation detection technique and electron detection technique (proposal 114).

The invention, according to the first aspect, further provides (proposal 115) a system for analyzing of at least one sample by effecting two or more techniques to provide characterization data which characterize said sample with respect to at least one of constituents, in particular chemical, biological or biochemical constituents contained therein and products resulting from effecting at least one of said techniques in accordance with the method of the invention, comprising:

a) at least one first analyzing section or unit adapted to effect at least one first analytical technique i) to separate constituents or
ii) to separate products resulting from effecting said first analytical technique or at least one first analytical technique or
iii) to separate constituents and products resulting from effecting said first analytical technique or at least one first analytical technique,
said first analyzing section or unit being adapted to effect said first analytical technique with respect to a sample or with respect to constituents or products already separated, said first analyzing section or unit being adapted to effect said separation on the basis of at least one first differentiating characteristic of said constituents or products;
b) at least one further section or unit adapted to effect at least one further technique to characterize separated constituents or products on the basis of at least one of i) at least one separation achieved by said or one first analyzing section or unit and ii) at least one further differentiating characteristic, said further technique being at least one of an analytical and detection technique, said further section or unit being at least one of an analytical and detection section or unit;
wherein at least said further section or unit includes or has associated detection hardware which is adapted to provide measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIME) of said characterizing measurement quantities reflecting said or at least one separation achieved by said or one first analyzing section or unit and at least one further (MASS-TO-CHARGE RATIO) of said characterizing measurement quantities reflecting at least one of i) at least one other separation achieved by said or one first analyzing section or unit and ii) said further differentiating characteristic or at least one further differentiating characteristic;
wherein said detection hardware may or may not be adapted to provide said measurement data including quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto;
wherein said system further comprises at least one control unit having at least one processor, said control unit including or having associated at least one data storage unit, said control unit further preferably having associated at least one of a display unit and a printing unit and preferably being arranged or programmed to control said at least one first analyzing section or unit and said at least one further section or unit;
wherein said control unit is arranged or programmed to
c) provide data tuples on the basis of the measurement data provided by the detection hardware by associating to each other at least one respective first characterizing measurement value ($N_i$; $t_i$) representing said characterization or at least one characterization in terms of said at least one first (SCAN NUMBER; DETECTION TIME) of said characterizing measurement quantities and at least one respective further characterizing measurement value ($m/z_i$) representing said characterization or at least one characterization in terms of said at least one further (MASS-TO-CHARGE RATIO) of said characterizing measurement quantities;
d) group said data tuples into characterizing measurement value intervals ([m/zION$-\Delta$m/zdev, m/zION+$\Delta$m/zdev], [$N_{ION}-\Delta N_{dev}$, $N_{ION}+\Delta N_{dev}$]; [m/zION$-\Delta$m/zdev, m/zION+$\Delta$m/zdev], [$t_{ION}-\Delta t_{dev}$, $t_{ION}+\Delta t_{dev}$]) of characterizing measurement values with respect to the characterizing measurement values for at least one of said characterizing measurement quantities, said intervals each being determined to potentially be associated to one particular of said constituents or products;
wherein said control unit is arranged or programmed to effect said grouping on the basis of at least one statistical distribution of deviations ($\Delta m/zi$) of the respective characterizing measurement values ($m/z_i$) from a true or characteristic or mean characterizing measurement value (m/zION) associated to said particular of said constituents or products;
wherein said control unit further is arranged or programmed to provide at least one of the following:
e) at least one of storing, displaying and printing of data or visualizations of data which reflect or include at least one of i) groups of data tuples obtained from said grouping and ii) intervals ([m/zION$-\Delta$m/zdev, m/zION+$\Delta$m/zdev], [$N_{ION}-\Delta N_{dev}$, $N_{ION}+\Delta N_{dev}$]; [m/zION$-\Delta$m/zdev, m/zION+$\Delta$m/zdev], [$t_{ION}-\Delta t_{dev}$, $t_{ION}+\Delta t_{dev}$]) of said at least one of said characterizing measurement values obtained from said grouping;
f) further analysis of said at least one sample or of at least one of said constituents or products on the basis of at least one of i) groups of data tuples obtained from said grouping and ii) intervals ([m/zION$-\Delta$m/zdev, m/zION+$\Delta$m/zdev], [$N_{ION}-\Delta N_{dev}$, $N_{ION}+\Delta N_{dev}$]; [m/zION$-\Delta$m/zdev, m/zION+$\Delta$m/zdev], [$t_{ION}-\Delta t_{dev}$, $t_{ION}+\Delta t_{dev}$]) of said at least one of said characterizing measurement values obtained from said grouping or on the basis of data or visualizations stored, displayed or printed according to measure e).

The invention, according to the second aspect, further provides (proposal 116) a system for analyzing at least one sample by effecting two or more techniques to provide characterization data which characterize said sample with respect to at least one of constituents, in particular chemical, biological or biochemical constituents contained therein and products resulting from effecting at least one of said techniques in accordance with the method of the invention, comprising:
a) at least one first analyzing section or unit adapted to effect at least one first analytical technique
i) to separate constituents or
ii) to separate products resulting from effecting said first analytical technique or at least one first analytical technique or
iii) to separate constituents and products resulting from effecting said first analytical technique or at least one first analytical technique,
said first analyzing section or unit being adapted to effect said first analytical technique with respect to a sample or with respect to constituents or products already separated, said first analyzing section or unit being adapted to effect said separation on the basis of at least one first differentiating characteristic of said constituents or products;
b) at least one further section or unit adapted to effect at least one further technique to characterize separated constituents or products on the basis of at least one of i) at least one separation achieved by said or one first analyzing section or unit and ii) at least one further differentiating characteristic, said further technique being at least one of an analytical and detection technique, said further section or unit being at least one of an analytical and detection section or unit;

wherein at least said further section or unit includes or has associated detection hardware which is adapted to provide measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIME) of said characterizing measurement quantities reflecting said or at least one separation achieved by said or one first analyzing section or unit and at least one further (MASS-TO-CHARGE RATIO) of said characterizing measurement quantities reflecting at least one of i) at least one other separation achieved by said or one first analyzing section or unit and ii) said further differentiating characteristic or at least one further differentiating characteristic;

wherein said detection hardware is adapted to provide said measurement data including quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto;

wherein said system further comprises at least one control unit having at least one processor, said control unit including or having associated at least one data storage unit, said control unit further preferably having associated at least one of a display unit and a printing unit and preferably being arranged or programmed to control said at least one first analyzing section or unit and said at least one further section or unit;

wherein said control unit is arranged or programmed to c) provide data tuples (($N_i$, $m/z_i$, $I_i$); ($t_i$, $m/z_i$, $I_i$)) on the basis of the measurement data provided by the detection hardware by associating to each other at least one respective first characterizing measurement value (Ni; ti) representing said characterization or at least one characterization in terms of said at least one first (SCAN NUMBER; DETECTION TIME) of said characterizing measurement quantities, at least one respective further characterizing measurement value ($m/z_i$) representing said characterization or at least one characterization in terms of said at least one further (MASS-TO-CHARGE RATIO) of said characterizing measurement quantities and at least one respective quantitative measurement value (Ii) representing said or at least one quantification (ION INTENSITY) in terms of said at least one quantitative measurement quantity (ION INTENSITY);

d) group said data tuples into characterizing measurement value intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of characterizing measurement values with respect to the characterizing measurement values for at least one of said characterizing measurement quantities, said intervals each being determined to potentially be associated to one particular of said constituents or products;

wherein said control unit is arranged or programmed to effect said grouping on the basis of at least one collective characteristic of a plurality of said quantitative measurement values (Ii) each belonging to a respective one of said data tuples;

wherein said control unit further is arranged or programmed to provide at least one of the following:

e) at least one of storing, displaying and printing of data or visualizations of data which reflect or include at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−$t_{dev}$, $t_{ION}$+Δ$t_{dev}$]) of said at least one of said characterizing measurement values obtained from said grouping;

f) further analysis of said at least one sample or of at least one of said constituents or products on the basis of at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of said at least one of said characterizing measurement values obtained from said grouping or on the basis of data or visualizations stored, displayed or printed according to measure e).

For the system according to the first or second or both aspects of the invention it is further proposed, that said first analyzing section or unit, said detection hardware, possibly respective other components of the system and said control unit are adapted, arranged or programmed to effect said techniques, to provide said data tuples, to effect said grouping and to provide at least one of said measures e) and f) in accordance with the method according to one or several of proposals 1 to 114 (proposal 117).

It should be noted, that the system according to the invention may be in the form of a plurality of structurally independent sub-systems, possibly located at different locations. One sub-system, a measurement sub-system, may be provided for effecting the measurements only and another sub-system, a grouping sub-system, may be provided to effect the data grouping only on the basis of measurement data provided by the measurement sub-system and transferred to the grouping sub-system. This transfer of data may be done via a communication link or via data carriers.

The invention, according to the first aspect, further provides (proposal 118) a program of instructions executable by a system for analyzing at least one sample by effecting two or more techniques to provide characterization data which characterize said sample with respect to at least one of constituents, in particular chemical, biological or biochemical constituents contained therein and products resulting from effecting at least one of said techniques in accordance with the method of the invention, the system comprising:

a) at least one first analyzing section or unit adapted to effect at least one first analytical technique
  i) to separate constituents or
  ii) to separate products resulting from effecting said first analytical technique or at least one first analytical technique or
  iii) to separate constituents and products resulting from effecting said first analytical technique or at least one first analytical technique,
  said first analyzing section or unit being adapted to effect said first analytical technique with respect to a sample or with respect to constituents or products already separated, said first analyzing section or unit being adapted to effect said separation on the basis of at least one first differentiating characteristic of said constituents or products;

b) at least one further section or unit adapted to effect at least one further technique to characterize separated constituents or products on the basis of at least one of i) at least one separation achieved by said or one first analyzing section or unit and ii) at least one further differentiating characteristic, said further technique being at least one of an analytical and detection technique, said further section or unit being at least one of an analytical and detection section or unit;

wherein at least said further section or unit includes or has associated detection hardware which is adapted to provide measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIME) of said characterizing measurement quantities reflecting said or at least one separation achieved by said or one first analyzing section or unit and at least one further (MASS-TO-CHARGE RATIO) of said characterizing measurement quantities reflecting at least one of i) at least one other separation achieved by said or one first analyzing section or unit and ii) said further differentiating characteristic or at least one further differentiating characteristic;

wherein said detection hardware may or may not be adapted to provide said measurement data including quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto;

wherein said system further comprises at least one control unit having at least one processor, said control unit including or having associated at least one data storage unit, said control unit further preferably having associated at least one of a display unit and a printing unit and preferably being arranged or programmed to control said at least one first analyzing section or unit and said at least one further section or unit;

wherein said control unit in response to said instructions performs the steps of:

c) providing data tuples on the basis of the measurement data provided by the detection hardware by associating to each other at least one respective first characterizing measurement value ($N_i$; $t_i$) representing said characterization or at least one characterization in terms of said at least one first (SCAN NUMBER; DETECTION TIME) of said characterizing measurement quantities and at least one respective further characterizing measurement value (m/$z_i$) representing said characterization or at least one characterization in terms of said at least one further (MASS-TO-CHARGE RATIO) of said characterizing measurement quantities;

d) grouping said data tuples into characterizing measurement value intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of characterizing measurement values with respect to the characterizing measurement values for at least one of said characterizing measurement quantities, said intervals each being determined to potentially be associated to one particular of said constituents or products;

wherein said control unit in response to said instructions effects said grouping on the basis of at least one statistical distribution of deviations (Δm/zi) of the respective characterizing measurement values (m/$z_i$) from a true or characteristic or mean characterizing measurement value (m/zION) associated to said particular of said constituents or products;

wherein said control unit in response to said instructions further performs at least one of the following steps:

e) at least one of storing, displaying and printing of data or visualizations of data which reflect or include at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of said at least one of said characterizing measurement values obtained from said grouping;

f) further analysis of said at least one sample or of at least one of said constituents or products on the basis of at least one of i) groups of data tuples obtained from said grouping and ii) intervals ([m/zION−Δm/zdev, m/zION+Δm/zdev], [$N_{ION}$−Δ$N_{dev}$, $N_{ION}$+Δ$N_{dev}$]; [m/zION−Δm/zdev, m/zION+Δm/zdev], [$t_{ION}$−Δ$t_{dev}$, $t_{ION}$+Δ$t_{dev}$]) of said at least one of said characterizing measurement values obtained from said grouping or on the basis of data or visualizations stored, displayed or printed according to step e).

A second aspect further provides (proposal 119) a program of instructions executable by a system for analyzing at least one sample by effecting two or more techniques to provide characterization data which characterize said sample with respect to at least one of constituents, in particular chemical, biological or biochemical constituents contained therein and products resulting from effecting at least one of said techniques, the system comprising:

a) at least one first analyzing section or unit adapted to effect at least one first analytical technique
   i) to separate constituents or
   ii) to separate products resulting from effecting said first analytical technique or at least one first analytical technique or
   iii) to separate constituents and products resulting from effecting said first analytical technique or at least one first analytical technique,
   said first analyzing section or unit being adapted to effect said first analytical technique with respect to a sample or with respect to constituents or products already separated, said first analyzing section or unit being adapted to effect said separation on the basis of at least one first differentiating characteristic of said constituents or products;

b) at least one further section or unit adapted to effect at least one further technique to characterize separated constituents or products on the basis of at least one of i) at least one separation achieved by said or one first analyzing section or unit and ii) at least one further differentiating characteristic, said further technique being at least one of an analytical and detection technique, said further section or unit being at least one of an analytical and detection section or unit;

wherein at least said further section or unit includes or has associated detection hardware which is adapted to provide measurement data representing at least one characterization of said constituents or products in terms of at least two characterizing measurement quantities (SCAN NUMBER, MASS-TO-CHARGE RATIO; DETECTION TIME, MASS-TO-CHARGE RATIO), at least one first (SCAN NUMBER; DETECTION TIMEt) of said characterizing measurement quantities reflecting said or at least one separation achieved by said or one first analyzing section or unit and at least one further (MASS-TO-CHARGE RATIO) of said characterizing measurement quantities reflecting at least one of i) at least one other separation achieved by said or one first analyzing section or unit and ii) said further differentiating characteristic or at least one further differentiating characteristic;

wherein said detection hardware is adapted to provide said measurement data including quantitative measurement data representing at least one quantification (ION INTENSITY) detected by said detection hardware and provided by the detection hardware in terms of at least one quantitative measurement quantity (ION INTENSITY) with reference to at least one characterizing measurement quantity associated thereto;

wherein said system further comprises at least one control unit having at least one processor, said control unit including or having associated at least one data storage unit, said control unit further preferably having associated at least one of a display unit and a printing unit and preferably being arranged or programmed to control said at least one first analyzing section or unit and said at least one further section or unit;

wherein said control unit in response to said instructions performs the steps of:

c) providing data tuples (($N_i$, $m/z_i$, $I_i$); ($t_i$, $m/z_i$, $I_i$)) on the basis of the measurement data provided by the detection hardware by associating to each other at least one respective first characterizing measurement value (Ni; ti) representing said characterization or at least one characterization in terms of said at least one first (SCAN NUMBER; DETECTION TIME) of said characterizing measurement quantities, at least one respective further characterizing measurement value ($m/z_i$) representing said characterization or at least one characterization in terms of said at least one further (MASS-TO-CHARGE RATIO) of said characterizing measurement quantities and at least one respective quantitative measurement value ($I_i$) representing said or at least one quantification (ION INTENSITY IION) in terms of said at least one quantitative measurement quantity (ION INTENSITY);

d) grouping said data tuples into characterizing measurement value intervals ([m/zION−$\Delta$m/zdev, m/zION+$\Delta$m/zdev], [$N_{ION}$−$\Delta N_{dev}$, $N_{ION}$+$\Delta N_{dev}$]; [m/zION−$\Delta$m/zdev, m/zION+$\Delta$m/zdev], [$t_{ION}$−$\Delta t_{dev}$, $t_{ION}$+$\Delta t_{dev}$]) of characterizing measurement values with respect to the characterizing measurement values for at least one of said characterizing measurement quantities, said intervals each being determined to potentially be associated to one particular of said constituents or products;

wherein said control unit in response to said instructions effects said grouping on the basis of at least one collective characteristic of a plurality of said quantitative measurement values ($I_i$) each belonging to a respective one of said data tuples;

wherein said control unit in response to said instructions further performs at least one of the following steps:

e) at least one of storing, displaying and printing of data or visualizations of data which reflect or include at least one of i) groups of data tuples obtained from said grouping and ii) intervals ([m/zION−$\Delta$m/zdev, m/zION+$\Delta$m/zdev], [$N_{ION}$−$\Delta N_{dev}$, $N_{ION}$+$\Delta N_{dev}$]; [m/zION−$\Delta$m/zdev, m/zION+$\Delta$m/zdev], [$t_{ION}$−$\Delta t_{dev}$, $t_{ION}$+$\Delta t_{dev}$]) of said at least one of said characterizing measurement values obtained from said grouping;

f) further analysis of said at least one sample or of at least one of said constituents or products on the basis of at least one of i) groups of data tuples obtained from said grouping and ii) intervals ([m/zION−$\Delta$m/zdev, m/zION+$\Delta$m/zdev], [$N_{ION}$−$\Delta N_{dev}$, $N_{ION}$+$\Delta N_{dev}$]; [m/zION−$\Delta$m/zdev, m/zION+$\Delta$m/zdev], [$t_{ION}$−$\Delta t_{dev}$, $t_{ION}$+$\Delta t_{dev}$]) of said at least one of said characterizing measurement values obtained from said grouping or on the basis of data or visualizations stored, displayed or printed according to step e).

For the program according to the first or the second or both aspects, it is further proposed, that said control unit, in response to said instructions provides said data tuples, effects said grouping and effects at least one of steps e) and f) in accordance with the method as defined by one or several of proposals 1 to 114 (proposal 120). Said program may be executable by the system according to one of proposals 115 to 117 to perform the method as defined by one or several of proposals 1 to 114 (proposal 121).

It should be noted, that the program of instructions may serve to control only a grouping sub-system of an overall system comprising at least one measurement sub-system and at least one grouping sub-system. In such a case the control unit of the grouping sub-system would work on data provided by the detection hardware of the measurement sub-system and transferred to the grouping sub-system, e.g. via a communication link or by means of data carriers. An additional program module might serve to control the measurement sub-system.

Embodiments may further relates to a computer program product embodying the program according to one of proposals 118 to 121 (proposal 122). The computer program products may be in the form of a computer readable medium carrying said program of instructions (proposal 123).

The invention further relates to a server computer system storing the program according to one of proposals 118 to 121 for downloading via a communication link, possibly via internet (proposal 124).

The present invention as defined by the independent claims and, concerning preferred embodiments and designs leading to further advantages, as defined by the dependent claims and the different proposals in the foregoing allows and explicitly provides to treat all singles or measurement values in all dimensions explicitly as variants, i.e. random or stochastic variables. This reflects applied measuring procedures generally more correctly than treating e.g. a respective quantitative measurement quantity (e.g. ion intensity) as variants on a preset grid (hard bins) of associated characterizing measurement values (e.g. mass-to-charge ratio and time or scan number values).

Further, different aspects and additional proposals allow obtainment, where appropriate, of information on the properties of the variants from all measurements of a measurement run including quality samples or reference samples, e.g. internal standard samples. Accordingly, more reliable information can be obtained.

In published methods concerning LC-MS spectrometry the data points are collected in bins of a preset grid on the mass axis and the time axis. Thus, signals of one substance may be located/detected in two different bins, due to the measurement inaccuracy of the mass axis, which leads to the following errors:

wrong allocation of the bins to peaks,
wrong total intensity values in peaks,
gaps occurring in the retention time axis may even lead to the right peak not being recognized as a peak at all.

Various aspects aim at leaving the scheme of the grid altogether and having the position and size of bins determined by signals or the measurement data as they are obtained from the respective sample. Thus, the non-detection of a peak is avoided and the measurement of a detected peak becomes more precise in all, possibly three or more dimensions.

On the basis of the knowledge about the applied techniques, e.g. about the chromatographic process and the mass spectrometric detection, many setting parameters of the data preprocessing and processing process may be automatically found, in particular for a statistical modeling on which the grouping is based. The estimate of the setting parameter can be done both sample specific for individual samples and globally for a number of samples, depending on what is representative according to the modeling applied. Thus, a manual setting of important parameters of the data preprocessing and processing can be avoided to a great extent or can at least be done appropriately and precise in view of the measurement situation and the sample or samples to be analyzed. This makes it easier to transmit the data preprocessing and processing from one instrument to another, from one operator to another.

On the basis of the knowledge about the applied techniques, e.g. about the chromatographic process and the mass spectrometric detection, relevant parameter, conditions and assumptions, e.g. assumptions in statistical modeling, and minimum requirements to safeguard the accuracy of the measurement may be checked automatically in all dimensions in the sense of a quality control.

The present invention is not limited to certain application areas. Some examples for analytical systems and methods and data formats which are suitable to apply the method, system and program of the invention to its two aspects and in accordance with the different proposals are the following:

A) Any possible combination of at least one analytical method generating separated, e.g. time resolved, signals online coupled via ion source unit with a mass spectrometric detector or online coupled via one common ion source unit or a respective ion source unit with several mass spectrometric detectors.
   E.g. chromatographic, electrochromatographic or electrophoretic methods directly coupled to the MS analyzer, e.g. liquid chromatography (LC), gas chromatography (GC), electrochromatography (EC), electrophoresis (EF), isotachophoresis (ITP).
   E.g. ESI (ElectroSpray Ionization), APCI-MS (Atmospheric Pressure Chemical Ionization), PI-MS (Photo-Ionization), MALDI (Matrix Assisted Laser Desorption Ionization), FAB (Fast Atom Bombardment), EI (Electron Impact) ionization techniques.
   E.g. quadruple, triple quadruple, TOF (Time of Flight), ion trap and linear ion trap, FT (Fourier Transformation) mass analyzers.
   All common types of mass spectrometric data can be used as a data input, e.g.: continuous spectral data, the data density in spectral axes is set by parameters of MS detections (like number of data points per Dalton); and centroided spectral data, reduced form of continuous data characterized by mean mass-to-charge value of mass peak and its height.

B) Any possible combination of at least one analytical technique generating separated, e.g. time resolved, signals in combination with at least one detector producing spectral signals or multiple signals in terms of acquisition of multiple signals in each separated or time point of measurement.
   E.g. Spectrophotometric (e.g. DAD, IR, fluorescence, optical dichroism, laser scattering).
   E.g. Electrochemical (e.g. coulometric)
   For spectrophotometric detectors, the use of a digital modeling of measurement/no measurement within some prediction interval (e.g. confidence interval) as suggested with respect to data such as LC-MS data, can be replaced by some continuous or discrete modeling for the number of measurement within some expected width of the spectral band of signals in an appropriate spectrum.
   An initial confidence interval used for Bayesian learning will not only be determined by an expected error of measurement, because its value is usually negligible, but also by an expected width of the spectral band of signals in appropriate spectrum.

C) Any possible combination of at least one analytical technique generating separated, e.g. time resolved, signals in combination with two or more detector units in serial or in parallel.
   E.g. combination of two or more mass spectrometric detectors or a combination of two or more detectors from examples A) and B).
   Example: A stream of analytes (e.g. eluate) is split after chromatographic separation into two or more particular streams with the same or different flow rates and they are introduced in parallel into different types of detectors. Resulting signals from both detectors represent complementary information in every time point of analysis independent in the measured quality/characteristics (e.g. mass-to-charge ratio, wavelength) and quantity (e.g. intensity/counts/absorbance).
   Some technical features of combination of two or more detectors (e.g. capillary length, various flow rates, flow cell or ion source design) cause various delays of signal acquisition for the same part of analytes stream resulting in incompatibility of time axes of data sets from the same run. The coordination of time axes occurs by alignment of signals for internal standards from all measurements on a relative time axis so that they possess the same relative retention times. This process is well known and often used in the chromatographic applications (e.g. elution indexes).

In all that and other measurement situations a substantial data reduction of separated, e.g. time resolved, signals may be obtained in terms of extracting of relevant signals and of denoising.

Alone or in concert with a suitable pattern recognition algorithm which is applied to the grouping results obtained according to the invention, the method and system of the invention can find its application for example in biology, biochemistry, clinical chemistry or human diagnostics. Some examples are:

1. Study of multivariate effects of external stimuli on biological systems in toxicology, cell and tissue biology.
2. Metabolic studies, identification of new metabolites, description of metabolic pathways and metabolic dysfunctions.
3. Recognition/Discrimination of normal from diseased individuals, treated from non-treated, various stages of diseases, types of diseases (aggressive vs. non-aggressive, slow vs. fast growing) in the explorative as well as predictive/prospective studies.
4. Marker screening in human diagnostics.

BRIEF DESCRIPTION OF THE DRAWINGS

The different aspects and proposals will be explained in more detail in the following on the basis of the illustrative, non-limiting example LC-MS spectrometry, in particular LC-ESI-MS spectrometry, on the basis of an appropriate statistical modeling of LC-MS data, in particular LC-ESI-MS data, and preferred embodiments of the grouping according to the first and second aspect of the invention. In this respect it is referred to illustrative figures, diagrams and flow charts as follows:

FIGS. 15 to 23 each are graphical representation of three-dimensional diagrams illustrating the denoising of raw data and grouping on the basis of the denoised raw data to identify a chromatographic peak and the relevant information extracted therefrom.

FIGS. 27 to 78 show grouping protocol pages 1 to 104 of a grouping protocol generated in the course of the grouping underlying the grouping result.

DETAILED DESCRIPTION

Figure 1:
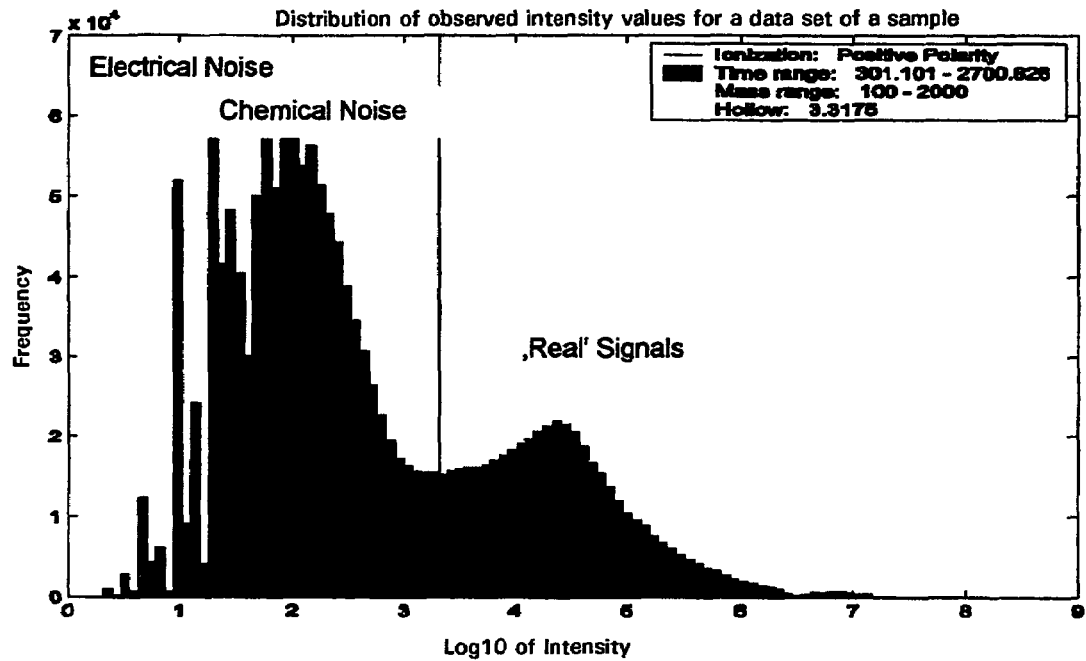
FIG. 1 is a histogram of the logarithm of the intensity of all data points of a set of data points obtained for a sample, in which a cluster of low-intensity data points caused by noise and a cluster with higher intensity values caused by real signals can be distinguished.

In the following such a measurement situation of LC-MS spectrometry, in particular LC-ESI-MS spectrometry, it is assumed, that three-dimensional measurement data are obtained, one data point or data tuple being defined by, first dimension, a scan number ($N_i$) or a retention time value ($t_i$) or a detection time value ($t_i$) and by, second dimension, a mass-to-charge value ($m/z_i$) and by, third dimension, an intensity value ($I_i$), possibly a count number. As made possible by the invention, the data preprocessing and processing is based on regarding these measurement values of a signal as realization of a three-dimensional random vector (generally of a multi-dimensional random vector).

Basic Considerations

For implementation with respect to a certain measurement situation, the characteristics of the used techniques and hardware should be analyzed with respect to characteristics of the signals or measurement data resulting therefrom. In this respect the characteristics of a three-dimensional (generally multi-dimensional) distribution of the measurement values to be obtained on the basis of the used techniques and hardware should be analyzed.

Generally, the source of a signal determines the shape and the parameters of the respective measurement value distribution. On the basis of such characterizations of the distribution of signals originating from different sources it is generally possible to filter out signals which come with a high probability from irrelevant sources. The parameters of the relevant distributions may be estimated sample specific for individual samples or globally for a number of samples, depending on the assumed source.

Signals of ions have a molecule-specific distribution of the retention time depending on the LC process, and an ion-specific distribution of the m/z value depending on the MS process. Under the condition that, at a certain scanning time and in a certain m/z, ions of a certain origin can be measured, the distribution of the intensity depends on: a) its vicinity to the mean retention time of the substance; b) the ionization process; c) the composition of the substances in the sample. Not only the concentration of a substance in the sample has a strong influence on the measured intensity, but also interactions between different substances, like possible suppression mechanisms with co-eluting substances, for example. The measurable consequences of these influences provide potentially interesting information about the composition of substances in the sample.

Herein it is generally referred only to constituents of a respective sample, which give rise to certain data parts in the measurement data and for which peaks have to be found in the measurement data. However, it should not be ruled out, that analytical techniques are used which produce certain other substances which were not already included in the original sample. It may even be that even no starting material on which this substance (herein denoted as product) is formed was originally included in the sample. Nevertheless, the additional substance or product may reflect characteristics of the sample, so that the identification of peaks originating from such additional substances or product may give information characterizing the sample. Of course, in an ordinary LC-MS analysis, there are generally no additional products besides the constituents of the sample to be characterized.

Noise Elimination

In the first step, signals that are electronic or chemical noise can be filtered out. A possible criterion for distinguishing those is the height of the intensity values measured. Electronic noise does not come from detected ions, and insofar as such noise is concerned the m/z value and the retention time have no meaning. Chemical noise is characterized in that always and everywhere (referring to retention time and m/z areas) weak signals are measured, which can be explained, for example, by the inevitable contaminations of all components of an LC-MS system. The distribution of the logarithmized intensity values of the chemical noise can easily be described by a normal distribution, the expected value of which is characteristically lower than the expected value of another signal cluster and higher than the one of a third signal cluster belonging to the electric noise. FIG. 1 shows a corresponding example. In the histogram of the logarithmized intensity value, there is a valley or minimum between the real signals and the chemical and electrical noise. Thus, one can draw a well-separating line between noise signals and no-noise signals, by finding the valley in the histogram of the logarithmized intensity values. This border line can be automatically determined for each individual sample by finding the minimum in the valley on the basis of conventional data processing techniques.

Systematic Artifacts of the Techniques

Substances that do not come from the sample provide little or no relevant information on the composition of the substances of the sample: The signals of the ions of the mobile phase and the ions of the added standards are artifacts of the measuring method. The parameters of their distributions can be determined globally for a number of samples or for groups of samples in blank measurements and in standards' measurements. It is possible to define identification and deletion templates on the basis of these measurements which identify, and, if desired, delete signals in the mass and retention space (area) most likely coming from the added standards or from the mobile phase, as they show m/z values and retention times typical for that. A 3D identification and deletion template, where typical intensities are included, would furthermore allow signals of co-eluting molecules and interaction phenomena to be detected and, if desired, to be deleted.

Spike Elimination

All other signals that have neither the typical properties of noise nor the typical properties of substances within the chromatographic process are called spikes. The main causes are thought to be all kinds of "cloddy" contaminations inside the measuring instruments, e.g. in the mobile phase, the column, the capillaries or in the ion source. That leads to ions showing up at times unexpected according to their chromatographic properties. Such signals cannot be reproduced and therefore should not be adopted in an actual statistical model. Signals of the spikes may be eliminated on the basis of the fact that they do not satisfy the distribution assumptions of real peaks. Threshold values for respective adaptation criteria may be determined within individual samples or globally for a variety of samples. If the grouping is based on appropriate conditions, the elimination of peaks can be effected automatically in course of the grouping.

Application of Distribution Models

In the following examples for distribution models which can be used in the illustrative context assumed here are given:

Electrical Noise

Preferably only the distribution of the intensity is modeled, without taking account of the time-axis and the mass-axis. In other words, the random vector only considers the border distribution of the intensity for characterizing electronical noise. It is assumed that the expected value exists for this distribution.

$$I(el) \sim F(\mu(el)) \tag{F1}$$

Chemical Noise

Again, preferably only the distribution of the intensity is modeled, without taking into account the time-axis and the mass-axis. A normal distribution is assumed as distribution type for the logarithm of the intensity.

$$\log_{10} I(ch) \sim N(\mu(ch), \sigma(ch)) \tag{F2}$$

Distribution of the Mass Measurement Error in the Measurement of the Mass-to-Charge Ratio For measuring the mass-to-charge ratio of an ion M* a normally distributed measurement error is assumed, taking into account the possibility that there is a small distortion:

$$MZ\text{-}mz(M^*) \sim N(\delta(M^*), \sigma(M^*)) \tag{F3}$$

In the simplest case one assumes that the measurement error concerns all ions equally, i.e. that $$\delta(M^*) \equiv \delta, \sigma(M^*) \equiv \sigma \text{ for all } M^*$$

is valid. It might be appropriate, though, to model the measurement error depending on the size of the mass-to-charge ratio of the ion or of the intensity.

Distribution of the Retention Time and the Intensity

The primary event is the elution of one single molecule of the substance at the time T, i.e. with the retention time T.

In the simplest model a normal distribution may be assumed for the retention time of one single molecule of a certain substance in a chromatographic process:

$$T \sim N(\mu_r(M), \sigma_r(M)) \tag{F4}$$

From this follows a Bernoulli distribution for the event of the elution of a molecule of a certain substance between scanning time $t_s-1$ and $t_s$:

$$I(M)|t_s \sim Bin(1, p(M, t_s)) \tag{F5}$$

with $$p(M, t_s) = \Phi(t_s | \mu_r(M), \sigma_r(M)) - \Phi(t_{s-1} | \mu_r(M), \sigma_r(M)) \tag{F6}$$

The assumption of a normal distribution is a gross simplification of the running processes. Its basic model, in the van Deemter theory depending on the radial diffusion process, the kinetic of the mass transfer and the turbulent diffusion, is already violated by the use of a gradient elution, but also through various other processes running in the chromatographic process (e.g. secondary interaction of the substances with the immobile or stationary phase, mixed retention mechanisms, mechanical and chemical changes of the immobile phase due to its aging). There are much more complicated models for the distribution of the retention times when measuring certain single substances, which describe the above mentioned processes in more detail. All models have in common that the underlying distributions are unimodal and that they deviate from the normal distribution rather in their skew or distortion than in their kurtosis.

More generally, one writes for (F6)

$$p(M,t_s)=F(t_s|M, \Delta t_s)-F(t_{s-1}|M, \Delta t_{s-1}), \quad (F7)$$

wherein F comes from a unimodal distribution class and is determined in its exact form by molecule-specific parameters and elution-specific, and thus time-dependent, parameters.

From (F6) or (F7) follows for the primary event that a certain ion of a certain substance is detected between two scanning times, a Bernoulli distribution, but with less probability of success, because additionally the event must occur that this ion is generated in the ionization process.

$$I(M)|t_s \sim \text{Bin}(1, p(M^*, t_s)) \quad (F8)$$

with $$p(M^*, t_s) = p(M^*, M) p(M, t_s) \quad (F9)$$

The intensity of a "real" signal in the LC-MS process is the frequency of detections of ions with a certain charge number of a substance between two scanning times. Under the simplifying assumption that the bernoulli-distributed primary events are independent, and if $N_M$ molecules were exposed to the chromatographic process, this is described by a binomial distribution:

$$I(M^*)|t_s \sim \text{Bin}(N_M, p(M^*, t_s)) \quad (F10)$$

It should be noted that suppression mechanisms may reduce p (M*, M). The sensitiveness of the MS instrument and the noise cutoff may lead to a censored observation of the realizations of this random variable.

Substances of the Mobile Phase

Continuous flow of the mobile phase into the ion source of the mass spectrometer causes, mostly very intensive, solvent cluster ions to emerge in the background of an LC-MS set of data. These signals do not show any properties of a chromatographic process that did occur, so that the frequency of one of their ions emerging between two scanning times $t_{s-1}$ and $t_s$ is a binomial distribution governed by the (earlier occurring) amount of input $N_M(\Delta t_s)$ and the probability of ionization:

$$I(M^*)|t_s \sim \text{Bin}(N_M(\Delta t_s), p(M^*, M)) \quad (F11)$$

with $N_M(\Delta t_s)$ being large for all $\Delta t_s$.

Products

If the applied analytical technique or techniques produces certain products, the applicable distribution model depends on the production mechanism. The man skilled in the art can set up an appropriate distribution model.

Data Pre-Processing and Processing

On the basis of such theoretical considerations and models a grouping of measurement data can be implemented for finding peaks of known and unknown constituents or products, in the present illustrative case for finding peaks of known and unknown ions.

At the beginning of the processing preferably the data are denoised, e.g. on the basis of an assumed logarithmized distribution of intensity value in accordance with FIG. 1. In the density histogram obtained from the real data the minimum between the real signals and the electrical and chemical noise is searched, and the signals attributed to noise are then eliminated. It is not necessary that a "statistical pattern recognition" or a "Bayesian learning" is applied. In the preferred approach proposed here the theoretical modeling according to distributions F1 and F2 serves only to give the background of the noise elimination approach. A "statistical model" is applied only insofar as that the theoretical model predicts that the boundary between noise signals and real signals has to be searched in the valley of the histogram.

However, for the grouping of signals remaining after the denoising preferably Bayesian learning is applied to group data in the groups or intervals which presumably are associated to a respective constituent of the sample or of an ensemble of samples or a product resulting from one or several of the techniques applied to the sample or samples.

The Bayesian learning in a preferred embodiment basically serves to group signals or data tuples of interest, which presumably are associated to a respective constituent or product, within confidence intervals having a width depending on the techniques used, e.g. a width of about ±0.2 Da for quadruple mass spectrometers, about ±0.002 Da for time of flight mass spectrometers and ±0.0002 Da for Fourier transformation mass spectrometers. The choice of the confidence interval (and thus the expected measurement accuracy) depends on the method of separating the ions in the MS analyzer. The values mentioned here are typical measurement inaccuracies to be expected under conventional measurement conditions. Part of the values might be different if the mass parameter is set differently.

For these groups of signals obtained from the grouping, a reduction of dimension in the kind of a selected ion monitoring (SIM) chromatogram may be obtained by combining all data points in the m/z dimension within the resulting confidence interval for respective time value or scan number. The grouping preferably is effected not only on confidence intervals obtained from Bayesian learning but also on the basis of additional conditions. In particular, a distinction between signals associated to a respective constituent or product and other signals, such as artifacts, may be obtained on the basis of the condition, that the intensity values within a respective confidence interval shall satisfy at least one or several of a intensity cutoff condition, a unimodality condition and a kurtosis condition. The intensity cutoff condition is based on the assumption, that the area under a real peak shall exceed a threshold for being acknowledged as a real signal. The unimodality condition and the kurtosis condition are based on the assumption that real signals and other signals, such as artifacts, can be distinguished on the basis of the shape of the signal.

Starting from given start values, e.g. from start values originating from measurements on external standards, the respective confidence interval is determined or improved (in particular narrowed) by Bayesian learning. Start values originating from measurements of external standards may be adapted to a particular measurement situation or system on the basis of internal standards, in case of LC-MS spectrometry, on the basis of internal standards which are eluted together with the respective sample or which are added to the respective sample, by applying the algorithm selective to signals which can be attributed to the internal standard. Afterwards, the signals may be eliminated by applying a respective deletion template, if desired.

It should be added, that also the signals which have to be attributed to the mobile phase can be eliminated using a corresponding deletion template. This is done preferably before the grouping of signals originating from constituents or products of interest or originating from unknown constituents or products.

Sample Specific Learning of the Measurement Error Distribution $N(\delta, \sigma)$ The measurement error distribution can be learned with the help of the signals allocated to the added standards. The real mass-to-charge ratios of those are known, so that any deviances may be observed. Preferably, a Bayesian posterior estimate is used, assuming that the measurement error distribution is the same for all substances and ions. Thus, the prior distribution chosen for the Bayesian learning is implicitly checked, since in the case of too high informatively and if the assumed measurement error was too small no signals can be found that are collected as peaks of the ions of the standards in the grouping process. The posterior distribution can be used for testing, whether the measurement error within a respective sample can be tolerated. If this is the case or if one decides to implement the algorithm without such a test, the posterior distribution of the measurement error obtained from Bayesian learning on the data relating to the added standards serves as prior distribution for detecting peaks for ions in unknown substances (compare FIG. 3).

Another option would be a Bayesian posterior estimate of the measurement error distribution assuming an unequal measurement error distribution within the observed measurement area.

Detecting the Signals of a Known Substance

Initial assumption: Of the substance or sample, to which the LC-MS techniques are applied, the mass-to-charge ratios of one or more ions and the retention time of the associated peaks are known, e.g. from older measurements effected with the same system. Experiences with the mass spectrometer allow an uncertain statement about a confidence interval of the measurement error, e.g. "with 90% certainty 95% of the observations miss the real mass-to-charge ratio of the ion by maximum ±0.4 Da". This serves for determining a prior distribution for the unknown parameters of the measurement error distribution, with the help of which a predictive confidence interval for the m/z values (m/z windows) of the signals of the ions can be established.

At a start scanning time before the known retention time, it is started to search for observations within the m/z window around the known real m/z value. When such a signal is found, immediately a new predictive confidence interval is formed according to the Bayesian update scheme for the m/z value of ions of the same type in the next scan. If there are no observations over at least one or more scans within the sequential or current m/z window, the peak is considered completed and further signals along in the vicinity of this m/z trace are considered not to belong to the same ion. The group of signals whose scanning time comprises the preset retention time, is identified as peak of the respective standard ion (compare FIG. 13).

Grouping of Several Signals as Peak of an Unknown Ion

The searching for ions with an unknown m/z value is started on the basis of a prior distribution for the parameters of the measurement error distribution. Starting in the first scan, a predictive interval for ions of the same type in the next scan can be calculated for each observed m/z value by means of Bayesian learning. After the detection of the first signal the signals are grouped according to the same scheme as for known substances. Since there is not the same certainty as with the known substances, however, that the found "similar" signals are a real peak, further criteria are used to distinguish real peaks from other possible events, e.g. artifacts of the techniques applied.

In the sense of a modeling, the following events may have occurred, when several signals in successive scans within a sequential m/z window are found:

1. Noise event
   Accidental proximity of chemical noise ions lying above the noise cutoff 2. Peak (peak event)
   The signals belong to an ion of a chromatographically separated molecule of the sample.

3. Several overlapping peaks (peak events)

4. Permanent peak
   The signals belong to ions of the mobile phase

5. Spike (spike event)
   Something different, e.g. several signals of a solved contamination were measured or other non-systematic artifact.

Distinguishing Peak from Noise Event

In order to distinguish a peak from the noise event, one may set an intensity cutoff, the value of which may be determined in a valley histogram within the sample (compare FIG. 1).

Examples for Determining an Intensity Cutoff:

The observed intensity values used for determining the intensity cutoff should have a probability as low as possible and should all be noise events. This is the case when, for example, their maximum value or their mean value are outside the 3-σ area of the intensity of the noise. The variance of the noise intensity may be detected in the valley histogram for a respective individual sample.

Deriving from that, one may also determine a somewhat weaker intensity condition applied to the sum of the intensity values, which, according to the intensity condition, shall exceed a minimum value to be identified as a real peak. This is also useful for distinguishing from spikes, as those typically occur shorter and with less intensity than real peaks.

Distinguishing Peak from Spike

For distinguishing peaks from spikes one may use the shape of the intensity values along the time window, which should correspond to the histogram of a unimodal distribution with an approximately normal kurtosis. This is due to the variation in time of the success probabilities (F7) in the distribution model (F10).

Therefore, each parameter of the histogram, that says something about the deviance from the unimodality or about the kurtosis, may be used for distinguishing.

Threshold values for these parameters should be determined from several samples considered in combination, e.g. in the blank and standards measurements.

Distinguishing Peak from Overlapping Peaks
   Appropriate criteria are:
   Deviance from unimodality
   Bayesfactor of model (F11) and a mixture of several models of type (F11)

Distinguishing Peak from Constant Peak
   Appropriate criteria are:
   Deviance from unimodality
   Proximity to learned m/z values in blank measurements
   Bayes factor of model (F11) and model (F10)

Bayesian Learning or Update Scheme

Based on a current m/z window which is defined by an applicable distribution it is decided when the first or next data point is found whether this data point presumably belongs to a respective constituent or product or not. If the data point falls in the current mass window then it is decided that this data point belongs to a respective constituent or product in the sense of candidate membership of a respective group, and if the data point does not fall in the current m/z window then it is decided, that this data point does not belong to said constituent or product.

In case of an internal standard the initial m/z window corresponds to an m/z interval which is established around the known m/z value so that the known m/z value of the internal standard and m/z values around this known value are included in this interval. As measurement error distribution a normal distribution is assumed which is centered on the known m/z value.

In case of unknown substances (constituents or products) the initial m/z window covers the whole area of the m/z axis in which signals originating from unknown constituents or products are expected. Since the "real" m/z value is not known yet, not the normal distribution but instead a distribution of normal distributions which corresponds to the so-called t-distribution is assumed.

When the first data point is found, then it is decided whether this data point presumably belongs to a respective constituent or product or not. If the data point falls in the initial m/z window, then it is determined, that this data point belongs to a constituent or product and on the basis of this data point the applicable distribution (normal distribution in case of a known substance and t-distribution in case of an unknown substance) is updated by setting the respective parameters of the distribution on the basis of this data point. From this updated distribution then a new m/z window is determined. If the next data point following along the time axis or scan axis falls into this m/z window, then it is assumed, that this data point belongs also to the same substance.

The m/z windows are preferably defined such, that the majority, e.g. 99% of all data points which belong to the same substance, fall into this m/z window according to the current distribution.

Finding groups of data points which fall in the current m/z interval or window established on the basis of a distribution of measurement errors is generally not a sufficient condition to identify these data points as a peak belonging to a respective substance. Accordingly, generally additional conditions should be applied.

One condition is the mentioned intensity cutoff condition or intensity condition.

Another condition is the unimodality condition which allows a very effective discrimination between real peaks and other phenomenon. Not only peaks can be found but also overlapping peaks may be resolved. A check for fulfillment of the unimodality condition may be implemented as follows: The histogram of the measurement values is integrated or summed up to a first curve which ideally corresponds to the so-called S-curve. This first curve is then differentiated to obtain a second curve which represents the original discrete data points. By summing up the positive differences between the second curve and the measurement values of the histogram (distribution) a measure for the deviation from the next unimodal curve is obtained. This measure is compared with a threshold value. The unimodality condition may be assumed to be fulfilled if the measure is smaller than e.g. 10%.

Checking for unimodality is not the only appropriate way to find real peaks. Additional characteristics of assumed distributions of the measurement value may be considered, e.g. the kurtosis of the distribution or histogram. The term kurtosis refers to the fourth central moment divided by the second central moment squared of a distribution or histogram. On the basis of a kurtosis value of three for the normal distribution a deviation of about ±0.1 may be admissible for fulfilling a corresponding kurtosis condition.

According to the preferred embodiment considered here, no Bayesian learning, no Bayesian learning or update scheme is applied to the finding of measurement values along the time axis or scan number axis. The Bayesian learning or updating is only applied to the finding of measurement values along the m/z axis. However, in other circumstances a Bayesian learning with respect to all relevant axes may be appropriate.

Bayes Learning in General

In Bayesian statistics, probability distributions quantify the uncertainty when hypothesizing about (future) events and they can also be used to quantify the uncertainty hypothesizing about unknown "true" states of the world.

Bayesian learning theory is the framework that prescribes how the current level of uncertainty is updated, if new evidence or information, data, concerning the future event or the unknown state of the world arrives. The basic formula for this update mechanism is the so-called Bayes formula. It was first published in 1763, by Reverend Thomas Bayes, two years after his death. Bayes, Thomas: "An essay towards solving a problem in the doctrine of chances." Philosophical Transactions of the Royal Society (1763) 53:370--418. In its simplest form, if H is a hypothesis and E is evidence, it states $$Pr(H|E, C) = Pr(H|C) Pr(E|H, C)/Pr(E|C),$$

so that $Pr(H|E, C)$ is the probability of belief in H after obtaining E given a current context C (state of uncertainty about H) and $Pr(H|C)$ is the prior probability of H before considering E given C. The left-hand side of the theorem, $Pr(H|E)$ is usually referred to as the posterior probability of H.

If data is collected iteratively or comes in a flow, any posterior distribution (that is a collection of posterior probabilities for a set of hypotheses and any subset of them) at one point is a prior distribution at the next point. Also, two posterior distributions can be combined to form a combined posterior distribution.

Determining the Prior Distribution about the Mass-to-Charge Measurement Error of Some Instrument For an expert who is asked to specify the length of some m/z interval where he or she would expect that "most" measurements of ions from the same type show up, it will generally be no problem to give a corresponding estimate. In addition, the expert, when he or she is asked to define how certain he or she is about said information (e.g. C=80 or 90%) will generally have no problem to give such an estimate. It is just like if one would consider to bet on the outcome of some experiment. Interpreting "most" in terms of some predictive interval for a percentage of $(1-\alpha)*100\%$ of all measurements, the basic information for determining a prior distribution as basis for a Bayesian learning or update scheme is available. These statements can easily be combined by the methods of Bayesian statistics to form a prior distribution. The effect of the specified certainty is that the lower it is the higher is the influence of the incoming data on the posterior distribution. Criticizers of Bayesian statistics often claim it would be best to let the "data speak for themselves" such that in many applications of Bayesian statistics one tries to minimize the influence of the prior distribution. In the present context, though, it is generally crucial that the certainty C is not too small, because one needs some certainty that measured values or ions of some type are near to the true m/z value of the ion such that the algorithm can distinguish measurements of the specified ions of the standards from measurements of ions that elute at the same time and have slightly different m/z values. And it will generally be no problem for experts to make a statement like this: "Using a quadruple analyzer, I expect with 90% certainty a mass inaccuracy of ±0.2 Da. Such a statement is sufficient to initialize a Bayesian update or learning scheme in the present context.

Bayesian Learning of the Mass-to-Charge Value of Some Unknown Ion

A preferred embodiment of a Bayesian update or learning algorithm is based on a Bayesian model of normal data with a conjugate prior distribution as described in Gelman, Carlin, Stern, and Rubin (1995, Section 3.3): Bayesian Data Analysis, ChapmanHall/CRC. The page numbers refer to the CRC reprint, 2000.

The process of Bayes-learning starts with some given N-Inv-$\lambda^2$ prior distribution with parameters $\mu_0$, $\sigma^2_0$, $\kappa_0$, and $\nu_0$ (formula (3.6), page 71).

The parameters $\sigma^2_0$ and $\nu_0$ have been set up using the specifications on the mass error distribution of the expert and potentially already been updated for a given LC-MS measurement of some sample by the observed peaks of the ions of the internal standards with known true mass-to-charge values.

To specify $\mu_0$ and $\kappa_0$ for unknown substances, a flat prior is taken such that on the observed interval [L,U] of mass-to-charge values the ratio of the maximum probability of the normal distribution at its expected value (namely the middle of this interval) to the minimum value (namely in L and U) is equal to 1/0.9999.

Now it is assumed, that some ion(s) were detected with mass-to-charge value $y_1$ at scan time $t_1$. The updated joint distribution for their unknown true mass-to-charge value $\mu$ measured with variance $\sigma^2$ is also some N-Inv-$\lambda^2$ distribution with updated parameters $\mu_1$, $\sigma^2_1$, $\kappa_1$, and $\nu_1$ according to formulas below formula (3.7) on page 72.

From these one can calculate the marginal posterior distribution for $\sigma^2$ and $\mu$ as given in formulas (3.9) on page 72 and the first formula on page 73, respectively. The uncertainty about the true variance $\sigma^2$ is thus described by some scaled Inv-$\lambda^2$ distribution with $\nu_1$ degrees of freedom and scale $\sigma_1^2$. The uncertainty about the true parameter $\mu$ is thus described by some t-distribution with $\nu_1$ degrees of freedom, with location $\mu_1$, and scale $(\sigma_1^2/\kappa_0)^{-0.5}$.

From these one can calculate the posterior predictive distribution that codes the expectations about the mass-to-charge value in case ions of the same type get detected in the next scan using formulas (2.7) and (2.8) on page 32. The uncertainty about the next mass-to-charge value is also described by some t-distribution like the uncertainty about the true mass-to-charge value $\mu$ of these ions. The distribution has the same degrees of freedom $\nu_1$ and location $\mu_1$ as the distribution describing the uncertainty about $\mu$, but with a larger scale, resulting from the knowledge that the measured values spread around the true parameter according to the unknown variance $\sigma^2$. The scale is thus $(\sigma_1^2+\sigma_1^2/\kappa_0)^{0.5}$.

An $(1-\alpha)$-interval of this distribution is given by the $\alpha/2$ percentile and the $(1-\alpha/2)$-percentile of the corresponding t-distribution. This interval defines the mass window for scan time $t_2$.

If some ions are detected there, $\mu_1$, $\sigma^2_1$, $\kappa_1$, and $\nu_1$ take over the role of $\mu_0$, $\sigma^2_0$, $\kappa_0$, and $\nu_0$, and the same learning process starts again as described above.

Additionally, reference is made to the second edition of the textbook referred to in the foregoing: "Bayesian Data Analysis" by Gelman, Carlin, Stern and Rubin (2003, Chapman & Hall/CRC) and to the textbook "Data Analysis: A Bayesian Tutorial" by D. S. Sivia (1996, Oxford University Press). The textbooks include all information needed to set up a Bayesian learning scheme suitable for measurement data grouping in the context of the measurement situations considered here and in the context of other measurement situations.

Besides the so-called "normal model with conjugate prior" which is considered here as distribution model with respect to the m/z axis, also other distribution models may be applied, e.g. the so-called "multinomial model with conjugate prior", in which the discreteness of the measurable m/z values can be taken into account.

It should be added, that the different formulas e.g. from the textbook "Bayesian Data Analysis" cannot always be solved exactly in closed form, so that a numerical solution might be necessary. For processing efficiency it might even be useful to calculate approximate solutions, e.g. for calculating the inverse of students t-cumulative distribution function. Such numerical or approximate solutions of the relevant formulas can easily be implemented by the man skilled in the art.

Preferred Implementation of a Bayesian Learning Scheme

As already indicated, the grouping of measurement data for samples to be characterized with respect to constituents or products, in particular unknown constituents and products is based on a Bayesian learning scheme which takes into account grouping results obtained for measurements of standards. Additionally, preferably grouping results concerning blank measurements are taken into account.

In this respect a "global" processing scheme is proposed, as follows:
1. Processing a set of measurements of samples containing internal standards only ("standards' measurements")
   Output:
   a) For each standard substance s=1 ..., S, an automatically determined number of intervals on the m/z axis, in which data points caused by ions of the respective substances were found.
   b) A posterior distribution for the mass measurement error.
2. Processing a set of measurements of background without injecting any sample ("blank measurements")
   Output:
   An automatically determined number of intervals on the m/z axis, in which data points caused by ions of substances in the mobile phase were found.
3. Processing the set of measured samples
   Output:
   For each sample an automatically determined number of peaks caused by ions in the sample.
   A peak is described by
   a) an interval on the m/z axis (mass window) and
   b) an interval on the time axis (time window).
   These two intervals describe the space in time and m/z axis, in which, according to the peak-finding algorithm, measurements of ions of the same type appeared and in which most measurements of that type are expected to appear in other measured samples as well.
   In addition a peak is described by
   c) its intensity, that is the sum of intensity values of all data points that give rise to that peak.

With respect to the processing of standards, the following "local" processing scheme or the following steps are proposed:
For a single measurement, do
1) Noise elimination
2) Finding peaks of specified ions of standard substances
   a. Check mass measurement error distribution
   b. It is sufficient, update mass error distribution
3) Finding peaks of ions that appear in the same time interval as the specified ions.
   These are considered to be potentially caused by internals standards as well.
4) Time standardization For a combination of the information in a set of standard measurements
5) Find those peaks that appear in a certain percentage (e.g. 80% or 50%) of measurement where the rectangle of time- and mass-window overlap at least to some specified extent. The mass windows are combined to form the "standards' deletion template". The time windows of the "standards' deletion template" in new measurements will be determined individually in the respective measurement using the peaks of specified ions of the internal standards within that measurement itself.

6) Combine of all standards measurements the information about the mass error distribution of the instrument (Bayesian learning) for a finishing posterior mass error distribution.

Figure 2S:
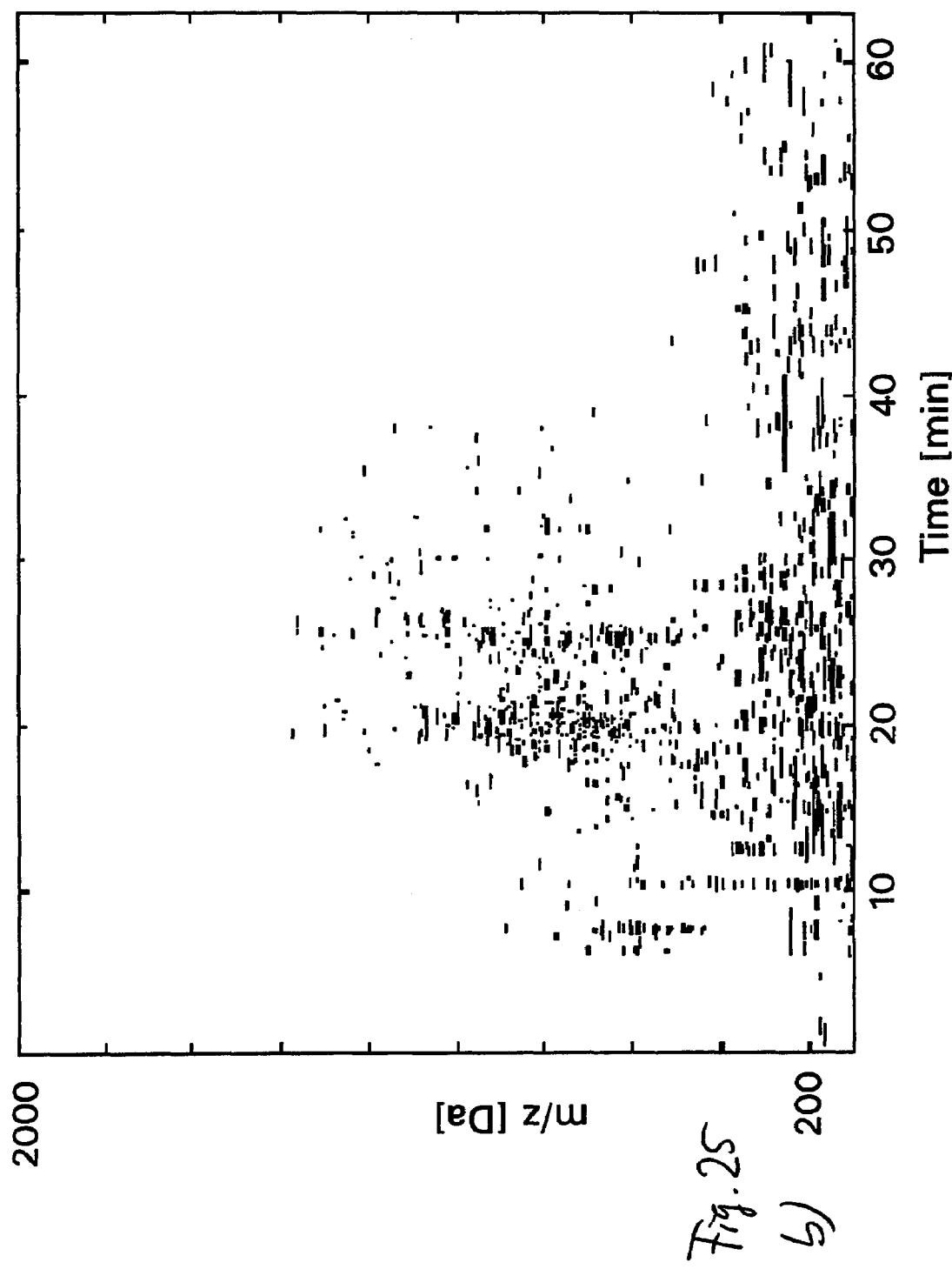
FIG. 2 shows schematically grouping results obtained for different ensembles of raw data and the combination of these grouping results to obtain secondary grouping results.

As "single measurement" a complete measurement data set obtained for one sample including at least one internal standard is meant here. Often, such standard measurements are effected for a plurality of samples or effected several times for one respective sample, e.g. 50 times. The "single measurement", as assumed here, refers to one of such data sets, to which the algorithm is applied to find the time- and mass-windows. If the standard measurements have been effected for a plurality of samples or if the standard measurement has been effected several times for respective samples then the time- and mass-windows obtained for each single measurement may be combined to respective combination time- and mass-windows, e.g. to correspond to a respective envelope window including all respective individual windows or to correspond to an average window which covers a certain percentage of the overall area or on the basis of the overlapping of the windows (compare step 5). To advantage, the combination of the individual windows may be effected on the basis of Bayesian statistics, so that confidence values associated to the respective individual window are combined to a confidence value of the resulting combination window. A combination of respective windows for a number of different single measurements is illustrated in FIG. 2.

With respect to processing blanks, the following "local" processing scheme or the following steps are proposed:

For a single measurement:
1) Noise elimination
2) Finding mass traces of ions of substances in the mobile phase For a combination of the information in a set of blank measurements
3) Find those mass traces that appear in a certain percentage (e.g. 80% or 50%) of measurement where the mass window overlap at least to some specified extent. These are combined form the "mobile deletion template".

Again the term "single measurement" refers to a complete blank measurement data set. The grouping results obtained for a set of blank measurements may be combined according to step 3).

With respect to the processing of samples to be characterized with respect to constituents or products, the following "local" processing schemes or the following steps are proposed:

For a single measurement:
1) Noise elimination
2) Finding peaks of specified ions of standard substances
   a. Check mass measurement error distribution
   b. If it is sufficient, update mass measurement error distribution
3) Finding peaks of other ions in the sample
4) Time standardization For a combination of the information in a (sub)set of sample measurements
5) Find those peaks that appear in a certain percentage (e.g. 80% or 50%) of measurement where the rectangle of time- and mass-window overlap at least to some specified extent. These are combined to form typical peaks for the (sub)set of samples.

Again, the term "single measurement" refers to a complete measurement data set obtained for a sample. If the measurements have been effected several times with respect to one particular sample or if a plurality of samples shall be considered in combination then it is possible to combine the respective single grouping results in accordance with step 5).

A combination of grouping results obtained for different ensembles of measurement data may be applicable for example, if several similar samples have been measured, which, however, have to be considered as "individual samples", which, on the other hand, include in combination information of interest. An example is samples originating from patients, who have the same disease. A combination of respective group might facilitate the identification of patterns in the data which reflect this disease.

It should be added, that the application of the standards' deletion template is an option which could be implemented as additional substeps c. of step 2). However, often it will be appropriate to maintain the grouping results achieved for the internal standards, since valuable additional information may be obtained from these grouping results, which might be helpful in the further analysis. For example, information concerning the mutual influencing of the substances may be derived therefrom.

Noise Elimination

Each of the proposed processing schemes includes noise elimination as a first step. As already indicated, the main criterion to distinguish noise from signal is the size of the intensity of a data point. Electrical noise is not caused by detected ions and thus the m/z value and retention time have no meaning. Chemical noise shows up everywhere and anytime as weak signals. The distribution of logarithmic intensities is well modeled by a mixture of three distributions: two normal distributions with low and high mean value for chemical noise and signal respectively and some multimodal distribution for the very small intensities of electrical noise. A good separation between noise with its low intensities and signal can be found in the hollow of the histogram of logarithmic intensities (see FIG. 1). The hollow is determined for each sample individually and automatically.

FIG. 1 shows the histogram of the logarithm of the intensity of all data points in one sample. One sees regions with different behavior: On the very left, no smooth distribution seems to rule the generation of data. Aside from that, two main clusters can be distinguished: A cluster of low-intensity data points and another cluster with high intensity. The data in the low-level cluster are assumed to be caused by noise.

It should be added that according to the proposals the noise elimination is effected globally with respect to the data representing a single measurement for one sample. However, good results with respect to denoising may be obtained, if a m/z value or/and time value specific noise elimination is implemented, possibly even a substance-specific noise elimination in a respective subset of the overall data set.

Checking Mass-Error Distribution

The use of internal standards allows checking the prediction of the expert with respect to the expected measurement value and the expected percentage of data points within said measurements error and therefore the initialization parameters for the Bayesian update scheme on the basis of the measurements effected with respect to the internal standards. This may be done as follows:

For each of the specified ions of the internal standards one calculates the deviance of the observed m/z values of the detected data points to the true m/z value, the so-called residuals. If the actual mass measurement error of the given measurement is larger than what the expert expected, this will have mainly two effects:
1. If it is much larger, the peak finding algorithm will not detect those data points that form a peak caused by one or more of the specified ions.
2. If it is somewhat larger, due to the specified uncertainty the expert has about the predictive interval, the actual size of the predictive interval will become wider than the prior one.

This can be visualized by box plots. The algorithm preferably displays warnings, if one or both effects are observed for some measurement.

Figure 3:
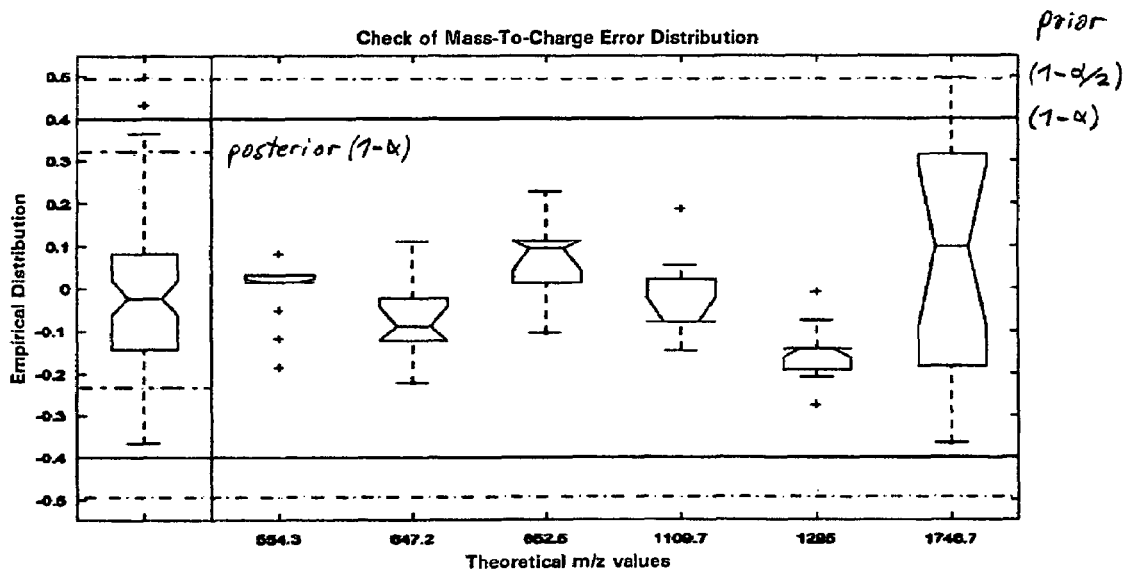
FIG. 3 is a boxplot diagram allowing a check of a mass error distribution on the basis of empirical distribution data.

FIG. 3 shows an example for such a boxplot diagram. Along the ordinate the measurement error $\Delta m/z$ is outlined and along the abscissa theoretical values for certain internal standards. For each standard a box having an upper and a lower part is shown, the upper and lower box part each representing 25% of all respective measurement data. The results for the internal standards are combined, which is shown in the most left part of the diagram. The uninterrupted horizontal lines represent the prior $(1-\alpha)$-predictive interval (here: prior 95% interval), the horizontal dashed lines represent the prior $(1-\alpha/2)$-predictive interval (here: prior 97.5% interval) and the short dashed pointed horizontal lines in the most left part represent the posterior $(1-\alpha)$-predictive interval (here: posterior 95% interval).

For the present case the expert had predicted an error interval of ±0.4 Da. The mass window after the Bayesian learning overall standards lies in the interval represented by the dashed pointed lines, i.e. about −0.22 to 0.31 Da, which is within the interval predicted by the expert. In the present case all peaks of all specified ions were found, such that the measurement and initialization has passed the mass measurement error control.

Learning Mass Measurement Error Distribution

If some measurement has passed the check of its mass measurement error on the basis of the internal standards, all residuals may be used to update the prior mass measurement error distribution, which now may be used for finding unknown ions. The certainty about the predictive interval is now much higher than before, in many Bayesian settings it can be expressed as a combination of prior uncertainty and the number of observations (here: the number of residuals). This is a good way to process, if the standards' measurements were made randomly among all other measurements, such that a change in the performance of the instrument would have been detected in the standards' measurements. If the posterior, though, is intended to be used for future runs, it would be wise to only keep the information about the new length of the predictive interval, but to lower the certainty about it. This is for many Bayesian models easy to introduce in the formula of the posterior. In effect, the procedure will be more sensitive to changes in the behavior of the instrument.

Time Standardization

On the basis of internal standards a standardization of the time or scan number axis (time standardization) may be effected.

The internals standard concept originates from the theory of elution indexes in partition liquid chromatography and it is used in the present context under simplified assumptions. One assumes that though random fluctuations of mobile phase composition cause shifts in retention times, the elution order of separated substances remains unchanged, and that by gradient elution, distances between retention times were linearized. The retention times between the retention of two internal standards is standardized with linear functions. One can use any set of substances for internal standards that are measurable in the given experimental setting and that covers a range of mass/charge values and with retention times that spread over the time interval of observation.

The time standardization basically amounts to a mapping of the measured time axis or scan number axis on an assumed real or theoretical or common time axis or scan number axis. By means of this time standardization apparatus-dependent deviations may be eliminated.

The concept of time standardization can be generalized or extrapolated to the situation, that on the basis of a separation, e.g. time series, achieved on the basis of at least one first analytical technique a plurality of different further techniques are applied each having their own time axis or other characterizing measurement value axis on which the separation achieved according to the at least one first technique is mapped. These different time axes or characterizing measurement value axes may be synchronized or standardized on the basis of internal standards showing up in the measurement data part obtained from the respective further technique.

Embodiments

As indicated, according to a preferred embodiment of the method, generally several samples are analyzed, namely blank samples, samples including only standards, real samples, calibration samples and real samples including internal standards. With reference to one real sample at least one associated standard measurement and at least one associated blank measurement should be used as basis for the initialization of the grouping with respect to the measurement data obtained from the real sample. Accordingly, first the measurement data for the blank sample and the standard sample have to be obtained before the grouping for the real sample is started. However, it should not be ruled out, that the data preprocessing and processing is effected globally with respect to a data set including all measurement data for said samples. Further, it should not be ruled out, that a data preprocessing and data processing is already effected simultaneously in course of effecting the techniques providing the measurement data. In particular, some kind of "online data processing" may be implemented which is interleaved with the collection of the measurement data provided by the detection hardware.

The grouping and Bayesian learning of measurement data of real samples including unknown substances and internal standards is preferably effected as follows: First it is searched along preknown m/z traces, in which internal standards are expected, for corresponding data points. For this search the Bayesian learn algorithm is initialized with the known true m/z values and predictive mass-to-charge intervals obtained from measurements on standard samples. Since the true m/z value is known, the normal distribution is assumed.

After the Bayesian learning on the basis of the internal standards, the Bayesian learn algorithm is initialized for the search after unknown ions. For this search first an even distribution of measurement error over the whole m/z axis is assumed, since it is not known, which m/z values have to be expected. After the first data point has been found, then a measurement error distribution centered on the m/z value of this data point is assumed to initialize the Bayesian learn algorithm for the further search. Since the true m/z value is unknown, the t-distribution instead of normal distribution is taken. For the further search of additional data points belonging to the same peak the t-distribution is initialized such that the resulting predictive mass-to-charge interval or window still reflects the predictive mass-to-charge interval or window obtained from the grouping of the data originating from the internal standards. Each additional data point which falls in the current mass-to-charge window, generally changes the average m/z value, on which the t-distribution is centered and generally also the width of this distribution and accordingly the resulting predictive mass-to-charge window. However, since a single data value has relatively low influence on the predictive mass-to-charge window obtained from the distribution, the influence of a single data point on the average m/z value and accordingly on the location of the predictive mass-to-charge window is higher than the influence on the width of this window.

An example of a process for finding peaks of specified ions of internal standards on the basis of Bayesian modeling is elaborated in somewhat more detail in the flowchart or data flow type diagram of FIG. 4a to 4d. On the basis of a predictive interval $(1-\alpha)$ and a certainty P estimated by the expert and a respective m/z value of a specified ion, a prior distribution for measurements of such an ion is established. By applying the probability calculus the first mass window is determined. To be on the safe side the algorithm is started with a predictive interval $(1-\alpha/2)$ which is larger than the predictive $(1-\alpha)$ interval estimated by the expert. The current mass window, e.g. the first mass window obtained on the basis of the expert predictions and correspondingly subsequent current mass windows stay the same as long as no measurement falling in the respective current mass window is observed in the subsequent scans.

If a measurement value is observed which falls in the current mass window (cf. scans i and i+1 in FIG. 4a) then the posterior distribution for measurements of such an ion is obtained by Bayesian learning and by applying the probability calculus the respective following current mass window (cf. second mass window or third mass window in FIG. 4a and FIG. 4b) is obtained.

After having found the first measurement value falling in the first mass window, the search for further data points belonging to the same substance may in principle be aborted when no further data point falling in the current mass window is found in the next scan. However, this abort condition is too severe, since it may well happen that in one or some few sequential scans no mass point is found which falls in the respective current mass window. Accordingly, it is preferred that a certain number of scans giving no additional data point is allowed before the search for further data points associated to the same ion is aborted, assuming, that now all data points have been found which belong to one substance or ion. This is exemplified in the diagram (cf. FIG. 4b), where the abbreviation NaN stands for "Not a number", if i.e. for the situation that in the next scan after establishing a respective current mass window no data point is found which falls in this current mass window. For example, one may allow that only one or two subsequent scans in which no data point falling in the current mass window is found are allowed without aborting the search.

Also in the course of finding specified ions of internal standards it may be appropriate to additionally apply other conditions, e.g. the unimodality condition and the intensity condition. This can be done, for example, on the basis of four data points which were found sequentially to fall in a respective current mass window and which accordingly are presumed to be associated to the same ion. An abortion of the search may additionally be based on at least one additional condition of this kind, e.g. a unimodality condition and an intensity condition. After abortion of a search the Bayesian learning algorithm may be newly initialized for the search for data points associated to another specified ion of a respective other internal standard.

Figure 4:
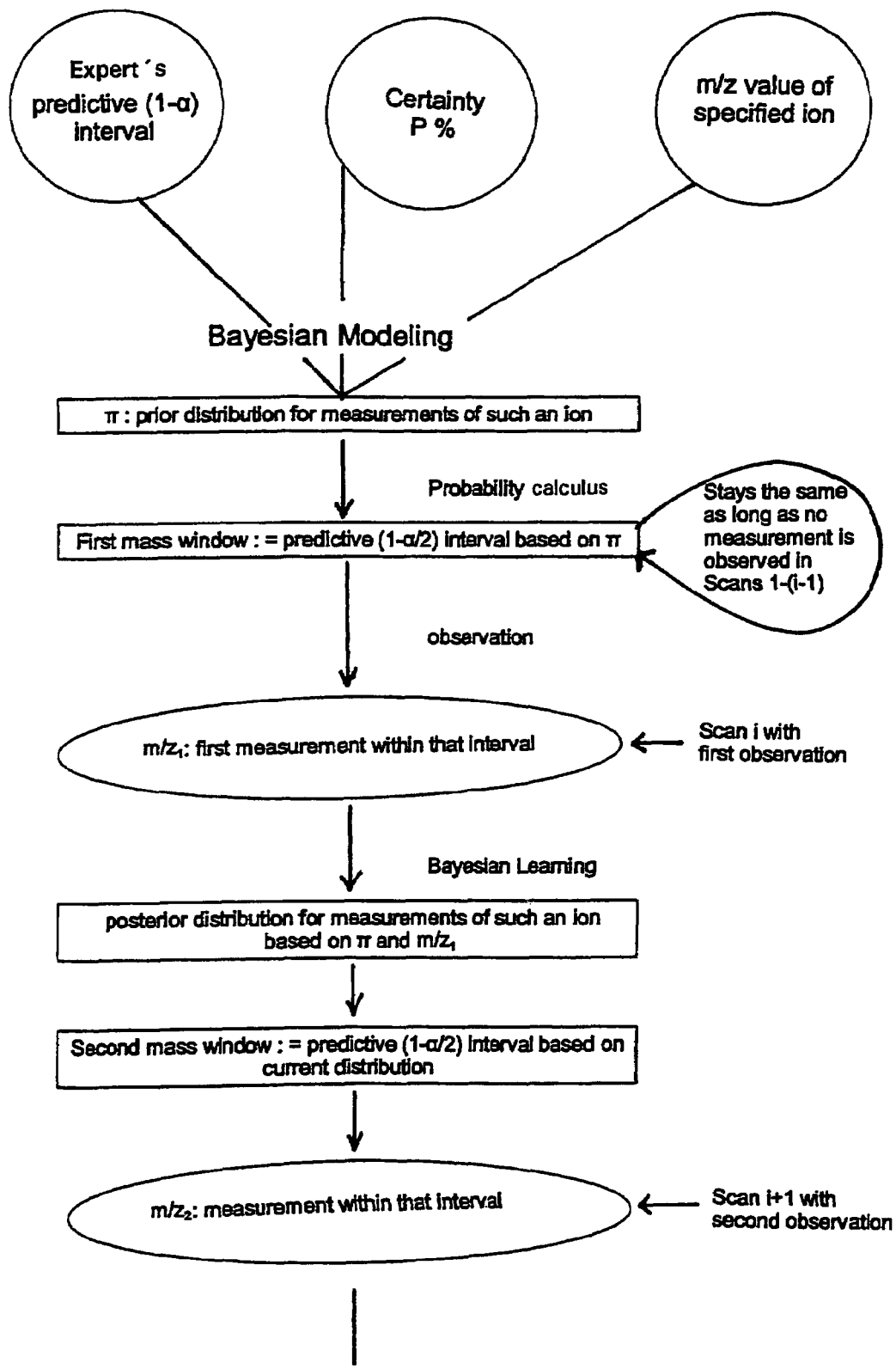
FIGS. 4a to 4d each show a flow chart or data flow type diagram and resulting grouping data illustrating an embodiment of the grouping to find peaks of specified ions of internal standards.
Figure 4:
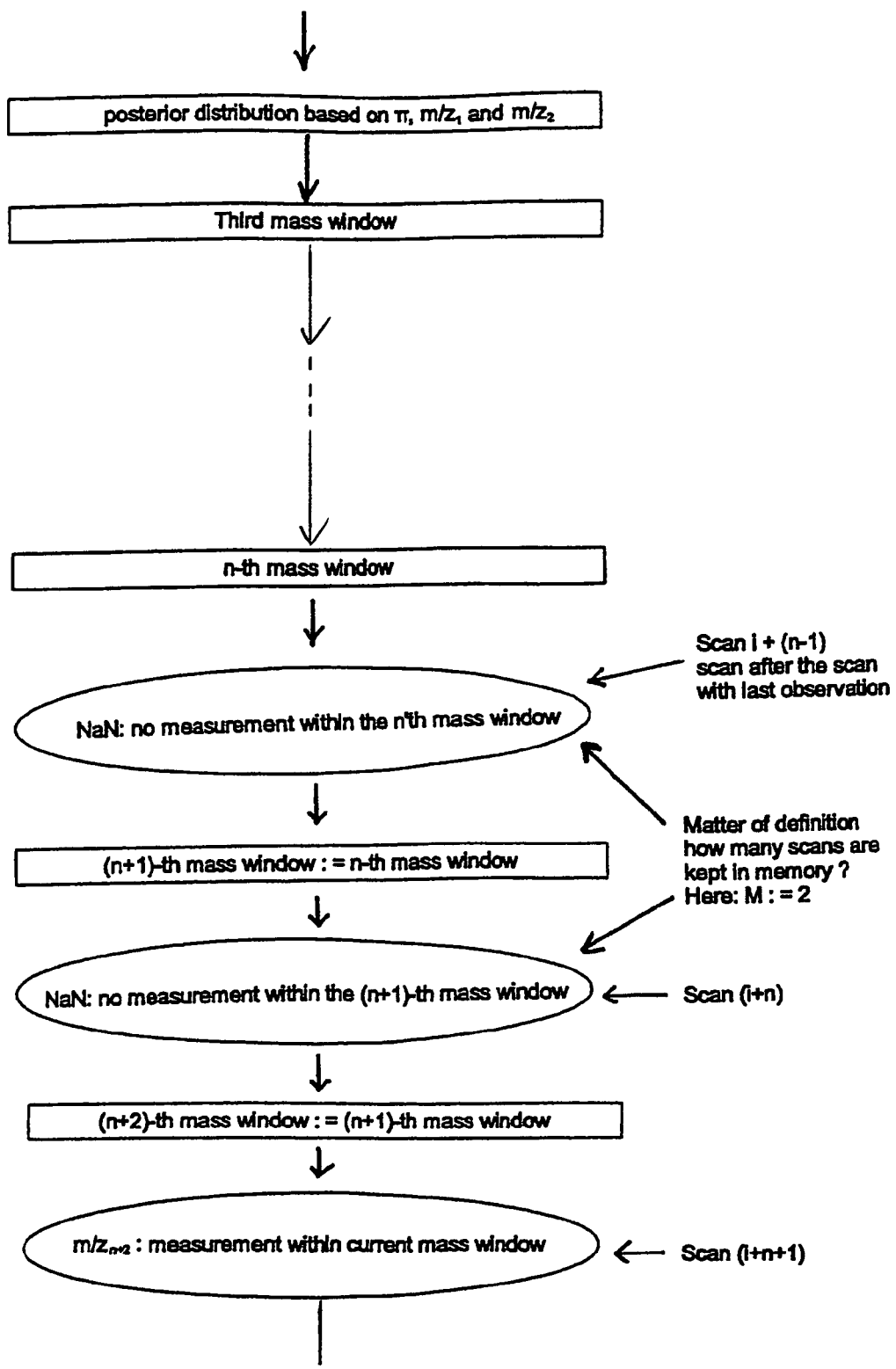

After abortion of the respective search the resulting retention times may be checked on the basis of the known values for the respective internal standard (FIG. 4c). For each peak certain relevant data may be outputted (FIG. 4d).

Figure 5:
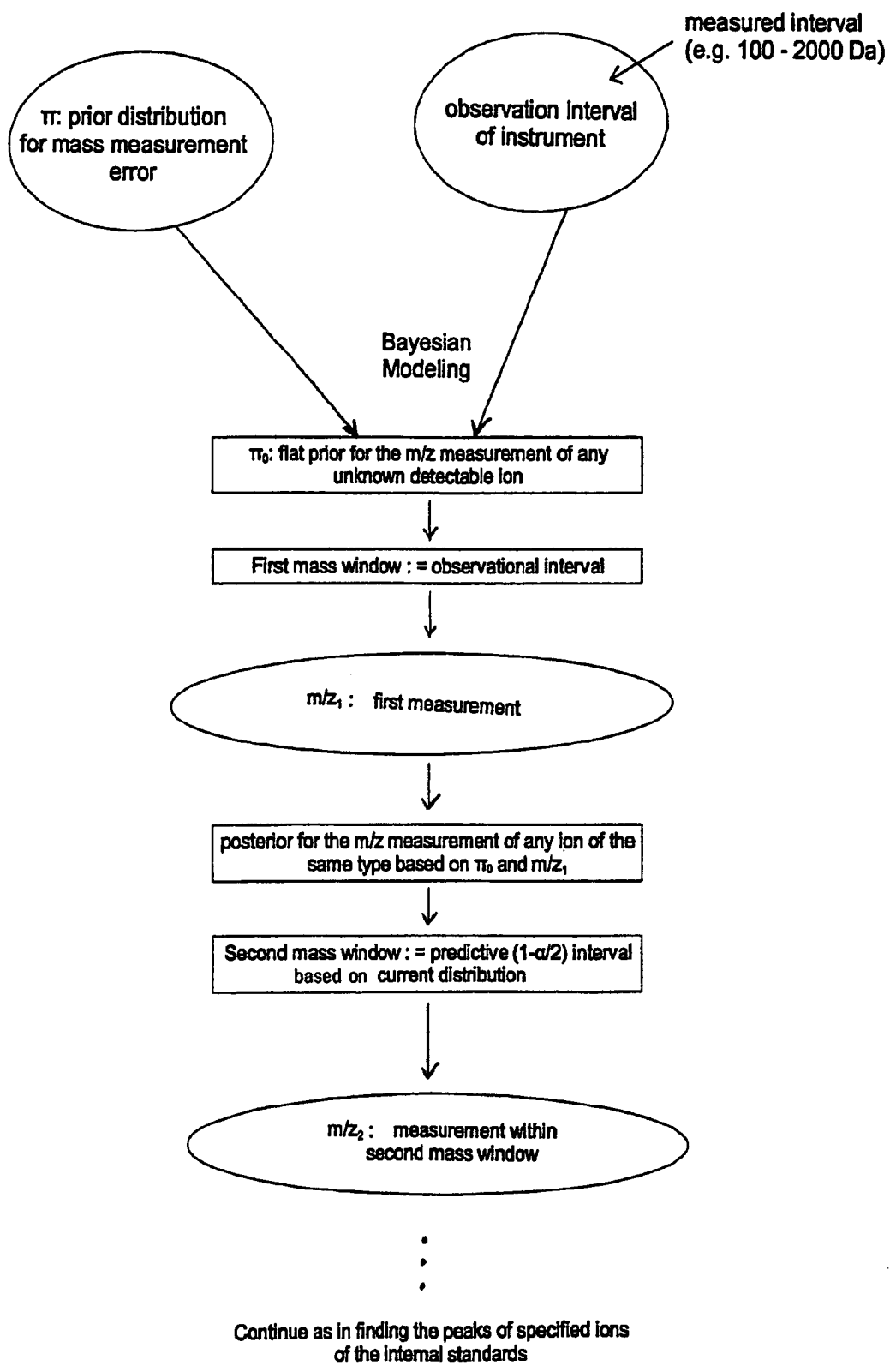
FIG. 5 shows a flow chart or data flow type diagram illustrating an embodiment of the grouping to find peaks of unknown ions of constituents of a sample.

A corresponding example with respect to finding peaks of unknown ions is given in FIG. 5. The proceeding is very similar to the case of FIGS. 4a to 4d. Instead of assuming a respective distribution (e.g. normal distribution) centered on the theoretical m/z value of a respective specified ion, now a even distribution over the whole measurement range of the used apparatus is taken as starting mass window.

After having detected the first data point, the posterior distribution and a narrowed current mass window are obtained on the basis of the probability calculus, and the algorithm proceeds basically as in the case of finding peaks of specified ions of internal standards with respect to the peak finding and the updating of the adaptive mass window. For the search for unknown ions, however, the application of additional conditions such as an intensity cutoff condition or intensity condition and at least one condition based on the typical shape of a chromatographic peak should be applied, in addition to the implicit requirement that measurements of ions of the same type have to be near to each other in terms of m/z value and scan time. In particular, it should be required that the sequence of the respective intensity values has a minimum cumulative intensity and shows the typical shape of a chromatographic peak. In the following, preferred implementations of these additional conditions are explained.

Application of Additional Criteria in the Course of the Grouping

First of all, if the second observation within some adaptive mass window has a smaller intensity than the first observation, the first is dropped and the search is continued with the second observation taking over the role of the first, since the first intensity value and the second intensity value cannot belong to the same peak in view of the unimodality condition.

Given that four data points have been observed in successive scan times with their m/z values $(m/z_1, m/z_2, m/z_3, m/z_4)$ within some adaptive mass windows, then it is checked, whether their cumulative intensity, taken with respect to a common baseline, is above some threshold. As long as it is not, the search within the adaptive mass windows is continued. If in successive scans the flow of additional data points into the adaptive mass windows is interrupted without their intensity values ever passing the intensity cutoff, the data points are discarded.

If the cumulative intensity of some successive data points within some adaptive mass windows passes the intensity cutoff, it is checked whether the sequence of intensity values shows some unimodal shape. If this is not violated too much, the search is continued. If it is violated, the first data point is dropped and thrown away, and the search is continued with the other data points being the new collective. If in the successive scan times, more data points enter that collective, and at some time with the new data point being introduced, the unimodality requirement is not fulfilled any more, the collective of data points without the latest one is considered a completed peak, and a new search is started with the latest data point as the first one.

Accordingly, successively with the finding of data points falling in a current mass window the unimodality condition and some sort of intensity condition, preferably also an additional kurtosis condition, is applied starting after four data points have been found which possibly belong to the same ion. These data points may be termed "candidate members" of a respective group of data points. If the additional conditions are not fulfilled, then all data points belonging to a respective ion have been found or there are no such data points in this m/z range. Afterwards, the algorithm is re-initialized for the search for other unknown ions. This means, that again an even distribution over the complete m/z axis or the complete m/z observation interval of a respective measurement system is assumed for starting the algorithm.

In the case, that a collection of peaks having to a certain extent overlapping mass-windows is found, the respective mass- and time-windows might be combined, to check, whether these peaks should be attributed to the mobile phase. If the combined time window extends over large part of the observation time, then one can generally assume that these data points are measurements of ions in the mobile phase. Accordingly, these data may be deleted by applying a corresponding deletion template.

Criteria Based on Collective Characteristics of the Data Points

The intensity condition, the unimodality condition and the kurtosis condition or detection are examples for additional conditions which are based on collective characteristics of a plurality of intensity values belonging to data points observed in successive scan times with their m/z values within the adaptive mass window. The latter two conditions may be applied as follows:

It is assumed that some potential peak is found with retention times $t_1, t_2, \ldots, t_N$, and intensities $I_1, I_2, \ldots, I_N$. The first retention time is the upper limit of some time-interval up to which $I_1$ ions within some mass-to-charge range were collected. Further, the lower limit of that interval is needed and it is defined to be $$t_0 := t_1 - \min\{t_{n+1} - t_n, n=1 \ldots, N\}$$

These are the data to which the unimodality condition and the kurtosis condition are applied.

A series of observed intensity values belonging to ions of the same component can be interpreted as some histogram of so-called "grouped" data. A certain statistical sense of the word "grouped" is assumed here. Accordingly, the unimodality condition and the kurtosis condition are applied to "grouped" data in this statistical sense.

That is, because actually the detection hardware counts all ions with same (discrete) mass-to-charge value that appear within a time-interval defined by the scan times.

Given the LC-process is some random process, molecules of the same substance appear with a probability according to some probability distribution around some mean retention or deletion time. This distribution is seen to be (almost) continuous in time, but the process can only be observed at discrete time points, namely the different scan times. Thus a histogram is observed where each bar, namely the intensities, gives the observed number of occurrences within some time-interval.

Grouped data compared to the unobservable "original" data sometimes requires adapted ways of analyzing.

Checking Unimodality

The check on unimodality is based on the so-called DIP-Test of Hartigan and Hartigan (1985), cf. P. M. Hartigan: "Computation of the Dip Statistic to Test for Unimodality"; Applied Statistics (1985) 34, 320-325, and J. A. Hartigan and P. M. Hartigan: "The Dip Test of Unimodality"; Annals of Statistics (1985) 13, 70-84.

Further, it is referred to Gabler and Borg: Unimodalität und Unimodalitätstests, ZUMA-Nachrichten (1996) 38, 33-44.

1) The peak intensities are normalized to add up to one $$f_{emp}(t_n) := \frac{I_n}{\sum_{k=1}^{N} I_k},$$

and the cumulative sums are calculated:

$$F_{emp}(t_n) := \frac{\sum_{k=1}^{n} I_k}{\sum_{k=1}^{N} I_k}.$$

The resulting function $F_{emp}$ has the properties of some empirical distribution function.

Figures 4, 6:
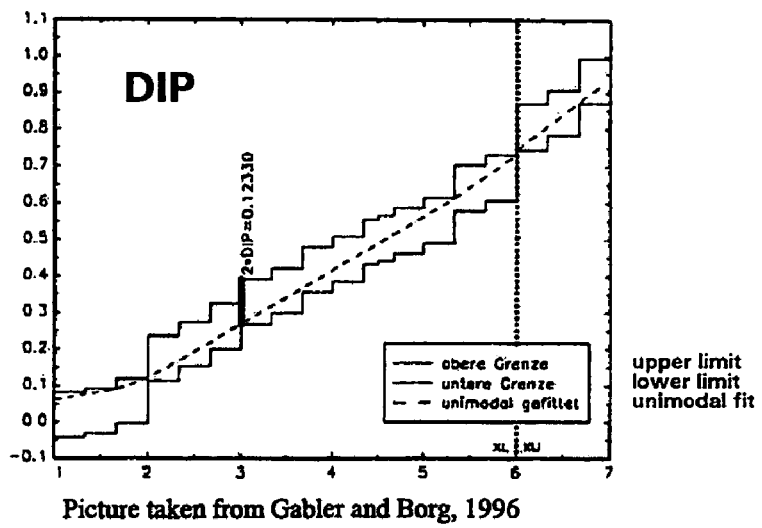
FIG. 6 is a diagram illustrating the so-called "DIP" measure used in an unimodality condition (diagram taken from Gabler and Borg, 1996).

2) The nearest unimodal distribution function to this distribution function is found using greatest convex minorants and least concave majorants:

A unimodal distribution function with mode m is convex in $(\infty, m]$ and concave in $[m, \infty)$. The nearest unimodal distribution function U to the empirical distribution $F_{emp}$ is given by the greatest convex minorant of $F_{emp}$ in the interval $[t_1, t_L]$ and the least concave majorant in the interval $[t_U, t_N]$, where $t_L$ and $t_U$ are iteratively determined to minimize the (point wise) distance between $F_{emp}$ and U. (U is continuous—see FIG. 6). This distance is called "DIP".

3) Then the differences $$u(t_n) := U(t_{n+1}) - U(t_n), n=0, \ldots, N,$$

are built and some approximate empirical density function u according to U with the same granity as $f_{emp}$ is obtained.

4) The difference used as measure of unimodaltiy is defined to be the maximum point wise difference between u and $f_{emp}$.

Alternatively, also the maximum point wise difference between U and $F_{emp}$ could be used, the classical DIP-measure. However, the results obtained so far did not look as good. The reason is presumably that the data are grouped data, whereas the DIP-statistic was developed for original data.

5) If this difference is larger than some threshold (typically some value between 0.01 and 0.1) the collective of data points is considered not to be caused by ions of the same type.

Since the uniform distribution belongs to the class of unimodal distributions, histograms with almost rectangular shape will not be filtered by the non-unimodality threshold. This is done by checking the kurtosis of the fitted unimodal density.

Checking Kurtosis

In writing the formula to calculate the kurtosis, the mean retention time is denoted as $$\bar{t} := \sum_{n=1}^{N} t_N.$$

Additionally, also the mean of each of the corresponding retention or detection time intervals denoted as $\bar{t}_n := \frac{1}{2}(t_n - t_{n-1}), n = 1 \ldots N$ is needed.

The kurtosis of the fitted unimodal density is calculated by:

$$k = \frac{\frac{1}{N} \sum_{n=1}^{N} (\bar{t}_n - \bar{t})^4 u_n}{\left( \frac{1}{N} \sum_{n=1}^{N} (\bar{t}_n - \bar{t})^2 u_n \right)^2}.$$

The kurtosis (as used here) is defined to be the fourth central moment divided by the second central moment to the power of two. The kurtosis of any normal distribution, not only the standard normal distribution, is 3. The kurtosis of the uniform distribution (also called rectangular distribution) defined on any interval is 1.8. Thus to filter out almost rectangular shaped histograms, the kurtosis threshold is preferably set at a level of about 2 to 2.5, which has to be exceeded.

In general, the r-th moment of some random variable is defined to be the expected value of the r-th power of the random variable. The r-th central moment of some random variable is defined to be the expected value of the r-th power of the difference of the random variable to its first moment.

The location of the density of some distribution is determined by the first moment, the shape by the following higher-order central moments. The more moments are equal, the more alike distributions are.

Illustrative Examples

In the following some illustrative examples for the Bayesian update scheme and the grouping obtained on the basis thereof are given.

Figure 7:
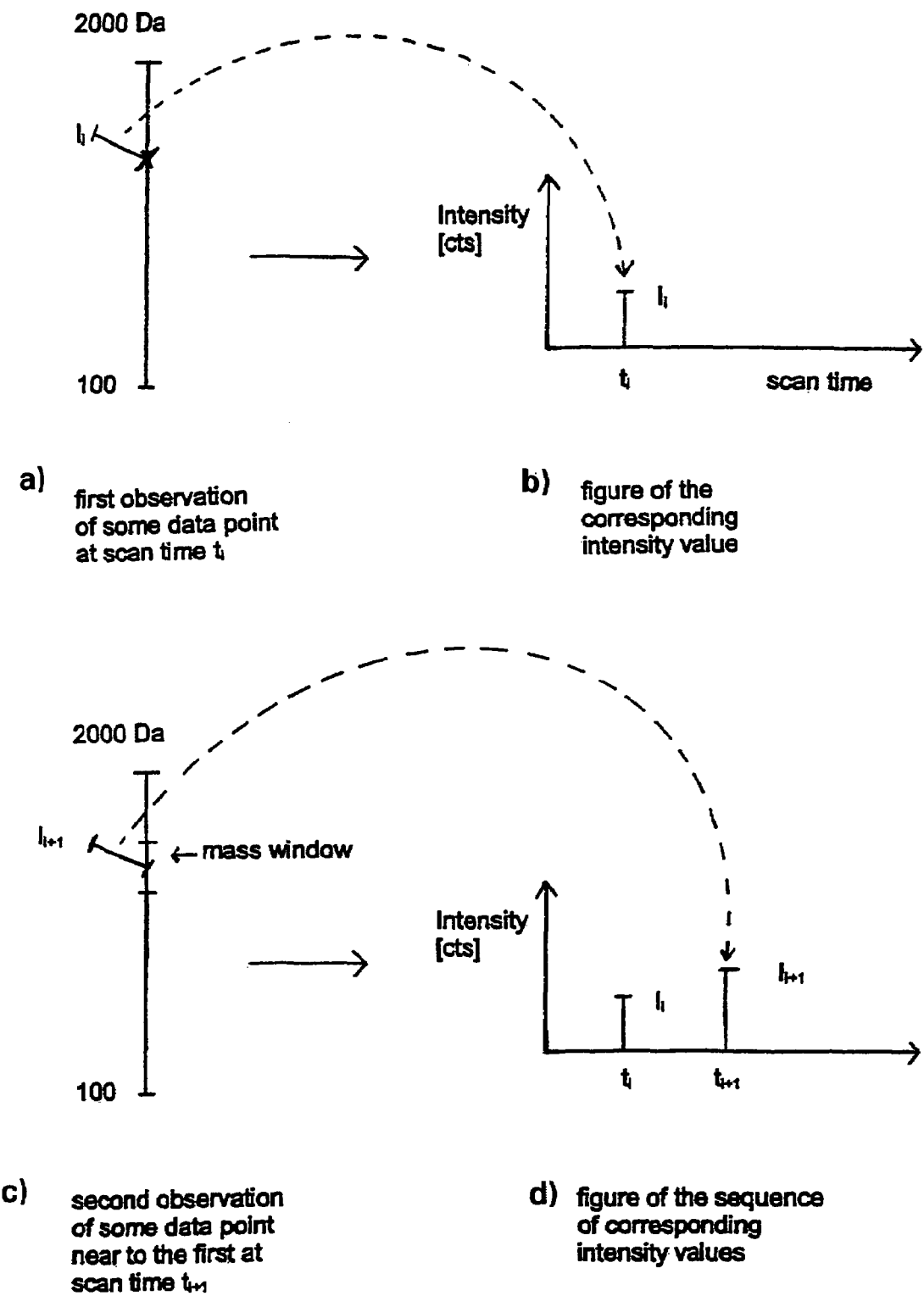
FIG. 7 with schematically representations in FIG. parts 7a to 7g illustrates an example for finding some peak by grouping based on Bayesian learning.

Finding a peak for some unknown ion first an even distribution of measurement error over the whole m/z range is assumed, as shown symbolically in FIG. 7a. First observation of a data point gives an intensity value (FIG. 7b). On the basis of the Bayesian probability calculus a narrowed mass window is obtained (FIG. 7c). A further data point falling in this mass window (FIG. 7c) is identified as a candidate data point belonging to the same product or constituent of the sample having a certain intensity (FIG. 7d). This scheme is repeated (compare FIGS. 7e and 7f) and may lead to a sequence of intensity values (FIG. 7g) which presumably are caused by the same ions. The intensity values according to FIG. 7g passed the intensity check, the unimodality check and the kurtosis check.

Figure 8:
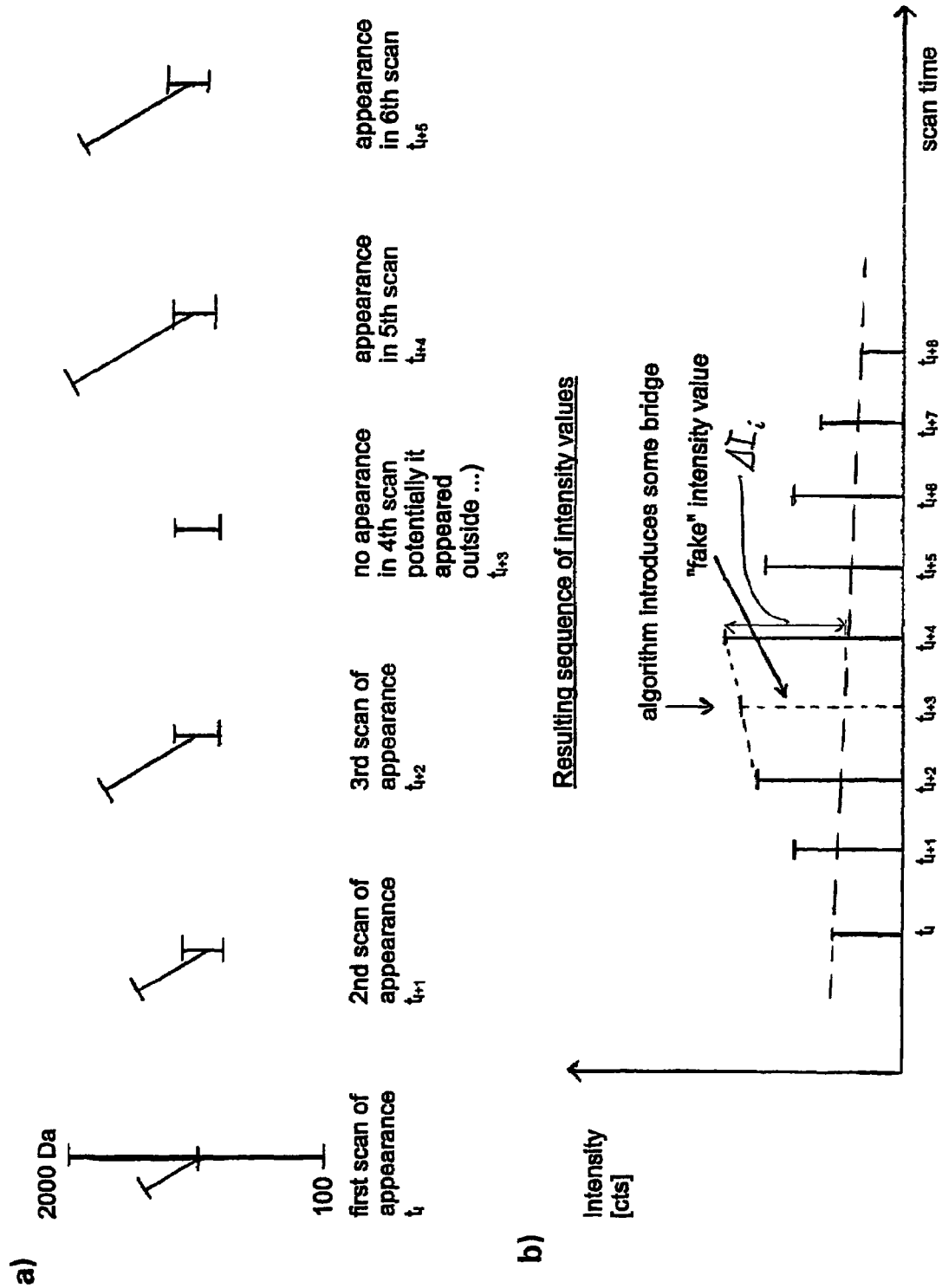
FIG. 8 with schematically representations in FIG. parts 8a and 8b is an illustrative example for the handling of one missing observation on the m/z axis in the course of the grouping.

In the grouping it may be accounted for that not in each scan a data point is found which falls in the current mass window. As illustrated in FIG. 8a and FIG. 8b, a corresponding missing intensity value may be added, for example by linear interpolation in a sequence of intensity values, to which the intensity condition, the unimodality condition and the kurtosis condition is applied. If one or a defined number of subsequent intensity values are missing, then the grouping is not aborted, since missing data points may be caused by circumstances of the applied techniques and cannot detect it although they should be present. By interpolation the missing point or points the cumulative intensity detected is not negatively affected and the unimodality test and the kurtosis test can still validly be applied.

Preferably, the intensity condition is not applied directly to the plurality of intensity values belonging to the data points of a respective group presumably forming a peak but instead to the intensity differences $\Delta I_i$ between the respective intensity value and the corresponding intensity of a straight baseline intersecting the first and last intensity value of this group. In FIG. 8b such a baseline is drawn though the intensity value from time point $t_i$ and the intensity value for the time point $t_{i+8}$. Accordingly, the first and the last intensity value of such a group of intensity values do not contribute to a cumulative intensity value checked in the intensity condition.

Figure 9:
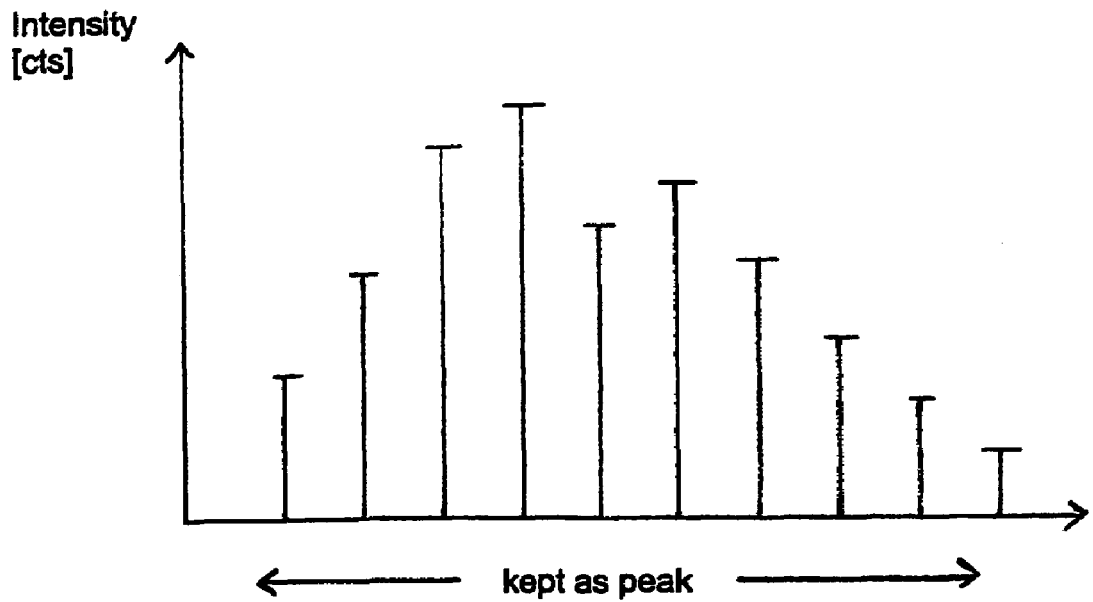
FIG. 9 is an illustrative example for measurement data identified as peak although there is a minor violation of the unimodality condition.

Preferably, the unimodality condition is applied such, that a minor violation of the unimodality requirement is admissible (FIG. 9).

Figure 10:
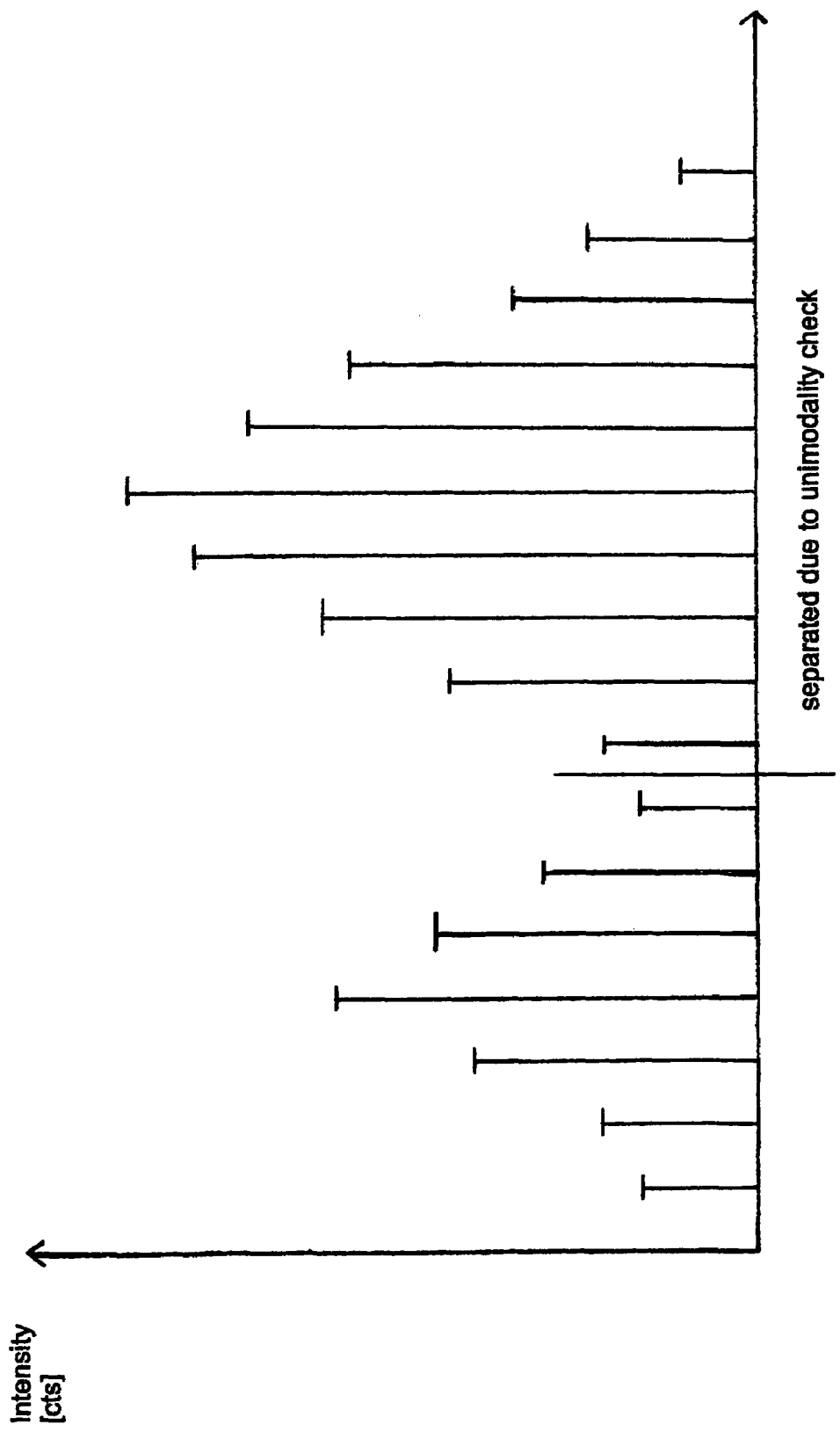
FIG. 10 is an illustrative example showing overlapping peaks which can be separated in the course of the grouping on the basis of the unimodality condition.
Figure 11:
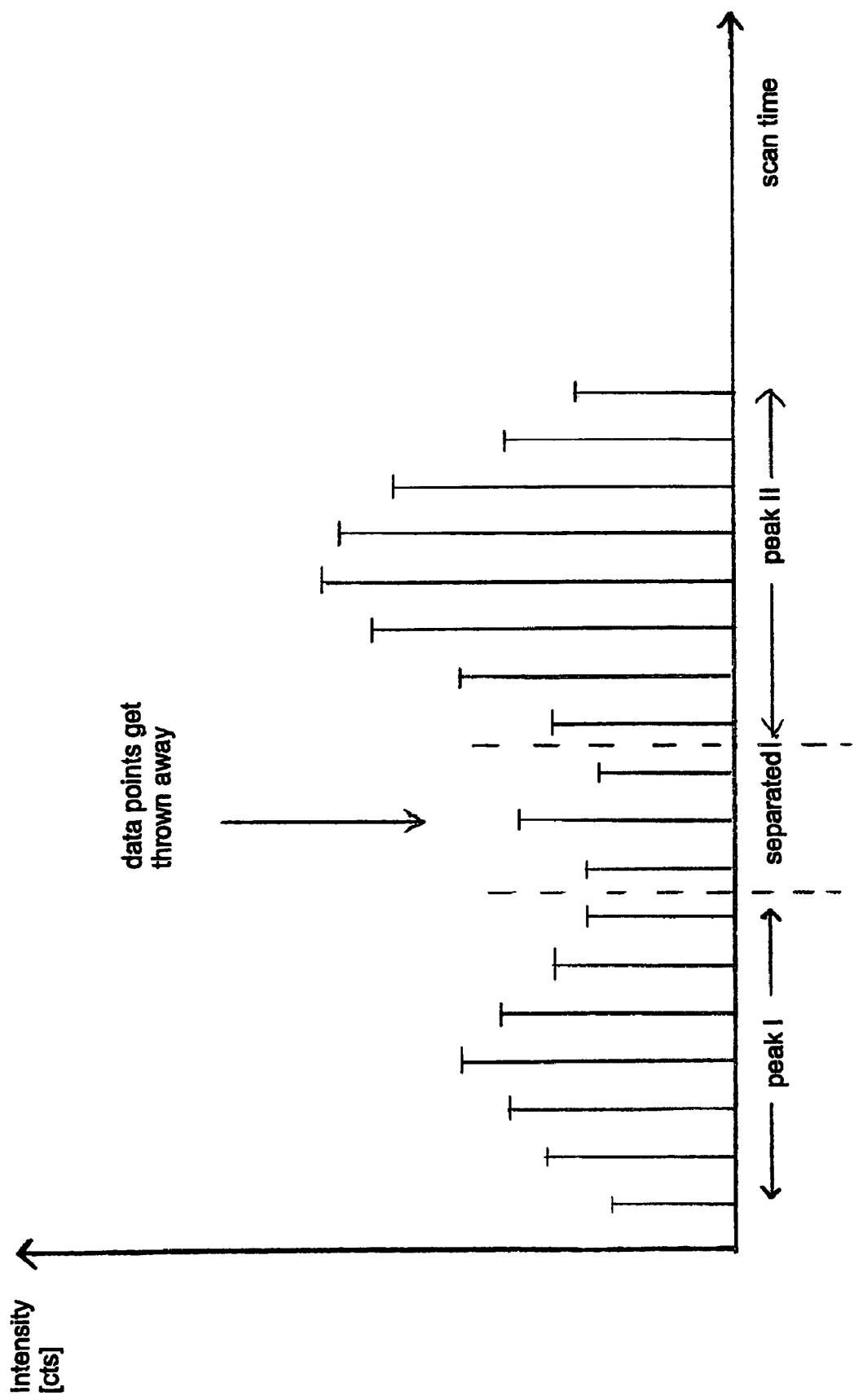
FIG. 11 is a further illustrative example concerning overlapping peaks, which can be separated on the basis of the unimodality condition although the peaks are highly overlapping, with unclear interplay.

The unimodality check has proved to be a powerful means for separating overlapping peaks (FIG. 10), even if there is unclear interplay between the two groups of data points associated to one respective of the two overlapping peaks (FIG. 11).

Due to the power of the unimodality condition alone or in combination with other conditions, in particular the kurtosis condition, it might be sufficient for some measurement situations, that no Bayesian learning is applied and that only a peak search algorithm is applied to fixed m/z traces in the sense of a so-called "hard binning", to identify respective peaks, with this peak search algorithm being based on the intensity condition and unimodality condition and possibly at least one additional condition, e.g. kurtosis condition.

Figure 12:
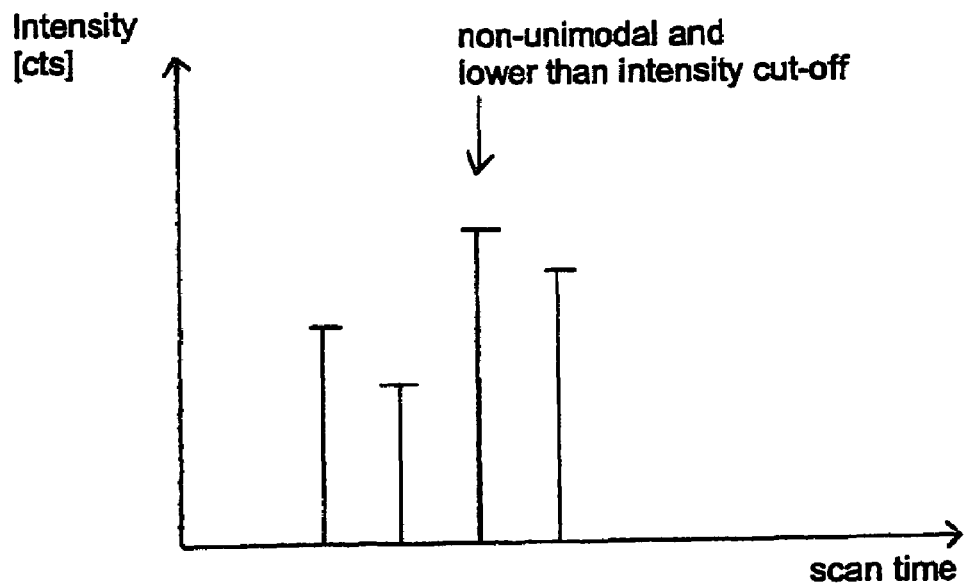
FIG. 12 is an illustrative example for a spike in the measurement data.

Preferably, the intensity condition, unimodality condition and preferably also the kurtosis condition are only applied to groups of data formed by at least four data points, on the basis of the assumption, that any real peak must have at least four data points. Accordingly, spikes having less points than four will in any case not be considered to be a real peak, so that these points are discarded even before the intensity condition, the unimodality condition and other conditions are applied. Spikes having four or more points (FIG. 12) generally do not pass the intensity condition or/and the unimodality condition. Spikes, which would pass those conditions may be handled as real peaks, if not other conditions based on distributional conditions, such as the kurtosis condition, are applied. In practice it is generally not necessary to sort out spikes which passed the intensity condition and the unimodality condition, since normally the analysis is based on ensembles of many measurements. It is very unlikely, that spikes occur at the same position in several measurements.

Figure 13:
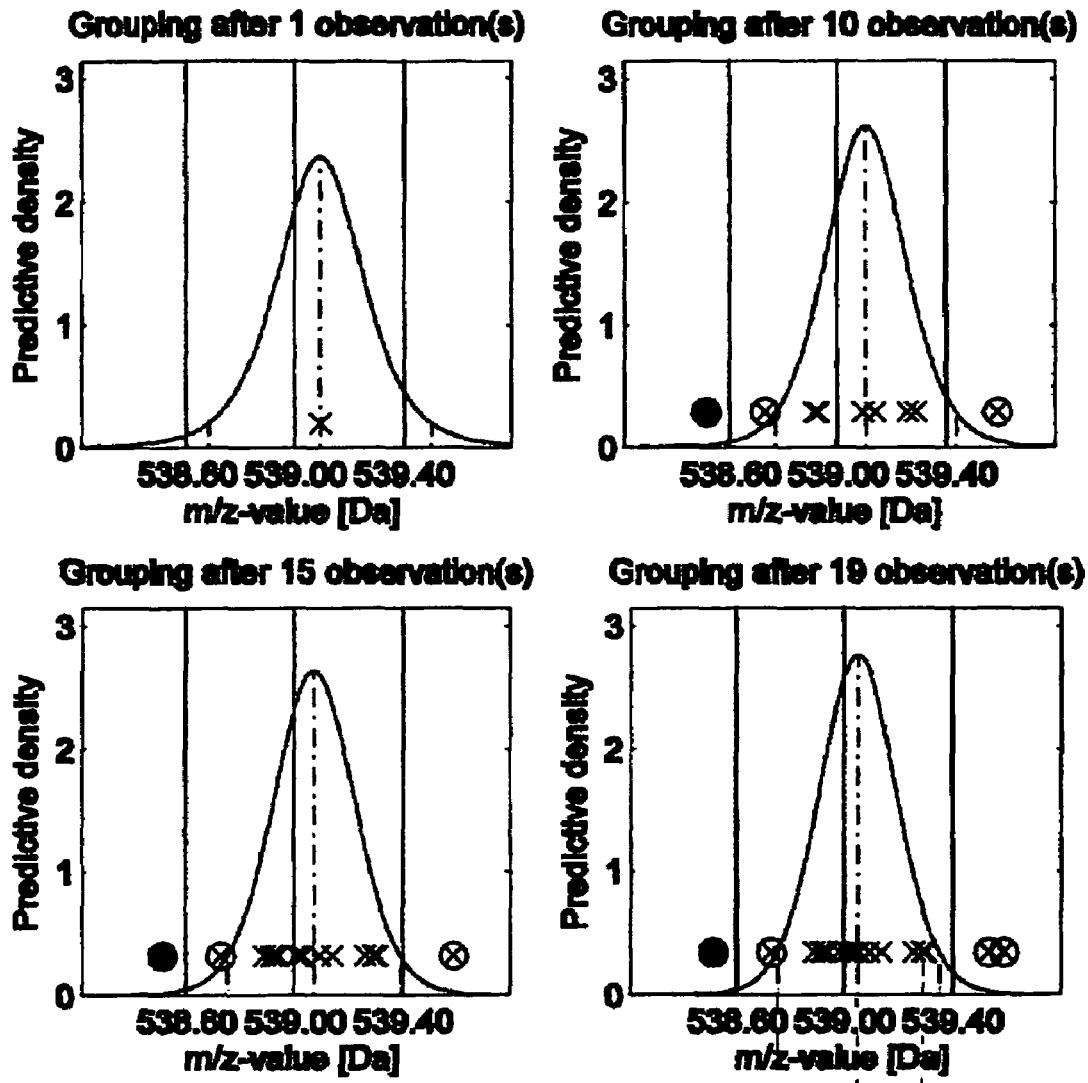
FIG. 13 is a schematically representation of the grouping process along the m/z axis on the basis of a distribution of deviations $\Delta m/z_i$ of respective data points from a mean or characteristic value $m/z_{ION}$.

The grouping process is also illustrated in the diagram according to FIG. 13, which refers to the grouping with respect to unknown ions. After the first data point has been found, a measurement error distribution for the m/z value is obtained, which is centered on the data point. Further, the data points falling in a respective current mass window defined by the respective current distribution are identified as candidate members of the same group associated to respective same ions. Preferably, only the information "data point falls in the current mass window" and "data point falls not in the current mass window" is taken into account for the Bayesian updating, but not also the intensity of the respective data point. However, this is possible in principle. According to the approach assumed here, when intensity is not taken into account, the distribution of the different data points occurring in direction of the t-axis or scan number axis is evaluated such for obtaining the current posterior distribution (which is the prior distribution for the next data point), that the average m/z value obtained for all members (candidate or confirmed members) of a respective group corresponds to the maximum of the resulting distribution.

Figure 14:
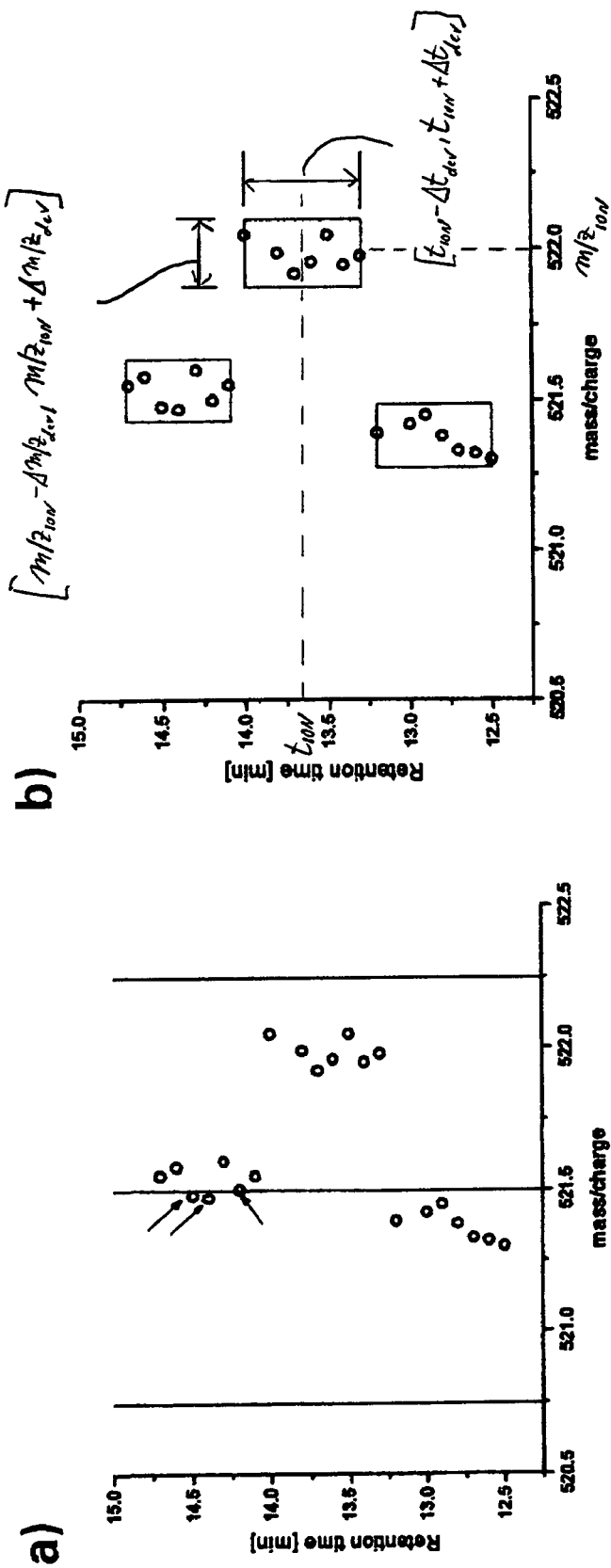
FIG. 14 shows two diagrams for comparison of a grouping on the basis of the "hard binning" method (FIG. 14a) and the grouping on the basis of variable bins (FIG. 14b) in accordance with the grouping process as illustrated in FIG. 13.

The use of "variable bins" along the mass-to-charge axis, which are obtained from Bayesian learning, has an advantage that a wrong grouping of data points, i.e. wrong determinations that certain data points belong to another, wrong ion, can be avoided. This is the danger in conventional peak picking methods which are based on "hard" bins along the m/z axis. FIG. 14 compares illustratively the hard binning method (FIG. 14a) with the grouping on the basis of variable bins obtained from Bayesian learning (FIG. 14b). A respective variable bin is characterized by the average m/z value $m/z_{ION}$ for all observations which fell in the respective current (adaptive) variable bin and the width $2* \Delta m/z_{dev}$ of the respective variable bin which is centered on $m/z_{ION}$. In FIG. 14a those data points, which would be grouped wrong in the case of the "hard binning" method, are identified by arrows.

A data processing and grouping in accordance with the schemes presented in the foregoing is further illustrated in FIGS. 15 to 23.

FIG. 15 shows a section of raw data before any processing. Data points attributed to noise can be eliminated, e.g. on the basis of a histogram of logarithmized intensity values as explained on the basis of FIG. 1. Such noise data points are identified in FIG. 16 as full dots. FIG. 17 shows the data points having intensity values above the noise level. The noise data points have been eliminated.

By applying the algorithm selectively to mass windows in which internal standard ions are expected, the data points marked as fall points in FIG. 18 are identified as being caused by one of the specific ions of the internals standards. On the basis of these points and other data the mass error distribution is checked and learned.

By applying the algorithm to the remaining points all candidate data points of a real chromatographic peak as well as other data points are identified. In FIG. 19 data points not fulfilling the criterion of a chromatographic peak are shown as full points. Accordingly the algorithm decides, that these data points are not caused by some substance that went trough the LC-MS process properly. FIG. 20 shows the sequence of the intensity values of the data points between 457 and 457.5 Da in FIG. 19. Because there is no sub-sequence with a clear peak shape and of some (cumulative) considerable intensity, all these data points are discarded.

FIG. 21 shows those data points as full dots, which fulfill the criterion of a chromatographic peak. FIG. 22 shows the sequence of the intensity values of these data points, which clearly follow a unimodal shape.

Instead of maintaining these data points, a cumulative intensity and the rectangle of the mass- and time-window may be kept as the main information about the detected ion (FIG. 23).

System

Figure 24:
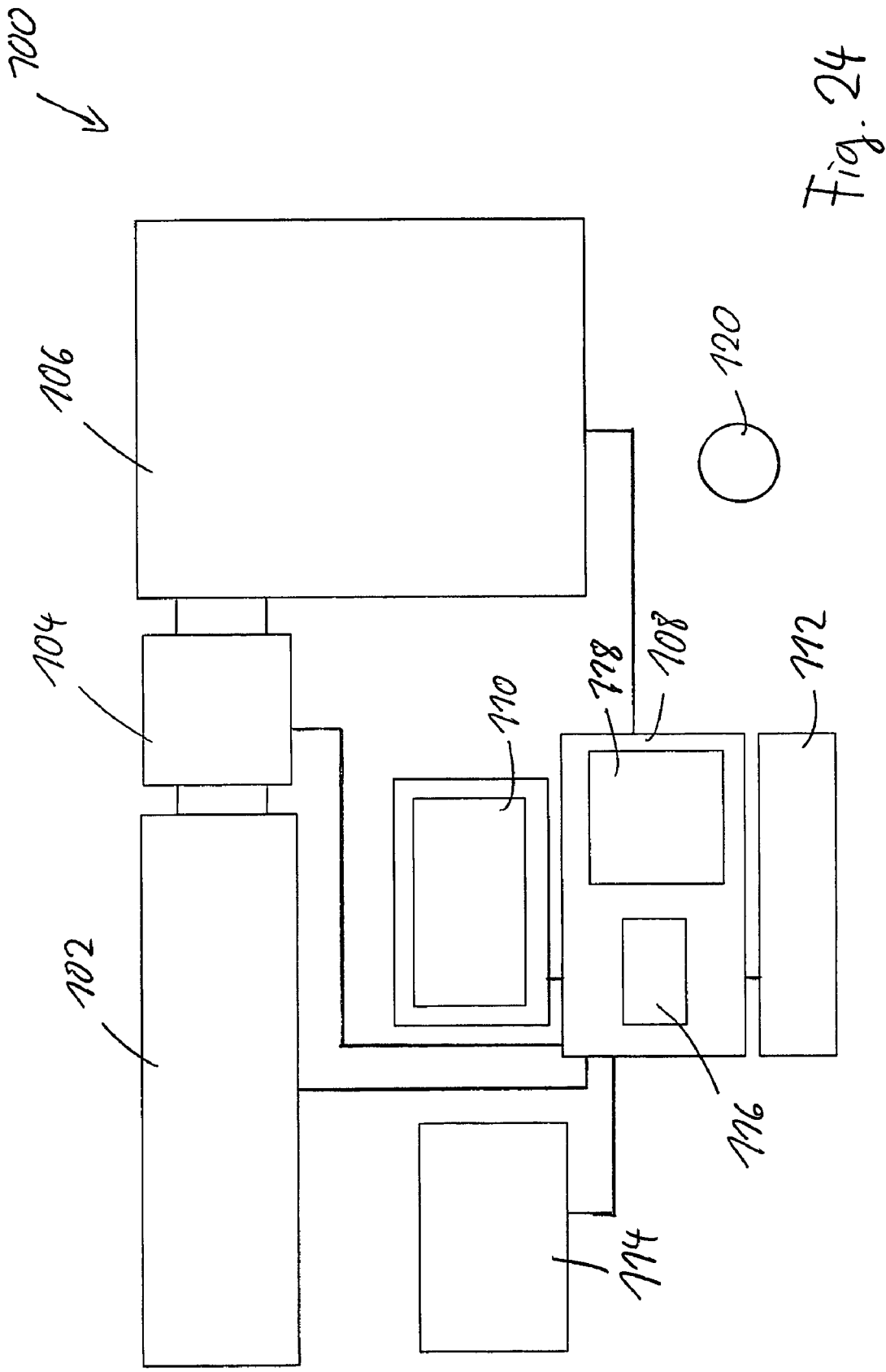
FIG. 24 is a schematically block diagram of an embodiment of a system according to the invention.

FIG. 24 shows schematically an example for the structure of a system, which may be used for implementing an embodiment in one or in both of its aspects. The system or analyzing apparatus 100 has a separating unit 102, e.g. a capillary electrophoresis unit or liquid chromatography unit, an ionization unit 104, e.g. an electrospray ionization unit, and a mass analyzing unit 106 (e.g. time of flight mass spectrometer, quadruple mass spectrometer or the like). The separating unit 102 separates constituents of a respective sample and provides the separated constituents according to a time series to the ionization unit 104, in which constituents are ionized and provided to the mass spectrometer 106, which has appropriate ion separation and detection hardware to provide a time series or scan number series of data which amount to three-dimensional data including a detection time or scan number, a mass-to-charge value of a respective ion or respective ions and an intensity or count number for the respective ion or ions.

The units are controlled by a control unit 108 having a display 110, a keyboard 112 and a printer 114. Integrated in the control unit are at least one processor 116 and a data storage unit 118. The storage unit 118 may store a data base of characteristic data of constituents of interest for comparison with measurement results achieved with this system 100.

The control unit 108 receives the measurement data from the mass spectrometer 106, and groups these data in accordance with an embodiment. For effecting this grouping, the raw data received from the mass spectrometer 106 are stored in the storage unit 118. Preferably, data structures are used which reflect the association with each other of a respective time or scan number value, a respective mass-to-charge value and a respective intensity or count number value. From the grouping intervals of the time or scan number coordinate and of the mass-to-charge coordinate are obtained, together with a respective cumulative intensity or count value, which represent a respective peak associated to a respective constituent of the sample. These resulting data include basically all interesting information which can be derived from the raw data. All further analysis basically can be effected on the basis of the resulting grouping data instead of the raw data. Accordingly, the raw data may be deleted after generation of the grouping data. Even if the further analysis is effected on the basis of the raw data, the grouping data are very helpful since the grouping data allow an identification of data points which are of particular interest.

It should be noted, that the data preprocessing and data processing may also be effected by a data processing system, e.g. general purpose computer, which is not directly linked to a measurement system e.g. including units 102, 104 and 106.

With respect to the system 100 according to FIG. 24 it should be added, that such a system may be provided on the basis of any conventional system having a control unit adapted for effecting data processing by loading appropriate software. The software may be provided in the form of a computer readable medium carrying a program of instructions, e.g. in the form of a CD-ROM or DVD-ROM or by loading such software from a server computer system, e.g. via internet.

Example

The data preprocessing and data processing in its various aspects was applied to an LC-ESI-MS set of data of a serum sample. By denoising, spike identification, deleting the sequence of the mobile phase and the internal standards and grouping the peaks into variable bins a new set of data was generated which keeps the complete relevant information about position and intensity of the "real" peaks while considerably reducing the amount of data. The raw data included about three million single data points, corresponding to an amount of data of about 22 MB. After the preprocessing and processing 1087 peaks remained, corresponding to an amount of data of about 700 kB. Accordingly, a considerable data reduction and compression was obtained, although all information was maintained which is needed for characterizing the sample with respect to constituents included therein.

Figure 25:
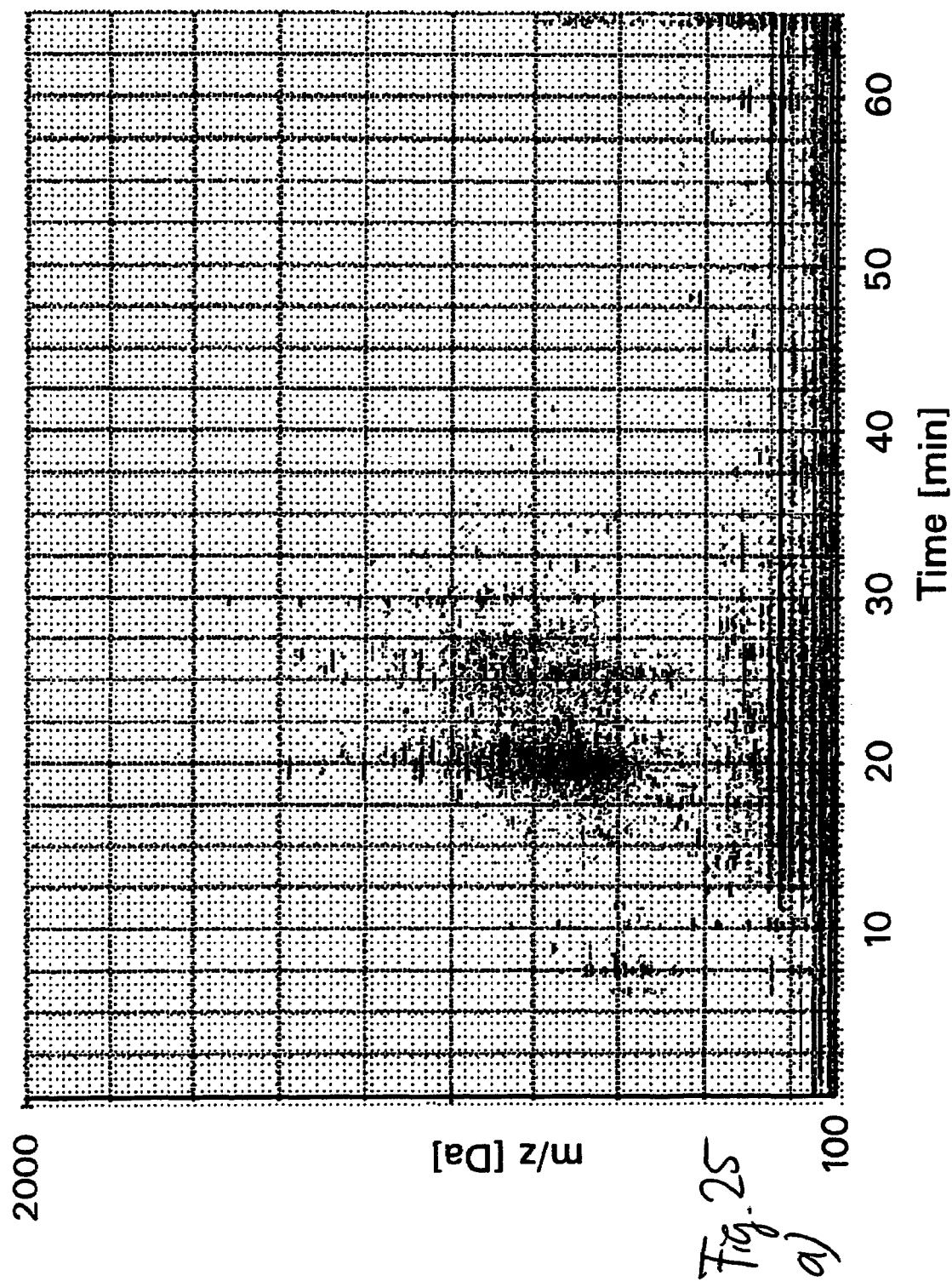
FIG. 25 shows two diagrams allowing a comparison of a raw LC-MS data set before the data preprocessing and processing according to the invention (FIG. 25a) and a data set obtained from the data preprocessing and processing according to the invention (FIG. 25b).

FIG. 25 is a comparison of a three-dimensional representation of a LC-MS data set before (FIG. 25a; raw data) and after (FIG. 25b; grouped data) the data preprocessing and processing. The relevant information is maintained while the data amount is reduced by a factor of about 100.

Numerical Example

Figure 26:
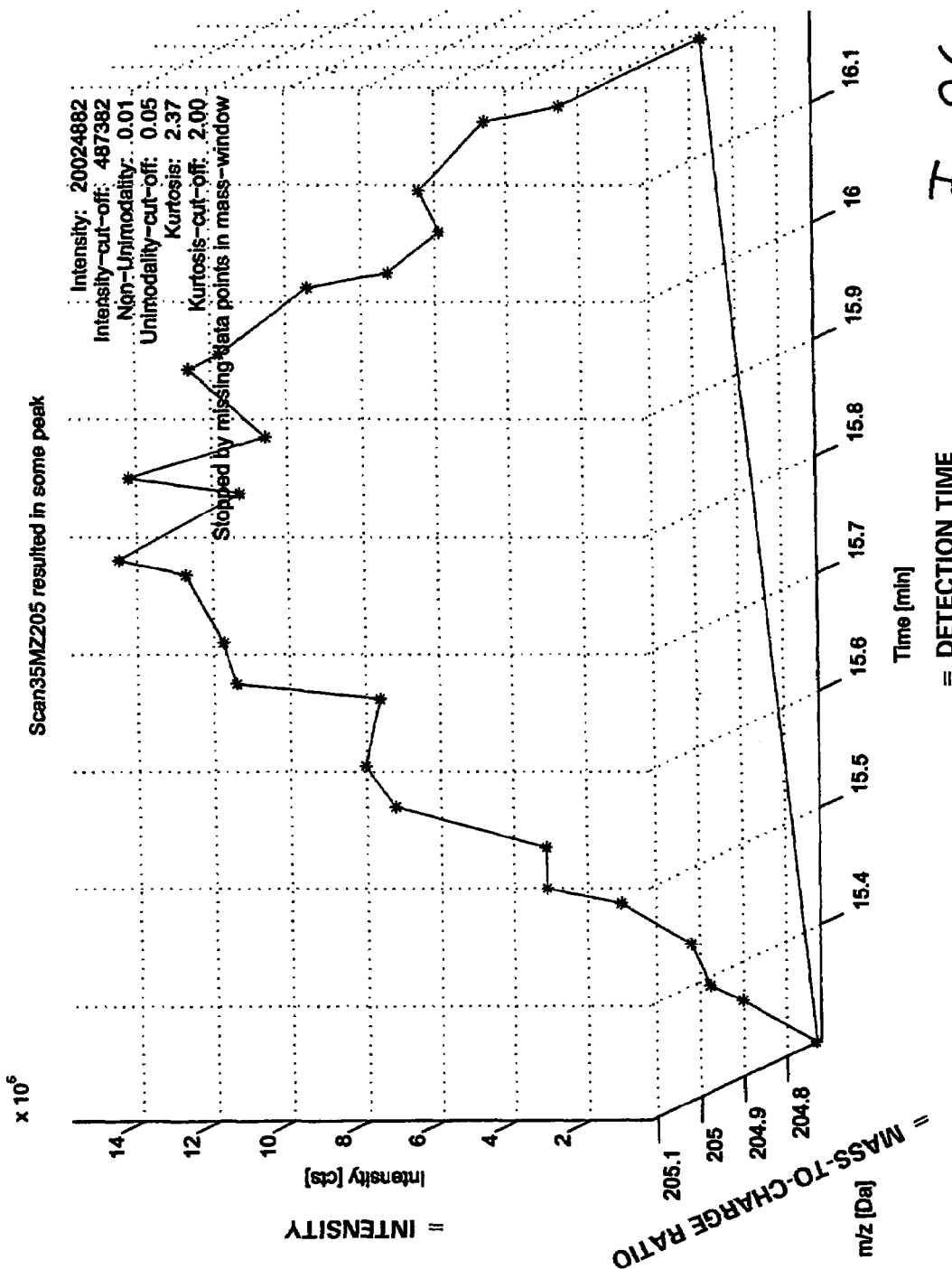
FIG. 26 is a graphical representation of a three-dimensional diagram showing data points identified to belong to a peak by means of a grouping based on Bayesian learning.
Figure 27:
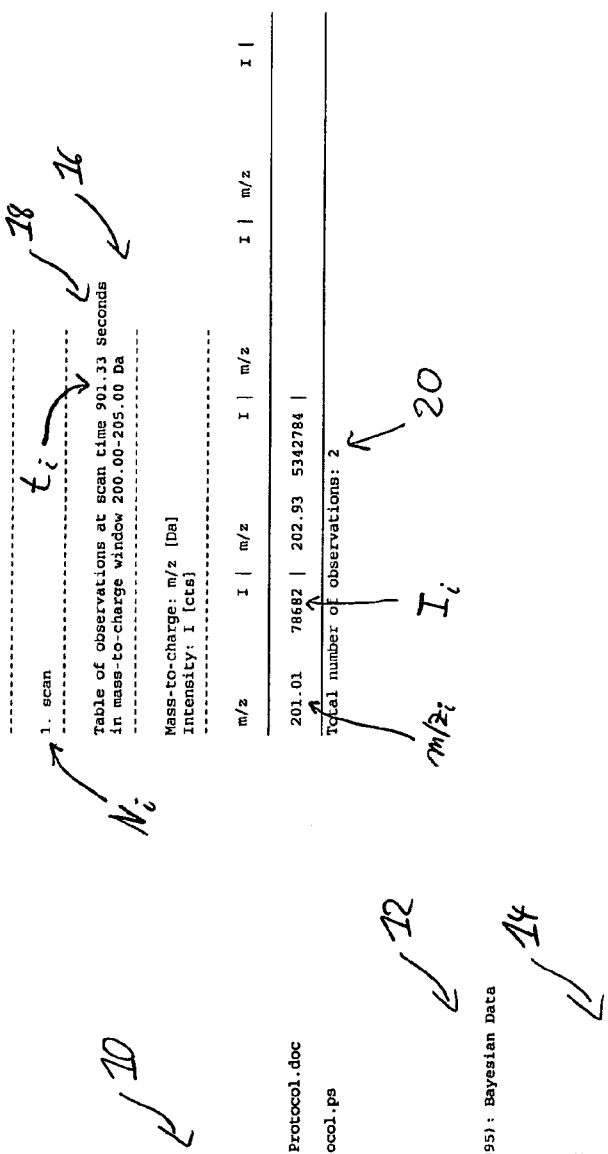
Figure 58:

With reference to FIG. 26, which shows a diagram representing a peak found by grouping in a large LC-MS raw data set and with reference to a grouping protocol shown in FIGS. 27 to 78, in which protocol data representing the grouping underlying the grouping result according to FIG. 26 are included, a preferred embodiment of the grouping is further illustrated. FIGS. 27 to 78 represent an excerpt from the grouping protocol having many grouping protocol pages.

In an introductory portion 10 of the grouping protocol, on grouping protocol page 1 of FIG. 27, some parameters are given, on which the grouping is based. Important parameters are an intensity cutoff threshold, an unimodality cutoff threshold and a kurtosis cutoff threshold. In sections 12 and 14 of the protocol the type of prior distribution assumed and initialization data for the Bayesian statistics are given.

For reasons of simpler data processing, not the whole mass-to-charge axis is considered at once when scanning the raw data for data points which fall in the current mass-to-charge window, but only a certain working mass-to-charge window, in the present portion of the grouping protocol a working mass-to-charge window of 200.00 bis 205.00 Da (see remark at 16). The other mass-to-charge ranges up to 2000.00 Da are scanned separately in respective working mass-to-charge windows (preferably overlapping) having each a width of 5.00 Da.

The grouping algorithm is initialized to a current mass-to-charge window corresponding to the working mass-to-charge window, i.e. the window 200.00 to 205.00 Da. An even distribution over this current window is assumed as prior distribution.

The first scan through the data, which corresponds to one scan of the mass spectrometer at a scan time 901.33 seconds (see at 18), results in two observations (see at 20), i.e. two data points are found, the first having a mass-to-charge ratio of 201.01 Da and an intensity of 78682 cts, the other having a mass-to-charge ratio of 202.93 Da and an intensity of 5342784 cts.

Grouping protocol page 3 of FIG. 28 summarizes the result of the grouping so far. Two potential peaks are found which are identified by a name giving its current position: Scan number of the last data point added as candidate member to a respective group of data points forming a peak and rounded average m/z value. In the present case, after the first scan, there are two groups each including one candidate member or two peaks formed each by one candidate data point, namely the group or peak denoted as Scan1MZ201 and the group or peak Scan1MZ203 shown at 22 and 24. From the statistics calculus a posterior distribution, which is the prior distribution for the next scan, and a predictive 95% mass window resulting therefrom are obtained as shown at 23 and 25 for the two groups. As distribution a t-distribution is taken.

The second scan shown on grouping protocol page 4 of FIG. 28 produced four observations. Two of the data points found fell in the predictive mass-window according to grouping protocol page 3, namely the data point (200.75, 13554) in the predictive mass window [200.72, 201.30] associated to peak Scan1MZ201 and the data point (202.93, 3867132) in the predictive mass window [202.65, 203.22] of peak Scan1MZ203. Since the intensity value of the respective data point found in the second scan fell short of the intensity value of the respective data point found in the first scan, the respective data point of the first scan is deleted from the group or peak now denoted as Scan2MZ201 and from the group or peak now denoted as Scan2MZ203 and the posterior distribution after the second scan, which is the prior distribution for the third scan is newly initialized on the basis of the respective data point found in the second scan. The grouping protocol includes corresponding remarks on page 5, at 26.

The other two data points (200.24, 47617) and (201.27, 18193) found in the second scan produce two further potential peaks or groups, namely the peak or group Scan2MZ200 and Scan2MZ201.

The third scan found two additional data points, of which the data point (201.01, 31529) fell in the predictive mass window of group Scan2MZ201, so that this data point is added to this group, now being denoted as Scan3MZ201. The other data point (203.06, 2587450) gives rise to an additional potential peak or group denoted as Scan3MZ203.

It should be added, that the data points which in this explanation are identified only by their mass-to-charge value and their intensity value are indeed three-dimensional data points, namely data points including also the respective scan time which represents the retention time in the chromatography unit. Accordingly, if it is referred herein to the data point (201.01, 31529) found in the third scan, this is only an abbreviation for the three-dimensional data point or data tuple (905.53 [seconds], 201.01 [m/z], 31529 [I]). The measurement quantity, to which the respective measurement value refers, is additionally given in cornered brackets. Instead the scan time $t_i$ also the scan number $N_i$ could be used and included in the three-dimensional data point or data tuple.

The additional data point added to group Scan2MZ201, now denoted as Scan3MZ201 results in an updating of the predictive t-distribution and the predictive mass window, as shown at 30 in grouping protocol page 7 of FIG. 30. In response to the fourth scan a further candidate member is added to group Scan3MZ201, now denoted as Scan4MZ201 (see grouping protocol page 9 of FIG. 31).

It should be added that potential peaks or groups are not deleted, if in one scan no additional candidate member is found. If in one scan no additional candidate member of a group is found and in the next scan again a member is found, then the missing member is added by linear interpolation between the neighboring candidate members. If, however, in two subsequent scans no additional candidate member is found, then the group is deleted.

Accordingly, group Scan2MZ201 is maintained after the third scan as group Scan3MZ201 with the only candidate member (201.27, 18193). Since, however, the fourth scan did not produce an additional candidate member for this group, this group is deleted after the fourth scan.

It should be added, that in the representation used here different groups may have the same name. After the third scan there are two groups having the name Scan3MZ201 one having only one candidate member, included after the headline "Potential peaks with one observation (s)" and one including two candidate members, included under the headline "Potential peaks with two observations (s)".

The interpolation of a missing data point can be seen on grouping protocol pages 13 to 17 of FIGS. 33 to 35. On the basis of data point (200.37, 25053) of scan 6 a potential peak or group was established which is denoted as Scan6MZ200 on grouping protocol page 13. The seventh scan gave no additional candidate member for this group, so that this group, now denoted Scan7MZ200 is shown on grouping protocol 15 to have only one candidate member (see at 32). The corresponding predictive mass window of this group is [200.08, 200.65]. In scan 8 data point [200.37, 34490] is found, which falls with its m/z value in this predictive mass window. Accordingly, this data point is added to group Scan7MZ200, and this group, now denoted Scan8MZ200 is shown on grouping protocol page 17 to include three data points (see at 34), the additional data point (200.37, 29771) being obtained by linear interpolation to fill in the missing data point of scan 7.

The first data point of the peak shown in FIG. 26 is found in scan 9, namely the data point (204.73, 34040) and on the basis of this point the potential group or peak Scan9MZ205 is established as shown on grouping protocol pages 20 and 21 of FIGS. 36 and 37. This group is marked on grouping protocol page 20 and the following grouping protocol pages by arrows. Scans 10 to 34 each give a further member of the group or peak according to FIG. 26. In scan 35, see grouping protocol page 97 in FIG. 75, no further candidate member of this group or peak is found, so that after scan 35 this peak or group, now denoted Scan35MZ205, still is shown on grouping protocol page 99 to have 26 members (26 observations) as on grouping protocol page 96 in FIG. 74 (there denoted as Scan34MZ205) after scan 34.

Scan 36 (compare grouping protocol page 100) found no additional candidate member of this group or peak, since there is no m/z value falling in the current predictive mass window [204.72, 205.12] of this group or peak (see at 28). Accordingly, group Scan35MZ205 formed by 26 data points is closed for further adding of candidate members after scan 36.

The peak or group shown in FIG. 26 fulfills the intensity condition, the unimodality condition and the kurtosis condition. Preferably, these conditions are applied to each potential group or peak having four candidate members, so that only such data points of a respective group and only such groups are maintained as potential groups corresponding to a potential peak which already fulfill all these criteria or may be fulfilled on the basis of additional candidate member to be added to the respective group. This means, those data points may be deleted from a respective group or those groups may be deleted which do not fulfill or cannot fulfill any one of these conditions in the sense that even on the basis of additional candidate members possibly to be found in the subsequent grouping these conditions cannot be fulfilled. However, one may also implement the grouping such that the intensity condition, unimodality condition and the kurtosis condition are only applied after closing of a group for further adding of candidate members, so that this group is discarded when one of these conditions is not fulfilled, and is maintained as group representing a respective peak if all these conditions are fulfilled.

It should be noted that as mass-to-charge interval defining a group or peak after closing this group or peak for adding of further candidate member either the last posterior mass window (i.e. predictive 95%-mass-window for the further scans, in which no additional potential member was found) which in the case of the peak according to FIG. 26 is the mass window shown at 28 on FIG. 76, or alternatively an interval defined by the lowest and highest m/z value of the data points belonging to this group or peak. As detection time interval preferably the lowest and highest time value of the data points belonging to this group or peak is taken, in the case of this group or peak Scan35MZ205 the interval [918.14(s), 970.66(s)]. Alternatively, the scan number interval could be used, in the case of this group or scan Scan35MZ205 the interval [9, 34] defined by the scan numbers of the first and the last data points added to the group.

The grouping protocol pages shown in FIGS. 27 to 78 show the course of the grouping also with respect to other groups associated to potential peaks, which, however, get discarded in the course of the grouping, in particular because no further candidate member was found in two subsequent scans. The protocol allows to follow the grouping process and the data processing, since the following information is given:

For each scan it is indicated, which data points have been found. It is then indicated, which potential peaks have been supplemented with these data points and which consequences arose: Updating (how and why), ending with result (discarding of the points or combination to one peak) and reason.

Potential peaks, which are ended since in two subsequent scans no additional data point was found to fall in the current mass window, are listed, the consequences are indicated: Ending with result (discarding the points or combination to a peak) and reason.

If a potential peak comes over the thresholds i) more than four candidate members in the respective group and ii) sufficient intensity, then the decision over discarding of the data points or identification as real peak is visualized: For the shown excerpt from the grouping protocol this applies only to the peak shown in FIG. 26, FIG. 26 being this visualization.

At the end of each scan the current potential peaks are listed, including their current data: m/z values intensities, additional m/z value and intensity values obtained from linear interpolation to fill up gaps of missing data points, parameter of the t-distribution, and predictive mass window for the next scan.

Referring to the implementation of the grouping in the present embodiment, according to which the grouping is effected in working mass windows, it should be added, that overlapping working mass windows may be provided, so that it is possible to effect the grouping also with respect to peaks at the boundary or crossing the boundary of two working mass windows along the m/z axis. If there is a peak in the overlapping m/z range, then this peak will be found twice, one time on the basis of each of the two overlapping working mass windows. One of the two peaks may then be discarded.

Further Embodiments

The invention is not limited to the embodiments considered here. E.g. the invention may be applied to measurement situations with higher dimensionality than three. For example, one could branch off a flow of substances present after the chromatography unit to a spectrometer, e.g. UV-spectrometer. In this case one would obtain additional intensity spectra (UV intensity over wavelengths) which are coupled with the mass spectra on the basis of a common time axis obtained immediately or after time standardization. The measurement data for such a measurement situation would have five dimensions: Time, mass-to-charge ratio, mass spectrometer intensity, wavelength and UV intensity. Another possibility is to effect in parallel two types of ionization techniques, e.g. ESI ionization and APCI ionization, each being coupled with a respective mass spectrometer. In this case one would obtain two mass spectra coupled by a common time axis, namely an ESI mass spectrum and a APCI mass spectrum, so that again five dimensions are obtained, if combined with UV spectroscopy as well then altogether seven dimensions.

Further, the invention can be applied to completely different analytical and detection techniques.

Yet another aspect provides a method for grouping measurement data obtained by effecting two or more techniques to provide characterization data characterizing at least one sample with respect to characterizing substances. According to one particular aspect, the grouping is effected on the basis of at least one statistical distribution of deviations of a respective characterizing measurement value. According to another particular aspect, the grouping is effected on the basis of at least one collective characteristic of a plurality of respective quantitative measurement values.

What is claimed is:

1. A method for analyzing a sample to provide characterization data with respect to at least one constituent of a sample, the method comprising:
   (a) in an analyzing system, effecting at least one first analytical technique selected from the group of separation techniques including (i) separation of constituents of the sample, (ii) separation of products resulting from a first analytical technique, and (iii) separation of constituents of the sample and products resulting from a first analytical technique, wherein the constituents include any combination selected from the group consisting of (i) chemical constituents, (ii) biological constituents, and (iii) biochemical constituents, and
      wherein the separation techniques are effected with respect to at least one first differentiating characteristic of constituents or products;
   (b) in the analyzing system, effecting a further analytical technique with respect to constituents or products already separated or in the process of being separated,
      wherein the further analytical technique is an analytical and detection technique for characterizing separated constituents or products using at least one basis selected from said group including a product resulting from a first analytical technique and a further differentiating characteristic,
      wherein the analyzing system further comprises detection hardware providing measurement data in terms of at least two characterizing measurement quantities, namely a first quantity of the characterizing measurement quantities reflecting a product obtained from effecting step (a) at least once and a second quantity of the characterizing measurement quantities reflecting at least one of said group including a product obtained from effecting step (a) at least once and the further differentiating characteristic;
   (c) in a data processing system having a processor and associated data storage, storing in the data storage a plurality data tuples for associating a first value associated with the first quantity of the characterizing measurement quantities with a second value associated with the second quantity of the characterizing measurement quantities;
   (d) with the said data processing system, grouping the data tuples into intervals according to at least one of the characterization measurement value, wherein the intervals are each associated with a particular one of the constituents or products, wherein said grouping is based on a statistical distribution of deviations from a characteristic value associated with the constituents or products; and
   (e) with the said data processing system providing an output of data reflecting a data set indicative of the data tuples or a visualization of the data set, wherein the providing of the output of data comprises a step selected from the group of steps consisting of storing data in said data storage, displaying data on a display screen, and printing data.

2. The method of claim 1, wherein the grouping of step (d) is further based on a collective characteristic of a plurality of characterization measurement quantities each belonging to a respective one of said data tuples.

3. The method of claim 1, wherein the grouping of step (d) is further based on a collective characteristic comprising a mathematical function at least partially defined by the data tuples.

4. The method of claim 1, wherein the grouping of step (d) comprises: (d3) according to a predetermined access schedule, accessing a given data tuple of the plurality of data tuples; and (d5) identifying the given data tuple as a candidate member of a given group of data tuples, wherein the given group is associated to a given constituent or product.

5. The method of claim 4, wherein identifying the given data tuple as a candidate member of a given group is dependent on fulfilling an identification condition.

6. The method of claim 4, wherein the grouping of step (d) further comprises: (d6) if an abort criterion is fulfilled, aborting the grouping; and (d9) repeating steps (d3) to (d6) until the grouping is aborted.

7. The method of claim 1, wherein the characteristic value associated with the constituents or products is a mean characterizing measurement value associated with the constituents or products.

8. The method of claim 1, wherein the statistical distribution of deviations is predicated on initialization data.

9. The method of claim 1, wherein the intervals are confidence intervals.

10. The method of claim 1, wherein during the grouping of step (d), the intervals are configured based in part on data tuples already grouped.

11. The method of claim 1, wherein the grouping of step (d) includes a determination of whether a characterizing measurement quantity of a given data tuple is within the statistical distribution of deviations.

12. The method of claim 11, wherein the statistical distribution of deviations is updated based on the determination of whether the characterization measurement quantity is within the statistical distribution of deviations.

13. The method of claim 1, wherein the grouping of step (d) comprises:
   assuming a current statistical distribution of deviations based on initialization data;
   determining at least one current interval based on the current statistical distribution of deviations;
   according to a predetermined access schedule, accessing a given data tuple of the plurality of data tuples;
   determining whether a value of the given data tuple is within the current interval;
   if the value of the given data tuple is within the current interval:
      (i) associating the data tuple as a candidate member of a given group of data tuples;
      (ii) based in part on the current statistical distribution, calculating an updated current statistical distribution of deviations as a prior distribution of deviations with respect to data tuples not already grouped;
   if an abort criterion is fulfilled, aborting the grouping.

14. The method of claim 13, wherein the plurality of data tuples are ordered in a listing, and wherein the given data tuple is the next data tuple in the listing.

15. The method of claim 13, wherein calculating the updated current statistical distribution is further based on a location of the characterization measurement quantity within the current interval.

16. The method of claim 13, further comprising: repeating the grouping of step (d) until the abortion criterion is fulfilled.

17. The method of claim 1, wherein the first analytical technique is further adapted to effect a separation of the constituents or products on the bases of a property selected from the group of a chemical effect, a physical effect, a kinetic property, and an equilibrium property.

18. The method of claim 1, wherein the first analytical technique further comprises a technique selected from the group consisting of a chromatographic technique and an electrophoretic technique.

19. The method of claim 1, wherein the first analytical technique comprises a mass spectrometric technique.

20. The method of claim 19, wherein the mass spectrometric technique is a technique selected from the group including an electrospray ionization technique and a MALDI technique.

21. The method of claim 1, wherein the further analytical technique comprises a mass spectrometric technique.

22. The method of claim 21, wherein the mass spectrometric technique is a technique selected from the group including an electrospray ionization technique and a MALDI technique.

23. The method of claim 1, wherein the at least two characterizing measurement quantities are any combination of quantities selected from the group of scan number, mass-to-charge ratio, ion intensity and detection time.

24. A machine readable storage device containing a set of computer code configured to control execution of steps (c), (d) and (e) of the method of claim 1.

25. The method of claim 1, wherein the further analytical technique is further adapted to effect a separation of the constituents or products on the bases of a property selected from the group of a chemical effect, a physical effect, a kinetic property, and an equilibrium property.

26. A system for analyzing a sample by effecting two or more techniques to provide characterization data with respect to a constituent comprising:
 (a) a first analyzing unit for effecting at least one first analytical technique selected from the group of separation techniques including (i) separation of constituents of the sample, (ii) separation of products resulting from a first analytical technique, and (iii) separation of constituents of the sample and products resulting from a first analytical technique, wherein the constituents include any combination selected from the group including (i) chemical constituents, (ii) biological constituents, and (iii) biochemical constituents, and wherein the separation techniques are effected with respect to at least one first differentiating characteristic of constituents or products;
 (b) a further analyzing unit for effecting a further analytical technique with respect to constituents or products already separated or in the process of being separated, wherein the further analytical technique is an analytical and detection technique for characterizing separated constituents or products using at least one basis selected from the group including a product resulting from a first analytical technique and a further differentiating characteristic, the further analyzing unit includes detection hardware for providing measurement data in terms of at least two characterizing measurement quantities, a first quantity of the characterizing measurement quantities reflecting a product obtained from effecting step (a) at least once and a second quantity of the characterizing measurement quantities reflecting at least one of the group including a product obtained from effecting step (a) at least once and the further differentiating characteristic;
 (c) a control unit having at least a processor and associated data storage,
 (d) program logic stored in data storage and executable by the processor for: (i) providing a plurality data tuples for associating the first quantity of the characterizing measurement quantities with the second quantity of the characterizing measurement quantities; (ii) grouping the data tuples into intervals according to at least one of the characterization measurement quantities, wherein the intervals are each associated with a particular one of the constituents or products, wherein grouping is based on a statistical distribution of deviations from a characteristic value associated with the constituents or products; and (iii) providing an output of data reflecting a data set indicative of the data tuples or a visualization of the data set, wherein the output of data comprises a step selected from the group including storing data in a data storage, displaying data on a display screen, and printing data.

27. A method for analyzing a sample to provide characterization data with respect to at least one constituent of a sample, the method comprising:
 (a) receiving at least two characterizing measurement quantities, a first quantity of the characterizing measurement quantities reflecting a product obtained from a first analytical technique performed on the sample at least once and a second quantity of the characterizing measurement quantities reflecting a product obtained from a further analytical technique performed with respect to constituents or products of the sample;
 (b) generating a plurality data tuples for associating the first quantity of the characterizing measurement quantities and the second quantity of the characterizing measurement quantities; and
 (c) grouping the data tuples into intervals according to at least one of the characterizing measurement quantities, wherein the intervals are each associated with a particular one of the constituents or products of the sample, wherein the grouping is based on a statistical distribution of deviations from a characteristic value associated with the constituents or products;
 wherein steps (a), (b) and (c) are performed in a data processing system having a processor and associated data storage.

28. A machine readable storage device storing a computer program for executing steps (a)-(c) of the method of claim 27.

29. A computer server having the storage device according to claim 28.

30. The computer server of claim 29, further comprising: a communications link for providing access to the stored computer program.

31. The method of claim 1, further comprising the step (f) of further analyzing the sample, constituents or products based on the data set indicative of the data tuples.

* * * * *